US012605425B2

(12) United States Patent     (10) Patent No.:   US 12,605,425 B2

Sibson et al.     (45) Date of Patent:    Apr. 21, 2026

(54) TNF MUTEINS AND USES THEREOF

(71) Applicant: Oxford University Innovation Limited, Oxford (GB)

(72) Inventors: Nicola R. Sibson, Oxford (GB); Daniel C. Anthony, Oxford (GB); Sandra J. Campbell, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 1102 days.

(21) Appl. No.: 17/621,711

(22) PCT Filed: Jun. 26, 2020

(86) PCT No.: PCT/GB2020/051560
§ 371 (c)(1),
(2) Date: Dec. 22, 2021

(87) PCT Pub. No.: WO2020/260900
PCT Pub. Date: Dec. 30, 2020

(65) Prior Publication Data
US 2022/0387557 A1     Dec. 8, 2022

(30) Foreign Application Priority Data
Jun. 28, 2019    (GB) ..................................... 1909390

(51) Int. Cl.
| | |
|---|---|
| *A61K 38/19* | (2006.01) |
| *A61K 31/198* | (2006.01) |
| *A61K 31/337* | (2006.01) |
| *A61K 31/506* | (2006.01) |
| *A61K 31/704* | (2006.01) |
| *A61K 38/00* | (2006.01) |
| *A61K 39/395* | (2006.01) |
| *A61K 49/10* | (2006.01) |
| *A61P 35/00* | (2006.01) |
| *C07K 14/525* | (2006.01) |

(52) U.S. Cl.
CPC .......... *A61K 38/191* (2013.01); *A61K 31/198* (2013.01); *A61K 31/337* (2013.01); *A61K 31/506* (2013.01); *A61K 31/704* (2013.01); *A61K 39/3955* (2013.01); *A61K 49/105* (2013.01); *A61P 35/00* (2018.01); *C07K 14/525* (2013.01); *A61K 38/00* (2013.01)

(58) Field of Classification Search
CPC .. A61K 38/191; A61K 31/198; A61K 31/337; A61K 31/506; A61K 31/704; A61K 39/3955; A61K 49/105; A61K 38/00; A61K 31/711; A61P 35/00; C07K 14/525
See application file for complete search history.

(56) References Cited

FOREIGN PATENT DOCUMENTS

| | | |
|---|---|---|
| EP | 0 563 714 A2 | 10/1993 |
| GB | 2 275 683 A | 9/1994 |
| WO | 99/62315 A2 | 12/1999 |
| WO | 2011/070358 A2 | 6/2011 |

OTHER PUBLICATIONS

Shibata H, Yoshioka Y, Ohkawa A, et al. Creation and X-ray structure analysis of the tumor necrosis factor receptor-1-selective mutant of a tumor necrosis factor-alpha antagonist. J Biol Chem. Jan. 11, 2008;283(2):998-1007. doi: 10.1074/jbc.M707933200. Epub Nov. 14, 2007. PMID: 18003610. (Year: 2007).*
Bork P. Powers and pitfalls in sequence analysis: the 70% hurdle. Genome Res. (Year: 2000).*
Skolnick J. et al. From genes to protein structure and function: novel applications of computational approaches in the genomic era. Trends Biotechnol. (Year: 2000).*
Tokuriki N. et al. Stability effects of mutations and protein evolvability. Curr Opin Struct Biol. (Year: 2009).*
Nomura, T., et al. Novel protein engineering strategy for creating highly receptor-selective mutant TNFs. Biochemical and biophysical research communications (Year: 2009).*
International Preliminary Report on Patentability for WO 2020/260900 (PCT/GB2020/051560), dated Dec. 28, 2021, pp. 1-8.
Bryson et al., 2010;24(1):1-8.
Lopez-Ramirez et al. J Immunol. 2012;189(19):3130-3139.
Perry et al., 2008. Drugs R D. 9(6): 385-96.
Serres et al., Proc Natl Acad Sci U S A. 2012;109(17): 6674-6679.
Shibata et al., 2008a. J Biol Chem. 11;283(2): 998-1007.
Shibata et al., 2008b. Cytokine. 44(2): 229-33.
Soto et al., Neuro Oncol. 2014;16(4):540-551.
International Search Report and Written Opinion for WO 2020/260900 (PCT/GB2020/051560), dated Aug. 31, 2020, pp. 1-12.
UK Search Report for GB 1909390.5, dated Dec. 18, 2019, pp. 1-5.
Nomura T. et al: "Novel protein engineering strategy for creating highly receptor-selective mutant TNFs", Biochemical and Biophysical Research Communications, Els Ev I Er, Amsterdam, NL, vol. 388, No. 4, Oct. 30, 2009 (Oct. 30, 2009), pp. 667-671.
Journal of Biological Chemistry, 1993, vol. 268 No. 35, Loetscher H et al., "Human tumor necrosis factor alpha (TNF alpha) mutants with exclusive specificity for the 55-kDa or 75-kDa TNF receptors", pp. 26350-26357.
Biochem Biophys Rep, 2016, vol. 7, Ando D. et al., "Creation of mouse TNFR2-selective agonistic TNF mutants using a phage display technique", pp. 309-315.

(Continued)

*Primary Examiner* — Gary B Nickol

(74) *Attorney, Agent, or Firm* — Thomas|Horstemeyer, LLP

(57) ABSTRACT

The present invention relates to tumour necrosis factor (TNF) muteins with improved properties, and in particular to TNF muteins which are agonists of, and bind selectively to, tumour necrosis factor receptor 1 (TNFR1). Compositions comprising the TNF muteins, which may additionally comprise appropriate anticancer agents or imaging agents are provided. The use of the muteins of the invention in methods of treating or detecting a tumour are also provided. The invention also provides nucleic acids (e.g. vectors) encoding the TNF muteins and host cells comprising the nucleic acids.

19 Claims, 9 Drawing Sheets

Figure 1:
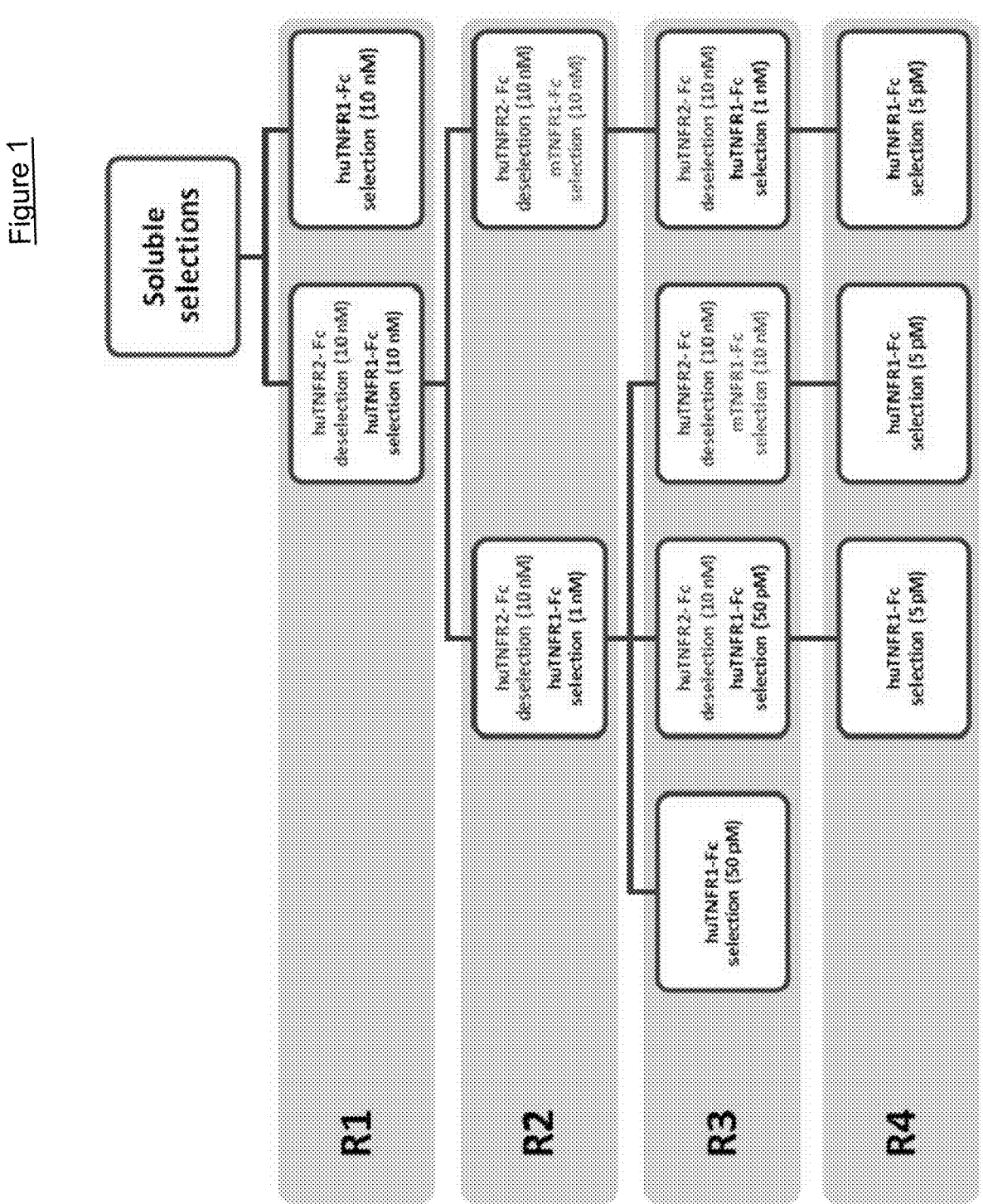

Specification includes a Sequence Listing.

(56)          References Cited

OTHER PUBLICATIONS

Shibata et al: "Role of amino acid residue 90 in bioactivity and receptor binding capacity of tumor necrosis factor mutants", Biochimica Et Biophysica Acta (BBA)—Proteins & Proteomics, Elsevier, Netherlands, vol. 1774, No. 8, Aug. 6, 2007 (Aug. 6, 2007), pp. 1029-1035.

John J. Connell et al: "Selective Permeabilization of the Blood-Brain Barrier at Sites of Metastasis", Journal of the National Cancer Institute, vol. 105, No. 21, Oct. 9, 2013 (Oct. 9, 2013), pp. 1634-1643.

TNFR1 selective TNF mutants induce transient BBB permeabilisationat sites of brain metastases, Brain Metastasis Research Symposium: From Basic Science to Clinics 2019, Nov. 29, 2018: "BBB symposium Nov. 29, 2018", pp. 1-13.

Development of new TNFR1-selective agonist TNF mutants to include BBB permeabilisation at sites of brain metastases, Jun. 28, 2019: "Vienna Presentation", pp. 1-14.

* cited by examiner

Figure 2

| Analyte | Relative binding | | | |
| --- | --- | --- | --- | --- |
| | hTNFR1 | hTNFR2 | mTNFR1 | mTNFR2 |
| hTNF | +++ | +++ | +++ | +/- |
| hTNF R32W S86T | ++ | - | - | - |
| mTNF | +++ | +++ | +++ | +++ |
| A1 | +++ | + | ++ | - |
| A2 | +++ | - | ++ | - |
| A3 | +++ | - | ++ | - |
| A6 | - | - | - | - |
| A7 | +++ | - | +++ | - |
| A9 | +++ | ++ | ++ | +/- |
| A10 | +++ | - | ++ | - |
| B2 | +++ | + | +++ | - |
| B3 | +++ | - | ++ | ND |
| B4 | +++ | - | ++ | - |
| B5 | +++ | - | ++ | - |
| B6 | +++ | - | +++ | - |
| B9 | +++ | - | +++ | - |
| C2 | +++ | - | ++ | - |
| C3 | +++ | +/- | ++ | ND |
| C4 | +++ | - | +++ | - |
| C8 | +++ | - | +++ | - |
| C9 | +++ | +/- | ++ | - |
| D1 | +++ | +/- | +++ | - |
| D3 | +++ | - | +++ | ND |
| E3 | +++ | - | +++ | - |
| E9 | - | - | - | - |
| F1 | +++ | +/- | ++ | - |
| F3 | +++ | - | ++ | +/- |
| F4 | +++ | - | +++ | - |
| F7 | +++ | - | +++ | - |
| F9 | +++ | - | +/- | - |
| G4 | +++ | - | +++ | - |
| H9 | +++ | - | ++ | - |

SEQUENCE LISTING

```
<160> NUMBER OF SEQ ID NOS: 40

<210> SEQ ID NO 1
<211> LENGTH: 157
<212> TYPE: PRT
<213> ORGANISM: Homo sapiens
```

-continued

```
<400> SEQUENCE: 1

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 2
<211> LENGTH: 157
<212> TYPE: PRT
<213> ORGANISM: Artificial Sequence
<220> FEATURE:
<223> OTHER INFORMATION: TNF Mutein G4

<400> SEQUENCE: 2

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ser Ser Thr Tyr Asn Pro Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 3
<211> LENGTH: 157
<212> TYPE: PRT
<213> ORGANISM: Artificial sequence
<220> FEATURE:
<223> OTHER INFORMATION: TNF Mutein B5
```

-continued

<400> SEQUENCE: 3

```
Val His Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Thr Gly Thr Tyr Val Asp Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 4
<211> LENGTH: 157
<212> TYPE: PRT
<213> ORGANISM: Artificial sequence
<220> FEATURE:
<223> OTHER INFORMATION: TNF muteins B6

<400> SEQUENCE: 4

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Thr Gly Thr Tyr Ser Tyr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 5
<211> LENGTH: 157
<212> TYPE: PRT
<213> ORGANISM: Artificial sequence
<220> FEATURE:

```
<223> OTHER INFORMATION: TNF mutein F3

<400> SEQUENCE: 5

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Thr Thr Thr Tyr Arg Leu Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Val Ala Leu
145                 150                 155

<210> SEQ ID NO 6
<211> LENGTH: 157
<212> TYPE: PRT
<213> ORGANISM: Artificial sequence
<220> FEATURE:
<223> OTHER INFORMATION: TNF mutein F7

<400> SEQUENCE: 6

Val His Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ser Glu Thr Val Val Gly Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Val Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 7
<211> LENGTH: 157
<212> TYPE: PRT
<213> ORGANISM: Artificial sequence
```

```
<220> FEATURE:
<223> OTHER INFORMATION: TNF mutein B2

<400> SEQUENCE: 7

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Thr Ala Ser Tyr Ser Gly Lys Val Asn Leu Leu Ser Ala
                85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 8
<211> LENGTH: 157
<212> TYPE: PRT
<213> ORGANISM: Artificial sequence
<220> FEATURE:
<223> OTHER INFORMATION: TNF mutein B4

<400> SEQUENCE: 8

Val Arg Ser Ser Ser His Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ser Glu Ser His Asp Gly Lys Val Asn Leu Leu Ser Ala
                85                  90                  95

Ile Lys Ser Pro Cys Gln Arg Glu Thr Pro Glu Gly Ala Glu Ala Lys
                100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155

<210> SEQ ID NO 9
<211> LENGTH: 157
<212> TYPE: PRT
```

```
<213> ORGANISM: Artificial sequence
<220> FEATURE:
<223> OTHER INFORMATION: TNF mutein C4

<400> SEQUENCE: 9

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ser His Ser Val Glu Gly Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 10
<211> LENGTH: 157
<212> TYPE: PRT
<213> ORGANISM: Artificial sequence
<220> FEATURE:
<223> OTHER INFORMATION: TNF mutein C8

<400> SEQUENCE: 10

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ser Gln Thr His Asp Gly Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 11
<211> LENGTH: 157
```

<212> TYPE: PRT
<213> ORGANISM: Artificial sequence
<220> FEATURE:
<223> OTHER INFORMATION: TNF mutein C9

<400> SEQUENCE: 11

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Ile Asn Gly Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Thr Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Asp
    130                 135                 140

Ala Asp Ser Gly Gln Val Tyr Phe Gly Ile Ile Ala Leu
145                 150                 155
```

<210> SEQ ID NO 12
<211> LENGTH: 6
<212> TYPE: PRT
<213> ORGANISM: Artificial sequence
<220> FEATURE:
<223> OTHER INFORMATION: G4 domain

<400> SEQUENCE: 12

```
Ser Ser Thr Tyr Asn Pro
1               5
```

<210> SEQ ID NO 13
<211> LENGTH: 6
<212> TYPE: PRT
<213> ORGANISM: Artificial sequence
<220> FEATURE:
<223> OTHER INFORMATION: B5 domain

<400> SEQUENCE: 13

```
Thr Gly Thr Tyr Val Asp
1               5
```

<210> SEQ ID NO 14
<211> LENGTH: 6
<212> TYPE: PRT
<213> ORGANISM: Artificial sequence
<220> FEATURE:
<223> OTHER INFORMATION: B6 domain

<400> SEQUENCE: 14

```
Thr Gly Thr Tyr Ser Tyr
1               5
```

<210> SEQ ID NO 15
<211> LENGTH: 6

```
<212> TYPE: PRT
<213> ORGANISM: Artificial sequence
<220> FEATURE:
<223> OTHER INFORMATION: F3 domain

<400> SEQUENCE: 15

Thr Thr Thr Tyr Arg Leu
1               5

<210> SEQ ID NO 16
<211> LENGTH: 6
<212> TYPE: PRT
<213> ORGANISM: Artificial sequence
<220> FEATURE:
<223> OTHER INFORMATION: F7 domain

<400> SEQUENCE: 16

Ser Glu Thr Val Val Gly
1               5

<210> SEQ ID NO 17
<211> LENGTH: 6
<212> TYPE: PRT
<213> ORGANISM: Artificial sequence
<220> FEATURE:
<223> OTHER INFORMATION: B2 domain

<400> SEQUENCE: 17

Thr Ala Ser Tyr Ser Gly
1               5

<210> SEQ ID NO 18
<211> LENGTH: 6
<212> TYPE: PRT
<213> ORGANISM: Artificial sequence
<220> FEATURE:
<223> OTHER INFORMATION: B4 domain

<400> SEQUENCE: 18

Ser Glu Ser His Asp Gly
1               5

<210> SEQ ID NO 19
<211> LENGTH: 6
<212> TYPE: PRT
<213> ORGANISM: Artificial sequence
<220> FEATURE:
<223> OTHER INFORMATION: C4 domain

<400> SEQUENCE: 19

Ser His Ser Val Glu Gly
1               5

<210> SEQ ID NO 20
<211> LENGTH: 6
<212> TYPE: PRT
<213> ORGANISM: Artificial sequence
<220> FEATURE:
<223> OTHER INFORMATION: C8 domain

<400> SEQUENCE: 20

Ser Gln Thr His Asp Gly
1               5

<210> SEQ ID NO 21
<211> LENGTH: 6
<212> TYPE: PRT
```

<213> ORGANISM: Artificial sequence
<220> FEATURE:
<223> OTHER INFORMATION: C9 domain

<400> SEQUENCE: 21

Ala Val Thr Tyr Gln Thr
1               5

<210> SEQ ID NO 22
<211> LENGTH: 6
<212> TYPE: PRT
<213> ORGANISM: Artificial sequence
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is A, G, S, T, E, H, Q, D, I, L or M
<220> FEATURE:
<221> NAME/KEY: VARIANT
<222> LOCATION: (3)..(3)
<223> OTHER INFORMATION: X is S or T
<220> FEATURE:
<221> NAME/KEY: VARIANT
<222> LOCATION: (4)..(4)
<223> OTHER INFORMATION: X is Y, V or H
<220> FEATURE:
<221> NAME/KEY: VARIANT
<222> LOCATION: (5)..(5)
<223> OTHER INFORMATION: X is S, V, R, N, D, E, I, L, M or T
<220> FEATURE:
<221> NAME/KEY: VARIANT
<222> LOCATION: (6)..(6)
<223> OTHER INFORMATION: X is G, D, Y, L, P, E, A, V, I, M, F or W

<400> SEQUENCE: 22

Xaa Xaa Xaa Xaa Xaa Xaa
1               5

<210> SEQ ID NO 23
<211> LENGTH: 6
<212> TYPE: PRT
<213> ORGANISM: Artificial sequence
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is A, G, S, T, E, H or Q
<220> FEATURE:
<221> NAME/KEY: VARIANT
<222> LOCATION: (3)..(3)
<223> OTHER INFORMATION: X is S or T
<220> FEATURE:
<221> NAME/KEY: VARIANT
<222> LOCATION: (4)..(4)
<223> OTHER INFORMATION: X is Y, V or H
<220> FEATURE:
<221> NAME/KEY: VARIANT
<222> LOCATION: (5)..(5)
<223> OTHER INFORMATION: X is S, V, R, N, D or E
<220> FEATURE:
<221> NAME/KEY: VARIANT
<222> LOCATION: (6)..(6)
<223> OTHER INFORMATION: X is G, D, Y, L or P

<400> SEQUENCE: 23

```
Xaa Xaa Xaa Xaa Xaa Xaa
1               5

<210> SEQ ID NO 24
<211> LENGTH: 6
<212> TYPE: PRT
<213> ORGANISM: Artificial sequence
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is A, G, S, T or E
<220> FEATURE:
<221> NAME/KEY: VARIANT
<222> LOCATION: (3)..(3)
<223> OTHER INFORMATION: X is S or T
<220> FEATURE:
<221> NAME/KEY: VARIANT
<222> LOCATION: (4)..(4)
<223> OTHER INFORMATION: X is Y or V
<220> FEATURE:
<221> NAME/KEY: VARIANT
<222> LOCATION: (5)..(5)
<223> OTHER INFORMATION: X is S, V, R or N
<220> FEATURE:
<221> NAME/KEY: VARIANT
<222> LOCATION: (6)..(6)
<223> OTHER INFORMATION: X is G, D, Y, L or P

<400> SEQUENCE: 24

Xaa Xaa Xaa Xaa Xaa Xaa
1               5

<210> SEQ ID NO 25
<211> LENGTH: 6
<212> TYPE: PRT
<213> ORGANISM: Artificial sequence
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is G, S, T or E
<220> FEATURE:
<221> NAME/KEY: VARIANT
<222> LOCATION: (4)..(4)
<223> OTHER INFORMATION: X is Y or V
<220> FEATURE:
<221> NAME/KEY: VARIANT
<222> LOCATION: (5)..(5)
<223> OTHER INFORMATION: X is S, V, R or N
<220> FEATURE:
<221> NAME/KEY: VARIANT
<222> LOCATION: (6)..(6)
<223> OTHER INFORMATION: X is G, D, Y, L or P

<400> SEQUENCE: 25

Xaa Xaa Thr Xaa Xaa Xaa
1               5

<210> SEQ ID NO 26
<211> LENGTH: 6
<212> TYPE: PRT
<213> ORGANISM: Artificial sequence
```

```
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is G, S or T
<220> FEATURE:
<221> NAME/KEY: VARIANT
<222> LOCATION: (5)..(5)
<223> OTHER INFORMATION: X is S, V, R or N
<220> FEATURE:
<221> NAME/KEY: VARIANT
<222> LOCATION: (6)..(6)
<223> OTHER INFORMATION: X is D, Y, L or P

<400> SEQUENCE: 26

Xaa Xaa Thr Tyr Xaa Xaa
1               5

<210> SEQ ID NO 27
<211> LENGTH: 6
<212> TYPE: PRT
<213> ORGANISM: Artificial sequence
<220> FEATURE:
<223> OTHER INFORMATION: TNF motif
<220> FEATURE:
<221> NAME/KEY: VARIANT
<222> LOCATION: (1)..(1)
<223> OTHER INFORMATION: X is S or T
<220> FEATURE:
<221> NAME/KEY: VARIANT
<222> LOCATION: (2)..(2)
<223> OTHER INFORMATION: X is G or S
<220> FEATURE:
<221> NAME/KEY: VARIANT
<222> LOCATION: (5)..(5)
<223> OTHER INFORMATION: X is S, V or N
<220> FEATURE:
<221> NAME/KEY: VARIANT
<222> LOCATION: (6)..(6)
<223> OTHER INFORMATION: X is D, Y or P

<400> SEQUENCE: 27

Xaa Xaa Thr Tyr Xaa Xaa
1               5

<210> SEQ ID NO 28
<211> LENGTH: 157
<212> TYPE: PRT
<213> ORGANISM: Artificial sequence
<220> FEATURE:
<223> OTHER INFORMATION: TNF mutein consensus
<220> FEATURE:
<221> NAME/KEY: VARIANT
<222> LOCATION: (84)..(84)
<223> OTHER INFORMATION: X is S or T
<220> FEATURE:
<221> NAME/KEY: VARIANT
<222> LOCATION: (85)..(85)
<223> OTHER INFORMATION: X is A, G, S, T, E, H, Q, D, I, L or M
<220> FEATURE:
<221> NAME/KEY: VARIANT
<222> LOCATION: (86)..(86)
<223> OTHER INFORMATION: X is S or T
<220> FEATURE:
<221> NAME/KEY: VARIANT
<222> LOCATION: (87)..(87)
<223> OTHER INFORMATION: X is Y, V or H
<220> FEATURE:
<221> NAME/KEY: VARIANT
<222> LOCATION: (88)..(88)
```

<223> OTHER INFORMATION: X is S, V, R, N, D, E, I, L, M or T
<220> FEATURE:
<221> NAME/KEY: VARIANT
<222> LOCATION: (89)..(89)
<223> OTHER INFORMATION: X is G, D, Y, L, P, E, A, V, I, M, F or W

<400> SEQUENCE: 28

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Xaa Xaa Xaa Xaa Xaa Xaa Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
            115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 29
<211> LENGTH: 4
<212> TYPE: PRT
<213> ORGANISM: Homo sapiens

<400> SEQUENCE: 29

Leu Asn Arg Arg
1

<210> SEQ ID NO 30
<211> LENGTH: 4
<212> TYPE: PRT
<213> ORGANISM: Homo sapiens

<400> SEQUENCE: 30

Phe Ala Glu Ser
1

<210> SEQ ID NO 31
<211> LENGTH: 6
<212> TYPE: PRT
<213> ORGANISM: Artificial sequence
<220> FEATURE:
<223> OTHER INFORMATION: TNFR1 antagonist motif

<400> SEQUENCE: 31

Ser Thr Thr His Asn Gln
1               5

<210> SEQ ID NO 32
<211> LENGTH: 471
<212> TYPE: DNA
<213> ORGANISM: Artificial sequence
<220> FEATURE:

<223> OTHER INFORMATION: TNF mutein G4

<400> SEQUENCE: 32

```
gttcgttctt cctctcgtac cccatctgat aaacctgttg cccatgtcgt tgccaacccg      60
caggcagaag gccaactgca atggctgaat cgccgtgcaa atgcgctgct ggctaatggt     120
gttgagctgc gtgacaacca actggttgtg ccaagcgaag gcctgtatct gatctatagc     180
caggtgctgt ttaaaggtca aggttgcccg agcacgcatg tgctgctgac ccacaccatt     240
tcacgcatct ctagtaccta taatcccaaa gttaatctgc tgagcgctat taagagcccg     300
tgtcagcgtg aaacgccgga gggtgcagaa gcgaagccgt ggtacgagcc gatctatctg     360
ggtggcgtct ttcaactgga gaaaggtgat cgtctgagcg cagaaatcaa ccgtccggac     420
tacttggact ttgcggagtc cggtcaagtt tacttcggca tcattgcgtt g             471
```

<210> SEQ ID NO 33
<211> LENGTH: 471
<212> TYPE: DNA
<213> ORGANISM: Artificial sequence
<220> FEATURE:
<223> OTHER INFORMATION: TNF mutein B5

<400> SEQUENCE: 33

```
gttcattctt cctctcgtac cccatctgat aaacctgttg cccatgtcgt tgccaacccg      60
caggcagaag gccaactgca atggctgaat cgccgtgcaa atgcgctgct ggctaatggt     120
gttgagctgc gtgacaacca actggttgtg ccaagcgaag gcctgtatct gatctatagc     180
caggtgctgt ttaaaggtca aggttgcccg agcacgcatg tgctgctgac ccacaccatt     240
tcacgcatca ctgggaccta tgttgataaa gttaatctgc tgagcgctat taagagcccg     300
aggttgcccg agcacgcatg tgctgctgac ccacaccatt tcacgcatca ctgggaccta     360
tgttgataaa gttaatctgc tgagcgctat taagagcccg cagaaatcaa ccgtccggac     420
tacttggact ttgcggagtc cggtcaagtt tacttcggca tcattgcgtt g             471
```

<210> SEQ ID NO 34
<211> LENGTH: 471
<212> TYPE: DNA
<213> ORGANISM: Artificial sequence
<220> FEATURE:
<223> OTHER INFORMATION: TNF mutein B6

<400> SEQUENCE: 34

```
gttcgttctt cctctcgtac cccatctgat aaacctgttg cccatgtcgt tgccaacccg      60
caggcagaag gccaactgca atggctgaat cgccgtgcaa atgcgctgct ggctaatggt     120
gttgagctgc gtgacaacca actggttgtg ccaagcgaag gcctgtatct gatctatagc     180
caggtgctgt ttaaaggtca aggttgcccg agcacgcatg tgctgctgac ccacaccatt     240
tcacgcatca ctgggaccta ttcgtataaa gttaatctgc tgagcgctat taagagcccg     300
tgtcagcgtg aaacgccgga gggtgcagaa gcgaagccgt ggtacgagcc gatctatctg     360
ggtggcgtct ttcaactgga gaaaggtgat cgtctgagcg cagaaatcaa ccgtccggac     420
tacttggact ttgcggagtc cggtcaagtt tacttcggca tcattgcgtt g             471
```

<210> SEQ ID NO 35
<211> LENGTH: 471
<212> TYPE: DNA
<213> ORGANISM: Artificial sequence
<220> FEATURE:
<223> OTHER INFORMATION: TNF mutein F3

<400> SEQUENCE: 35
gttcgttctt cctctcgtac cccatctgat aaacctgttg cccatgtcgt tgccaacccg          60
caggcagaag gccaactgca atggctgaat cgccgtgcaa atgcgctgct ggctaatggt         120
gttgagctgc gtgacaacca actggttgtg ccaagcgaag gcctgtatct gatctatagc         180
caggtgctgt ttaaaggtca aggttgcccg agcacgcatg tgctgctgac ccacaccatt         240
tcacgcatca ctacgaccta taggcttaaa gttaatctgc tgagcgctat taagagcccg         300
tgtcagcgtg aaacgccgga gggtgcagaa gcgaagccgt ggtacgagcc gatctatctg         360
ggtggcgtct ttcaactgga gaaaggtgat cgtctgagcg cagaaatcaa ccgtccggac         420
tacttggact ttgcggagtc cggtcaagtt tacttcggca tcgttgcgtt g                  471

<210> SEQ ID NO 36
<211> LENGTH: 471
<212> TYPE: DNA
<213> ORGANISM: Artificial sequence
<220> FEATURE:
<223> OTHER INFORMATION: TNF mutein F7

<400> SEQUENCE: 36
gttcattctt cctctcgtac cccatctgat aaacctgttg cccatgtcgt tgccaacccg          60
caggcagaag gccaactgca atggctgaat cgccgtgcaa atgcgctgct ggctaatggt         120
gttgagctgc gtgacaacca actggttgtg ccaagcgaag gcctgtatct gatctatagc         180
caggtgctgt ttaaaggtca aggttgcccg agcacgcatg tgctgctgac ccacaccatt         240
tcacgcatca gtgagaccgt ggttggtaaa gttaatctgc tgagcgctat taagagcccg         300
tgtcagcgtg aaacgccgga gggtgcagaa gcgaagccgt ggtacgagcc gatctatctg         360
ggtggcgtct ttcaactgga gaaaggtgat cgtctgagcg tagaaatcaa ccgtccggac         420
tacttggact ttgcggagtc cggtcaagtt tacttcggca tcattgcgtt g                  471

<210> SEQ ID NO 37
<211> LENGTH: 471
<212> TYPE: DNA
<213> ORGANISM: Artificial sequence
<220> FEATURE:
<223> OTHER INFORMATION: TNF mutein B2

<400> SEQUENCE: 37
gttcgttctt cctctcgtac cccatctgat aaacctgttg cccatgtcgt tgccaacccg          60
caggcagaag gccaactgca atggctgaat cgccgtgcaa atgcgctgct ggctaatggt         120
gttgagctgc gtgacaacca actggttgtg ccaagcgaag gcctgtatct gatctatagc         180
caggtgctgt ttaaaggtca aggttgcccg agcacgcatg tgctgctgac ccacaccatt         240
tcacgcatca ctgcgtccta tagtggtaaa gttaatctgc tgagcgctat taagagcccg         300
tgtcagcgtg aaacgccgga gggtgcagaa gcgaagccgt ggtacgagcc gatctatctg         360
ggtggcgtct ttcaactgga gaaaggtgat cgtctgagcg cagaaatcaa ccgtccggac         420
tacttggact ttgcggagtc cggtcaagtt tacttcggca tcattgcgtt g                  471

<210> SEQ ID NO 38
<211> LENGTH: 471
<212> TYPE: DNA
<213> ORGANISM: Artificial sequence
<220> FEATURE:
<223> OTHER INFORMATION: TNF mutein B4

-continued

```
<400> SEQUENCE: 38
gttcgttctt cctctcatac cccatctgat aaacctgttg cccatgtcgt tgccaacccg     60
caggcagaag gccaactgca atggctgaat cgccgtgcaa atgcgctgct ggctaatggt    120
gttgagctgc gtgacaacca actggttgtg ccaagcgaag gcctgtatct gatctatagc    180
caggtgctgt ttaaaggtca aggttgcccg agcacgcatg tgctgctgac ccacaccatt    240
tcacgcatca gtgagtccca tgatggtaaa gttaatctgc tgagcgctat taagagcccg    300
tgtcagcgtg aaacgccgga gggtgcagaa gcgaagccgt ggtacgagcc gatctatctg    360
ggtggcgtct ttcaactgga aaaggtgat cgtctgagcg cagaaatcaa ccgtccggac    420
tacttggact ttgcggagtc cggtcaagtt tacttcggca tcattgcgtt g            471

<210> SEQ ID NO 39
<211> LENGTH: 471
<212> TYPE: DNA
<213> ORGANISM: Artificial sequence
<220> FEATURE:
<223> OTHER INFORMATION: TNF mutein C4

<400> SEQUENCE: 39
gttcgttctt cctctcgtac cccatctgat aaacctgttg cccatgtcgt tgccaacccg     60
caggcagaag gccaactgca atggctgaat cgccgtgcaa atgcgctgct ggctaatggt    120
gttgagctgc gtgacaacca actggttgtg ccaagcgaag gcctgtatct gatctatagc    180
caggtgctgt ttaaaggtca aggttgcccg agcacgcatg tgctgctgac ccacaccatt    240
tcacgcatca gtcattccgt ggagggtaaa gttaatctgc tgagcgctat taagagcccg    300
tgtcagcgtg aaacgccgga gggtgcagaa gcgaagccgt ggtacgagcc gatctatctg    360
ggtggcgtct ttcaactgga aaaggtgat cgtctgagcg cagaaatcaa ccgtccggac    420
tacttggact ttgcggagtc cggtcaagtt tacttcggca tcattgcgtt g            471

<210> SEQ ID NO 40
<211> LENGTH: 471
<212> TYPE: DNA
<213> ORGANISM: Artificial sequence
<220> FEATURE:
<223> OTHER INFORMATION: TNF mutein C8

<400> SEQUENCE: 40
gttcgttctt cctctcgtac cccatctgat aaacctgttg cccatgtcgt tgccaacccg     60
caggcagaag gccaactgca atggctgaat cgccgtgcaa atgcgctgct ggctaatggt    120
gttgagctgc gtgacaacca actggttgtg ccaagcgaag gcctgtatct gatctatagc    180
caggtgctgt ttaaaggtca aggttgcccg agcacgcatg tgctgctgac ccacaccatt    240
tcacgcatct cgcagaccca tgatgggaaa gttaatctgc tgagcgctat taagagcccg    300
tgtcagcgtg aaacgccgga gggtgcagaa gcgaagccgt ggtacgagcc gatctatctg    360
ggtggcgtct ttcaactgga aaaggtgat cgtctgagcg cagaaatcaa ccgtccggac    420
tacttggact ttgcggagtc cggtcaagtt tacttcggca tcattgcgtt g            471
```

TNF MUTEINS AND USES THEREOF

CROSS-REFERENCE TO RELATED APPLICATIONS

This application is the National Stage of International Application No. PCT/GB2020/051560, filed Jun. 26, 2020, which claims priority to GB 1909390.5, filed Jun. 28, 2019, which are entirely incorporated herein by reference.

The present invention relates to tumour necrosis factor (TNF, formerly known as TNFα) muteins with improved properties, and in particular to TNF muteins which are agonists of, and bind selectively to, tumour necrosis factor receptor 1 (TNFR1). The TNF muteins of the present invention can be used in a variety of therapeutic applications, particularly in permeabilising tumour vasculature. The ability to permeabilize tumour vasculature provides uses for the present TNF muteins in methods of imaging and/or of treating tumours. In particular, the TNF muteins may be used in methods of imaging and/or treating tumours of the central nervous system (CNS), including brain tumours. Compositions comprising said TNF muteins, which may additionally comprise appropriate anticancer agents or imaging agents are provided. The uses of the muteins of the invention in methods of treating or detecting a tumour are also provided. The invention also provides nucleic acids (e.g. vectors) encoding the TNF muteins and host cells comprising said nucleic acids.

Tumour Necrosis Factor (TNF) is a major inflammatory cytokine that has roles in host defence and inflammation. TNF was formerly known as TNFα, cachectin, and TNFα-1a and these terms may be used interchangeably. TNF is primarily produced in vivo as a type II transmembrane protein arranged in stable homotrimers. The transmembrane homotrimers are subjected to proteolytic cleavage to cause the release of the homotrimeric cytokine. TNF is thus active as a homotrimer. TNF is a target for inhibition in the treatment of numerous diseases, including rheumatoid arthritis (RA), juvenile arthritis, psoriatic arthritis, plaque psoriasis, ankylosing spondylitis, ulcerative colitis (UC), and Crohn's disease. However, TNF itself has also been shown to have therapeutic utilities.

In this respect, the present inventors have previously shown that it is possible to increase the permeability of tumour vasculature in the region surrounding a tumour by the systemic administration of TNF, which acts as a tumour vasculature permeabilising molecule (see WO 2011/070358, which is herein incorporated by reference).

The determination that TNF increases the permeability of tumour vasculature allowed the development of new methods of treating or detecting (e.g. imaging) tumours, which take advantage of the fact that, by increasing the permeability of tumour vasculature in the region surrounding a tumour, agents such as therapeutic agents (e.g. anticancer agents) or signal generating agents (e.g. imaging agents) are able to leave the vascular system more readily in the region of the tumour. Since the access of the relevant agent to the tumour is improved, this also improves the ability of the agent to perform its function in therapy of the tumour or in the imaging or detection thereof.

The systemic administration of TNF has no effect on normal vasculature and the permeabilising effect is thus specific to tumour vasculature (i.e. vasculature that is within, associated with, close to or adjacent to a tumour). As such, any agent (therapeutic or diagnostic) that is co-administered with TNF to a patient having a tumour will tend to leave the vascular system in a much higher amount or concentration in the region of the tumour, or surrounding the tumour, than elsewhere in the patient. This has the clear advantage that the agent will be present at higher concentrations in the regions in which its effect is desired, and will tend to be present at lower concentrations or be absent elsewhere in the patient. Furthermore, a generalised increase in vascular permeability is not desirable and would be likely to be associated with unwanted side effects. Whilst this is a clear advantage for tumours that occur throughout the body, this is particularly so in relation to the areas behind the blood brain barrier (BBB); the presence of the BBB is known to be key to protecting the brain, e.g. from bacterial infections. It is clear that a generalised breakdown of the BBB would compromise this protection and lead to unwanted side effects. This is clearly not desirable and thus the permeabilizing effects of TNF find particular utility in imaging, detecting and treating tumours of the CNS.

The effect of systemic administration of TNF on tumour vasculature is transient, such that normal levels of permeability of the tumour vasculature are restored subsequent to discontinuing the administration of TNF. In this way, as long as a therapeutic or signal generating agent is also present in the vasculature during the period of time in which vascular permeability is increased, it will be possible for the agent to pass through the relevant blood vessel wall resulting in it being present at higher concentrations in the regions in which its effect is desired. In circumstances where prolonged or generalised increases in vascular permeability are not be desirable, it is advantageous that the vascular permeability can be increased only for as long as is necessary to facilitate or ensure the access of the agent to the tumour. The restoration of normal levels of permeability of the tumour vasculature thus also acts to reduce or prevent unwanted side effects of the methods discussed herein. However, as the increase in vascular permeability is restricted to the site of the tumour, side effects associated with increased vascular permeability are minimised.

The observed effect of increased permeability of tumour vasculature caused by TNF occurs both in the tumour vasculature of tumours found in the body's periphery and also in the tumour vasculature that is present in brain tumours. It is thus possible to increase the permeability of all tumour vasculature by systemic delivery of TNF. The fact that permeability of tumour vasculature behind or beyond the intact BBB (e.g. in the brain) is induced following systemic administration of TNF demonstrates that it is possible to induce the permeability of the intact BBB. Thus, administration of TNF allows the methods of treating or detecting and imaging tumours discussed above to be applied to tumours that are located behind or beyond the BBB, which was previously very difficult.

It is well-known in the art that high doses of systemic TNF are associated with severe toxicity. Phase I studies have reported a maximum tolerable dose (MTD) for TNF in humans of around 200 μg/m$^2$ to 300 μg/m$^2$. TNF has previously been demonstrated to have cytotoxic effects, and to stimulate tumour regression. However, this was only seen in mice at a concentration 10-fold higher than the MTD for TNF in humans. Indeed, TNF is now used to treat tumours in isolated limb perfusions (ILP) at concentrations where the TNF is cytotoxic to the tumours, but too high to be tolerated systemically.

The permeabilising effects resulting from the administration of TNF have been demonstrated at levels much lower than the levels which have previously been suggested for use in the treatment of peripheral tumours, based on the cytotoxic effect of TNF. However, although it has been shown that the permeabilising effect can be induced using doses of
TNF that do not exceed the MTD, it is still in some cases
necessary to administer relatively significant doses of TNF
in order to obtain the desired tumour vasculature permea-
bilization, and thus there is still a risk of adverse side effects.
The downstream effects of TNF are mediated through bind-
ing to two receptors, Tumour Necrosis Factor Receptor 1
(TNFR1) and Tumour Necrosis Factor Receptor 2 (TNFR2).
Both of these receptors bind TNF with similar affinities, but
they are regulated independently from each other, and are
responsible for different functions. Notably, the cytotoxic
effects and tumour vasculature permeabilization effects are
thought to be mediated via TNFR1. The aforementioned
adverse side effects, including severe toxicity, that are com-
monly observed when TNF is administered in significant
doses had previously been thought to be associated with the
binding of TNF to TNFR2. However, it is now believed that
the side effects may be caused by the synergistic activation
of both TNFR1 and TNFR2.

Accordingly, there is a need and a desire to produce TNF
muteins that have advantageous therapeutic effects, e.g. TNF
muteins that can stimulate tumour vasculature permeabili-
zation, without inducing severe adverse side effects. In
particular, it is desirable to produce biologically active TNF
muteins, which exhibit binding to TNFR1 and little or no
binding to TNFR2, when compared with native (wild-type)
TNF. In other words, it is desirable to produce TNF muteins,
which exhibit selective binding for TNFR1, i.e. TNF
muteins that are selective TNFR1 agonists. TNF muteins
that can stimulate tumour vasculature permeabilization at
low doses are particularly desirable.

TNF muteins that bind selectively to one of the TNF
receptors have been described. For instance, Loetscher et al.
(1993, J. Biol. Chem. vol. 268(35), pp. 26350-26357),
identified a human TNF variant having mutations R32W and
S86T relative to wild-type TNF, which showed selective
binding to human TNFR1 (hTNFR1) and no binding to
human TNFR2 (hTNFR2). However, the TNF mutein was
less biologically active than wild-type TNF. Moreover, the
TNF mutein did not bind to murine TNFR1 (mTNFR1), a
property associated with wild-type human TNF. Human
TNF muteins that bind to both human and murine TNFR1
are desirable because they can be used and validated in
mouse-based in vitro and in vivo assays. Moreover, animal
toxicology assessments of therapeutic molecules that are
biologically active in the test animal are more predictive of
effects in humans.

Shibata et al. (2008, J. Biol. Chem. vol. 283(2), pp.
998-1007) describe a TNF mutein that selectively binds to
human TNFR1 with an affinity that is similar to wild-type
TNF. However, the TNF mutein did not activate TNFR1-
mediated responses and functioned as a TNFR1 antagonist.

As discussed in detail in the Examples below, the present
inventors used phage display libraries and several rounds of
selection to identify several human TNF muteins that bind
and activate both human and murine TNFR1, whilst show-
ing no or very little binding to human (or mouse) TNFR2.
Surprisingly, the inventors determined that TNF muteins
with highly desirable characteristics could be generated by
introducing substitutions within a single domain of TNF
corresponding to residues 84-89 of human TNF. The TNF
muteins having a motif of the invention within the domain
also had several other desirable characteristics including
high solubility and expression, biological activity equivalent
to or higher than wild-type TNF (e.g. TNFR1-mediated
responses), low immunogenicity, a half-life similar to wild-
type TNF and good long-term stability.

Thus, at its broadest, the invention provides a TNF mutein
that is an agonist of TNFR1 and binds selectively to TNFR1,
i.e. a selective TNFR1 agonist. In particular, the TNF mutein
of the invention is functionally equivalent to wild-type TNF,
i.e. the TNF mutein activates TNFR1-mediated responses
with the same or similar efficacy as wild-type TNF, i.e. the
TNF mutein elicits TNFR1-mediated responses that are
equivalent to or higher than wild-type TNF at the same or
similar concentration. In some embodiments, the TNF
mutein is a human TNF mutein (i.e. derived from human
TNF, SEQ ID NO: 1) and is functionally equivalent to
human TNF with respect to TNFR1-mediated responses. In
some embodiments, the human TNF mutein binds selec-
tively to human and murine TNFR1.

Thus, in one aspect, the present invention provides a
tumour necrosis factor (TNF) mutein which comprises at
least 4 amino acid mutations compared to a wild-type TNF
sequence, wherein said mutations comprise:
   (a) a substitution of the residue at the position equivalent
      to position 84 of SEQ ID NO. 1;
   (b) a substitution of the residue at the position equivalent
      to position 85 of SEQ ID NO. 1,
   (c) a substitution of the residue at the position equivalent
      to position 88 of SEQ ID NO. 1; and
   (d) a substitution of the residue at the position equivalent
      to position 89 of SEQ ID NO. 1,
   wherein the mutein is an agonist of tumour necrosis factor
      receptor 1 (TNFR1) and binds selectively to TNFR1.

The term "mutein" refers to a polypeptide with an altered
amino acid sequence, i.e. a polypeptide comprising one or
more amino acid mutations relative to a reference amino
acid sequence, e.g. a wild-type amino acid sequence. Thus,
the invention encompasses mutant forms of TNF polypep-
tides (referred to herein as muteins, homologues or variants)
which are structurally similar to their corresponding wild-
type polypeptide (e.g. SEQ ID NO: 1, which is the amino
acid sequence for human TNF) and are able to function as
an agonist of TNFR1. The TNF muteins of the invention also
selectively bind to TNFR1.

The term "mutation" refers to amino acid substitutions,
insertions or deletions. In preferred embodiments, the TNF
muteins of the invention comprise substitutions relative to
the equivalent wild-type amino acid sequence. However, in
some embodiments, the TNF muteins may comprise a
mixture of substitutions and insertions and/or deletions. In
cases where a TNF mutein comprises deletions or insertions
relative to the equivalent wild-type TNF amino acid
sequence, the residues specified herein are present at equiva-
lent amino acid positions in the TNF mutein sequence. In a
preferred embodiment, deletions in the TNF muteins of the
invention are N-terminal and/or C-terminal truncations.

A TNF mutein according to the present invention com-
prises at least 4 amino acid substitutions relative to a
wild-type TNF amino acid sequence. "Wild-type TNF
amino acid sequence" in this context refers to an unmodified
TNF sequence. This may be, for example, human TNF,
mouse TNF, rat TNF, or an unmodified TNF sequence from
any other appropriate source. In a preferred embodiment, the
wild-type sequence that the TNF mutein is based upon may
be the unmodified sequence of human TNF (SEQ ID NO: 1).

Thus, where the TNF mutein is a human TNF mutein, i.e.
a variant of the wild-type human TNF amino acid sequence,
the mutein comprises substitutions of the alanine, valine,
glutamine and threonine residues at positions 84, 85, 88 and
89 of SEQ ID NO: 1, respectively.

The TNF mutein of the invention is an agonist of TNFR1,
meaning that it is an agonist of the TNFR1 derived from the same source as the corresponding wild-type TNF (i.e. the wild-type TNF on which the mutein is based). Thus, if the TNF mutein is a human TNF mutein, i.e. derived from or based on human TNF (SEQ ID NO: 1), it must be an agonist of human TNFR1. In some embodiments, the TNF mutein may be an agonist of more than one TNFR1, e.g. an agonist of the TNFR1 from the same source as the wild-type TNF and an agonist of TNFR1 from a different source to the wild-type TNF.

In this respect, murine models are commonly used to assess the function of therapeutic molecules. For instance, murine models may be used to assess the tumour vasculature permeabilization of the TNF muteins of the invention. Thus, TNF muteins of the present invention were selected to exhibit sufficient binding to murine TNFR1 to enable validation of their ability to trigger tumour vasculature permeabilization in mouse-based assays. Accordingly, in some embodiments, the TNF mutein is a human TNF mutein that is an agonist for both human TNFR1 and murine TNFR1. In some embodiments, the human TNF muteins of the present invention may bind to murine TNFR1 with equivalent (e.g. similar) affinity to that of wild-type human TNF. In further embodiments, the TNF muteins of the present invention may bind to murine TNFR1 with greater affinity to that of wild-type human TNF.

The term "agonist" is a molecule (e.g. polypeptide) that interacts with a target (e.g. receptor) to cause or promote an increase in the activation of the target (e.g. the initiation of a receptor molecule signal cascade). Thus, a TNFR1 agonist is a molecule that interacts with (binds to) TNFR1 and elicits a TNFR1-mediated response, e.g. a response that is specifically associated with the activation of TNFR1.

A TNFR1-mediated response refers to a cellular response that results from intracellular signalling initiated by the activation of TNFR1. In particular, activation of TNFR1 by TNF leads to the recruitment of the adaptor protein TRADD to its cytoplasmic death domain and induction of apoptosis (via activation of caspase-8/10 and caspase 3/7). Thus, a TNFR-1 mediated response may be measured by assessing the cytotoxic effects of the TNF mutein using any suitable assay known in the art, such as the assay described in the Examples.

In addition to functioning as an agonist of TNFR1, a TNF mutein of the invention must bind selectively to TNFR1. The term "bind selectively" refers to the ability of the TNF mutein (in its appropriate quaternary form, e.g. a homotrimer) to bind non-covalently (e.g. by van der Waals forces and/or hydrogen-bonding) to its corresponding TNFR1 with greater affinity and/or specificity than to any other cognate receptor, particularly TNFR2. Thus, for instance, a human TNF mutein of the invention binds to human TNFR1 with greater affinity and/or specificity than to human TNFR2, preferably any TNFR2, i.e. TNFR2 from any source, e.g. murine TNFR2. Moreover, in some preferred embodiments, a human TNF mutein of the invention binds to human TNFR1 with greater affinity and/or specificity than to murine TNFR1. The binding of the TNF mutein to its cognate receptors may be determined using any suitable method known in the art and as described in detail in the Examples. Moreover, the binding is determined using the same conditions for each cognate receptor.

The term "cognate receptor" refers to any receptor to which the wild-type TNF, from which the TNF mutein is derived, is able to specifically bind. For instance, wild-type human TNF binds to human TNFR1, human TNFR2 and murine TNFR1, but does not bind to murine TNFR2. Thus, cognate receptors for human wild-type TNF include human TNFR1, human TNFR2 and murine TNFR1, but do not include murine TNFR2. In other words, murine TNFR2 is not a cognate receptor for human wild-type TNF.

TNFR-1 is alternatively known as TNFRSF1A, CD120a, p55TNFR, TNF-R55, p60, TNF-R-I, TNFAR and TNFRβ.

TNFR-2 is alternatively known as TNFRSF1B, CD120b, p75TNFR, TNF-R75, p80, TNF-R-II, TNFBR and TNFRα.

Binding to the cognate receptors may be distinguished from binding to other molecules (e.g. peptides or polypeptides), so-called non-cognate molecules (e.g. non-cognate TNF receptors, such as TNF receptors from other animals). The TNF mutein of the invention either does not bind to non-cognate molecules or does so negligibly or non-detectably that any such non-specific binding, if it occurs, readily may be distinguished from binding to TNFR1, i.e. the TNFR1 corresponding to the source of the TNF mutein.

In particular, if the TNF mutein of the invention binds to molecules other than its cognate TNFR1 molecules (e.g. TNFR2 molecules), such binding must be transient and the binding affinity must be less than the binding affinity of the TNF mutein for a cognate receptor (i.e. TNFR1). Thus, the binding affinity of the TNF mutein for a cognate TNFR1 molecule should be at least an order of magnitude more than the other molecules (e.g. non-cognate molecules), particularly TNFR2. Preferably, the binding affinity of the TNF mutein for the cognate TNFR1 should be at least 2, 3, 4, 5, or 6 orders of magnitude more than the binding affinity for cognate TNFR2 and other non-cognate molecules (e.g. peptides or polypeptides).

Thus, selective or specific binding refers to affinity of the TNF mutein of the invention for its corresponding TNFR1 (the TNFR1 from the same source as the wild-type TNF on which the mutein is based) where the dissociation constant is less than about $10^{-9}$ M. In a preferred embodiment the dissociation constant of the TNF mutein of the invention for its corresponding TNFR1 is less than about $9.0 \times 10^{-10}$ M, $8.5 \times 10^{-10}$ M, $8.0 \times 10^{-10}$ M, $7.5 \times 10^{-10}$ M, $7.0 \times 10^{-10}$ M or $6.5 \times 10^{-10}$ M. In some preferred embodiments, the dissociation constant of the TNF mutein of the invention for its corresponding TNFR1 may be less than about $5.0 \times 10^{-10}$ M, $4.0 \times 10^{-10}$ M, $3.0 \times 10^{-10}$ M, $2.0 \times 10^{-10}$ M, $1.0 \times 10^{-10}$ M, e.g. less than $9.0 \times 10^{-11}$ M, $8.0 \times 10^{-11}$ M, $7.0 \times 10^{-11}$ M, $6.0 \times 10^{-11}$ M, $5.0 \times 10^{-11}$ M, $4.0 \times 10^{-11}$ M, $3.0 \times 10^{-11}$ M, $2.0 \times 10^{-11}$ M or $1.0 \times 10^{-11}$ M. The dissociation constant may be determined using any suitable method known in the art. In some preferred embodiments, the dissociation constant is determined using a method described in the Examples.

Accordingly, in some embodiments the TNF mutein of the invention binds to its corresponding TNFR2 (i.e. the TNFR2 from the same source as the TNF mutein) with a dissociation constant of at least $10^{-8}$ M, $10^{-7}$ M, $10^{-6}$ M, $10^{-5}$ M, $10^{-4}$ M or $10^{-3}$ M. In preferred embodiments, TNF mutein of the invention does not bind to its corresponding TNFR2 at detectable levels. A TNF mutein may be considered as not binding to TNFR2 if no obvious binding can be observed, or if no binding above background interactions can be observed, e.g. using the binding methods disclosed herein.

Thus, in some embodiments, the TNF mutein may bind to its corresponding TNFR1 with an affinity (Kd) of 1 pM-1 nM, e.g. 5 pM-0.75 nM, 6 pM-0.5 nM, 7 pM-0.3 nM, such as 1-500 pM, 1-400 pM, 5-250 pM, or 10-100 pM, as measured by the assays set out below.

In some embodiments, the TNF mutein may bind to a cognate TNFR1 from another source (e.g. a human TNF mutein may bind to murine TNFR1) with an affinity as described above. In some embodiments, TNF mutein may bind to a cognate TNFR1 from another source (e.g. a human TNF mutein may bind to murine TNFR1) with less affinity than it binds to its corresponding TNFR1. For instance, in some embodiments the TNF mutein may bind to a cognate TNFR1 from another source with about 5-90% of the affinity of the TNF mutein for its corresponding TNFR1, e.g. about 10-80%, 15-75%, 20-70%, 25-65%, such as about 30-60% of the affinity of the TNF mutein for its corresponding TNFR1.

Alternatively viewed, the TNF mutein of the invention is not an agonist of its corresponding TNFR2 (i.e. the TNFR2 from the same source as the TNF mutein). Thus, in some embodiments, the TNF mutein does not bind to its corresponding TNFR2 with sufficient affinity to activate the receptor to promote a TNFR2-mediated response, e.g. a response that is specifically associated with the activation of TNFR2.

As noted above, TNF muteins that exhibit minimal or no binding to and/or activation of their corresponding TNFR2 are expected to avoid significant cytotoxic side effects when administered to patients as the cytotoxic effects are believed to be mediated by the synergistic activation of TNFR1 and TNFR2.

In some embodiments, the TNF mutein of the invention is functionally-equivalent to wild-type TNF with respect to its ability to activate TNFR1. In other words, the TNF mutein of the invention activates TNFR1-mediated responses with the same or similar efficacy as wild-type TNF The same of similar efficacy as wild-type TNF means that the TNF mutein activates TNFR1-mediated responses to a level of at least 70% of the level activated by wild-type TNF. For instance, in the cytotoxicity assays described in the Examples, the TNF mutein is able to kill at least 70% of the cells (e.g. HEp2 cells) killed by wild-type TNF under the same conditions. In some embodiments, the TNF mutein activates TNFR1-mediated responses to a level of at least 75%, 80%, 85% or 90% of the level activated by wild-type TNF. In some embodiments, the TNF mutein is as active or more active than wild-type TNF, e.g. the TNF mutein activates TNFR1-mediated responses to a level of 100% or more of the level activated by wild-type TNF, e.g. 105%, 110%, 115%, 120% or more.

As noted above, the inventors have unexpectedly determined that TNF muteins that selectively agonise TNFR1 may be obtained by substituting amino acid residues in the domain corresponding to residues 84-89 of SEQ ID NO: 1. Thus, in some embodiments, the mutein may further comprise a substitution of the residue at the position equivalent to position 86 of SEQ ID NO. 1.

Thus, the TNF mutein of the invention comprises four or more amino acid mutations compared to a wild-type TNF sequence. These mutations may comprise substitutions at amino acid residue positions equivalent to positions 84, 85, 86, 88 and 89 of SEQ ID NO: 1. Thus, the wild-type amino acid residues found at positions 84, 85, 86, 88 and 89 (or the equivalent positions) may be substituted with any other natural or non-natural (non-coded) amino acid residue. Isomers of the native L-amino acids, e.g. D-amino acids may be incorporated.

The terms "non-natural" or "non-coded" amino acids refer to amino acids which possess a side chain that is not coded for by the standard genetic code.

Further examples of non-natural or structural analogue amino acids which may be used are amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids. Examples of non-coded amino acids are listed in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |

TABLE 1-continued

| Non-conventional amino acid | Code | Non-conventional amino acid | Code |
|---|---|---|---|
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamyl-methyl)glycine | Nnbhm | N-(N-(3,3-diphenylpropyl)carbamyl-methyl)glycine | Nnbhe |
| 1-carboxy-1-(2,2-diphenyl-ethylamino)cyclopropane | Nmbc | L-O-methyl serine | Omser |
| | | L-O-methyl homoserine | Omhse |

Further non-standard amino acids which may be used include conformationally restricted analogs, e.g. such as Tic (to replace F), Aib (to replace A) or pipecolic acid (to replace Pro).

In a preferred embodiment, the amino acids substituted in the TNF mutein are replaced with a natural (coded) amino acid residue. In a particular embodiment, at least the amino acids found at positions 84-89 of SEQ ID NO: 1 (or the equivalent positions), if substituted, are substituted with a natural amino acid residue.

In some embodiments, the substitutions that are present in the TNF mutein of the present invention are conservative amino acid substitutions. A conservative amino acid substitution refers to the replacement of an amino acid by another which preserves the physiochemical character of the polypeptide (e.g. D may be replaced by E or vice versa, N by Q, or L or I by V or vice versa). Thus, generally the substituting amino acid has similar properties, e.g. hydrophobicity, hydrophilicity, electronegativity, bulky side chains etc. to the amino acid being replaced. In a preferred embodiment, substitutions in the TNF mutein of the invention outside of the domain corresponding to residues 84-89 of SEQ ID NO: 1 are conservative substitutions. In some embodiments, substitutions in the domain corresponding to residues 84-89 of SEQ ID NO: 1 are non-conservative substitutions. In particular, substitutions at positions corresponding to 84, 85, 87, 88 and/or 89 may be non-conservative substitutions.

In some embodiments, the amino acid residue at the position equivalent to position 84 of SEQ ID NO: 1 may be substituted by a polar amino acid. In some embodiments, the amino acid residue at the position equivalent to position 84 of SEQ ID NO: 1 may be substituted by serine or threonine or a functionally equivalent non-coded polar amino acid. In some embodiments, the amino acid residue at the position equivalent to position 84 of SEQ ID NO: 1 is substituted by serine or threonine, preferable serine.

In some embodiments, the amino acid residue at the position equivalent to position 85 of SEQ ID NO: 1 may be substituted by a polar amino acid, a hydrophobic amino acid, an acidic amino acid, an amino acid with a small side group, an amino acid with an amine-containing side group or a basic amino acid. In some embodiments, the amino acid residue at the position equivalent to position 85 of SEQ ID NO: 1 may be substituted by alanine, glycine, serine, threonine, glutamic acid, aspartic acid, histidine, isoleucine, leucine, methionine, glutamine or a functionally equivalent non-coded amino acid. In some embodiments, the amino acid residue at the position equivalent to position 85 of SEQ ID NO: 1 may be substituted by alanine, glycine, serine, threonine, glutamic acid, histidine or glutamine. In some embodiments, the amino acid residue at the position equivalent to position 85 of SEQ ID NO: 1 may be substituted by alanine, glycine, serine, threonine or glutamic acid, preferably glycine, serine, threonine or glutamic acid.

In some embodiments, the amino acid residue at the position equivalent to position 86 of SEQ ID NO: 1 may be substituted by a polar amino acid, preferably threonine or a functionally equivalent non-coded polar amino acid. In a preferred embodiment, the amino acid residue at the position equivalent to position 86 of SEQ ID NO: 1 is substituted by threonine.

In some embodiments, the amino acid residue at the position equivalent to position 88 of SEQ ID NO: 1 may be substituted by a polar amino acid, a hydrophobic amino acid, an acidic amino acid, a basic amino acid or an amino acid with an amine-containing side group. In some embodiments, the amino acid residue at the position equivalent to position 88 of SEQ ID NO: 1 may be substituted by a serine, valine, arginine, asparagine, aspartic acid, glutamic acid, isoleucine, methionine, threonine or a functionally equivalent non-coded amino acid. In some embodiments, the amino acid residue at the position equivalent to position 88 of SEQ ID NO: 1 may be substituted by serine, valine, arginine, asparagine, aspartic acid or glutamic acid, preferably serine, valine, arginine or asparagine. In some embodiments, the position equivalent to position 88 of SEQ ID NO: 1 is substituted by asparagine.

In some embodiments, the amino acid residue at the position equivalent to position 89 of SEQ ID NO: 1 may be substituted by a hydrophobic amino acid, an acidic amino acid, an amino acid with a small side group, or an aromatic amino acid. In some embodiments, the amino acid residue at the position equivalent to position 89 of SEQ ID NO: 1 may be substituted by glycine, alanine, aspartic acid, glutamic acid, tyrosine, phenylalanine, tryptophan, leucine, isoleucine, valine, methionine, proline or a functionally equivalent non-coded amino acid. In some embodiments, the amino acid residue at the position equivalent to position 89 of SEQ ID NO: 1 may be substituted by glycine, aspartic acid, tyrosine, leucine or proline. In some embodiments, the amino acid residue at the position equivalent to position 89 of SEQ ID NO: 1 may be substituted by aspartate, tyrosine or proline, preferably proline.

The TNF muteins of the present invention may comprise mutations in addition to those specified above. In some embodiments, the TNF mutein may comprise a substitution at the position equivalent to position 87 of SEQ ID NO: 1. For example, in some embodiments, the amino acid residue at the position equivalent to position 87 of SEQ ID NO: 1 may be substituted by valine, histidine or a functionally equivalent non-coded amino acid. In alternative embodiments, the amino acid residue at the position equivalent to position 87 of SEQ ID NO: 1 is not substituted. Accordingly, in some embodiments (such as where the TNF mutein is based on the sequence of human TNF), the amino acid residue at the position equivalent to position 87 of SEQ ID NO: 1 of the TNF mutein is tyrosine.

The skilled person will understand the meaning of the terms "polar amino acid", "hydrophobic amino acid", "acidic amino acid", "basic amino acid", "amino acid with an amine-containing side group", "aromatic amino acid" and "amino acid with a small side group". The protonation, and therefore the charge, of individual amino acid side chains may depend on the pH at which they are measured. In the present case, a physiological pH is assumed. Polar amino acids may include S, T and C. Hydrophobic amino acids may include I, L, M, V and P. Basic amino acids include R, K and H. Acidic amino acids include D and E. Amino acids with an amine-containing side group include Q and N. Aromatic amino acids include Y, F and W. Amino acids with a small side group include G and A.

As described in detail in the Examples, the present inventors devised a selection process to obtain TNF muteins with binding and agonist properties as described above and other desirable properties, such as low immunogenicity, a half-life similar to wild-type TNF, long term stability in storage. The top 10 ranked TNF muteins with the required properties were selected and their sequences were identified. The sequences of which are set out in SEQ ID NOs: 2 to 11 and the table below shows the sequences of the muteins at positions equivalent to positions 84 to 89 of SEQ ID NO: 1.

TABLE 2

| | TNF Muteins | |
|---|---|---|
| SEQ ID NO | Candidate ID | Sequence at positions corresponding to positions 84-89 of SEQ ID NO: 1 |
| 2 | G4 | SSTYNP (SEQ ID NO: 12) |
| 3 | B5 | TGTYVD (SEQ ID NO: 13) |
| 4 | B6 | TGTYSY (SEQ ID NO: 14) |
| 5 | F3 | TTTYRL (SEQ ID NO: 15) |
| 6 | F7 | SETVVG (SEQ ID NO: 16) |
| 7 | B2 | TASYSG (SEQ ID NO: 17) |
| 8 | B4 | SESHDG (SEQ ID NO: 18) |
| 9 | C4 | SHSVEG (SEQ ID NO: 19) |
| 10 | C8 | SQTHDG (SEQ ID NO: 20) |
| 11 | C9 | AVTYQT (SEQ ID NO: 21) |

Analysis of the sequences in Table 2 has allowed for the construction of motif sequences which are associated with TNF muteins comprising the desired properties discussed above.

In addition to the precise residues present at positions equivalent to positions 84 to 89 of SEQ ID NO: 1 in the 10 lead TNF muteins, it will be understood that residues which represent conservative amino acid substitutions of these residues may also result in muteins with the required binding and agonist properties. As noted above, a conservative amino acid substitution involves the replacement of a given amino acid with another amino acid which has similar properties, e.g. hydrophobicity, hydrophilicity, electronegativity, bulky side chains etc. to the amino acid being replaced. Such a substitution therefore preserves the physiochemical character of the polypeptide. For example, where a mutation from the wild-type residue to a D is observed in the TNF muteins shown above, it may be contemplated that this residue could also be mutated to an E, or vice versa. Similarly, if a TNF mutein comprises a mutation from a wild-type residue to an L, the residue at this position could also be mutated to an I, a V, or an M, or vice versa. Further potential conservative substitutions include; A for G; F or W for Y; S for T; Q for N; and K for R or H. It will be understood that these substitutions are not unidirectional, that is to say they could be implemented in any direction, i.e. each of F, W or Y could be replaced by any other residue selected from the group consisting of F, W and Y.

Accordingly, in one aspect, the TNF mutein of the present invention comprises an amino acid sequence from the motif [S/T]-[A/G/S/T/E/H/Q/D/I/L/M]-[S/T]-[Y/V/H]-[S/V/R/N/D/E/I/L/M/T]-[G/D/Y/L/P/E/A/V/I/M/F/W] (SEQ ID NO: 22) at positions equivalent to positions 84 to 89 of SEQ ID NO: 1.

In a further embodiment, the TNF mutein of the present invention comprises an amino acid sequence from the motif [S/T]-[A/G/S/T/E/H/Q]-[S/T]-[Y/V/H]-[S/V/R/N/D/E]-[G/D/Y/L/P] (SEQ ID NO: 23) at positions equivalent to positions 84 to 89 of SEQ ID NO: 1.

In a further embodiment, the TNF mutein of the present invention comprises an amino acid sequence from the motif [S/T]-[A/G/S/T/E]-[S/THY/VHS/V/R/N]-[G/D/Y/L/P] (SEQ ID NO: 24) at positions equivalent to positions 84 to 89 of SEQ ID NO: 1.

In a further embodiment, the TNF mutein of the present invention comprises an amino acid sequence from the motif [S/T]-[G/S/T/E]-T-[Y/V]-[S/V/R/N]-[G/D/Y/L/P] (SEQ ID NO: 25) at positions equivalent to positions 84 to 89 of SEQ ID NO: 1.

In a further embodiment, the TNF mutein of the present invention comprises an amino acid sequence from the motif [S/T]-[G/S/T]-T-Y-[S/V/R/N]-[D/Y/L/P] (SEQ ID NO: 26) at positions equivalent to positions 84 to 89 of SEQ ID NO: 1.

In a further embodiment, the TNF mutein of the present invention comprises an amino acid sequence from the motif [S/T]-[G/S]-T-Y-[S/V/N]-[D/Y/P] (SEQ ID NO: 27) at positions equivalent to positions 84 to 89 of SEQ ID NO: 1.

In a preferred embodiment, the TNF mutein of the present invention comprises an amino acid sequence selected from one of SEQ ID NOs: 12-20 at positions equivalent to positions 84 to 89 of SEQ ID NO: 1.

In a particularly preferred embodiment, the TNF mutein of the present invention comprises an amino acid sequence selected from one of SEQ ID NOs: 12-17 at positions equivalent to positions 84 to 89 of SEQ ID NO: 1

In a further preferred embodiment, the TNF mutein of the present invention comprises the amino acid sequence selected from one of SEQ ID NOs: 12-15 (preferably SEQ ID NO: 12) at positions equivalent to positions 84 to 89 of SEQ ID NO: 1.

In some embodiments, a TNF mutein of the invention may differ from the corresponding wild-type TNF by, for example, 4 to 50, 4 to 45, 4 to 40, 4 to 35, 4 to 30, 4 to 25, 4 to 20, 4 to 15, 4 to 10, 4 to 8, 4 to 6, e.g. 5 or 6 amino acid substitutions, insertions and/or deletions, preferably substitutions. In some preferred embodiments, the TNF mutein of the invention may differ from the corresponding wild-type TNF by 4 to 20, 5 to 15 or 6 to 10 amino acid substitutions. In some embodiments, the TNF mutein additionally comprises 1 to 30, 1 to 25, 1 to 20, 1 to 15, 1 to 10, 1 to 8, 1 to 6, 1 to 5, 1 to 4, e.g. 1, 2 or 3 amino acid deletions or insertions. In preferred embodiments, the substitutions in positions other than positions equivalent to positions 84-89 of SEQ ID NO: 1 are conservative substitutions.

Thus, in some embodiments, the TNF mutein of the present invention comprises an amino acid sequence having at least 70% sequence identity to the amino acid sequence of any one of SEQ ID NOs: 2 to 10 (preferably SEQ ID NOs: 2 to 7), wherein the mutein contains a sequence at positions corresponding to positions 84-89 of SEQ ID NO: 1 selected from any one of SEQ ID NOs: 22-27, preferably SEQ ID NOs: 12-20, e.g. SEQ ID NOs: 12-17, and wherein the TNF mutein satisfies the functional requirements set out above, i.e. is an agonist of TNFR1 and selectively binds to TNFR1.

More particularly, the TNF mutein of the present invention may comprise a sequence having at least 75, 80, 85, 90, 95, 96, 97, 98 or 99% sequence identity to any one of SEQ ID NOs: 2 to 10 (preferably SEQ ID NOs: 2 to 7), wherein the mutein contains a sequence at positions corresponding to positions 84-89 of SEQ ID NO: 1 selected from any one of SEQ ID NOs: 22-27, preferably SEQ ID NOs: 12-20, e.g. SEQ ID NOs: 12-17, and wherein the TNF mutein satisfies the functional requirements set out above.

Sequence identity may be determined by any suitable means known in the art, e.g. using the SWISS-PROT protein sequence databank using FASTA pep-cmp with a variable pamfactor, and gap creation penalty set at 12.0 and gap extension penalty set at 4.0, and a window of 2 amino acids. Other programs for determining amino acid sequence identity include the BestFit program of the Genetics Computer Group (GCG) Version 10 Software package from the University of Wisconsin. The program uses the local homology algorithm of Smith and Waterman with the default values: Gap creation penalty—8, Gap extension penalty=2, Average match=2.912, Average mismatch=−2.003.

Preferably said comparison is made over the full length of the sequence, but may be made over a smaller window of comparison, e.g. less than 150, 120, 100, 80 or 50 contiguous amino acids.

Accordingly, in some embodiments the TNF mutein of the invention comprises an amino acid sequence with at least 70% (e.g. at least 75, 80, 85, 90 or 95%) sequence identity to a sequence as set forth in SEQ ID NO: 28, wherein said amino acid sequence comprises:

1) an amino acid selected from S and T at position 84;
2) an amino acid selected from A, G, S, T, E, H, Q, D, I, L and M at position 85;
3) an amino acid selected from S and T at position 86;
4) an amino acid selected from Y, V and H at position 87;
5) an amino acid selected from S, V, R, N, D, E, I, L, M and T at position 88; 6) an amino acid selected from G, D, Y, L, P, E, A, V, I, M, F and W at position 89;
wherein the specified amino acid residues are at positions equivalent to the positions in SEQ ID NO: 1 or SEQ ID NO: 28.

In some embodiments, the TNF mutein comprises the preferred amino acids at the specified positions as defined above (i.e. amino acids as defined in SEQ ID NOs: 23-27, preferably SEQ ID NOs: 12-20, e.g. SEQ ID NOs: 12-17).

In some embodiments, the TNF mutein may comprise a substitution at a position equivalent to position 2 of SEQ ID NO: 1. In some embodiments, the substitution is a conservative substitution. In some preferred embodiments, the TNF mutein comprises a histidine at a position equivalent to position 2 of SEQ ID NO: 1.

In some embodiments, the TNF mutein may comprise a substitution at a position equivalent to position 134 of SEQ ID NO: 1. In some embodiments, the substitution is a conservative substitution. In some preferred embodiments, the TNF mutein comprises a valine at a position equivalent to position 134 of SEQ ID NO: 1.

In some embodiments, the TNF mutein may comprise a substitution at a position equivalent to position 155 of SEQ ID NO: 1. In some embodiments, the substitution is a conservative substitution. In some preferred embodiments, the TNF mutein comprises a valine at a position equivalent to position 155 of SEQ ID NO: 1.

In some embodiments, the amino acids in the TNF mutein corresponding to positions 29-32 and/or 144-147 of SEQ ID NO: 1 are not substituted. Thus, in some embodiments, the TNF mutein comprises an amino acid sequence of LNRR (SEQ ID NO: 29) at positions equivalent to positions 29-32 of SEQ ID NO: 1 and/or an amino acid sequence of FAES (SEQ ID NO: 30) at positions equivalent to positions 144-147 of SEQ ID NO: 1.

The TNF mutein of the invention does not contain an amino acid sequence of STTHNQ (SEQ ID NO: 31) at positions equivalent to positions 84-89 of SEQ ID NO: 1.

In a particularly preferred embodiment, the TNF mutein comprises an amino acid sequence as set forth in any one of SEQ ID NOs: 2-10, preferably 2-7. In some embodiments, the TNF mutein of the invention comprises an amino acid sequence as set forth in SEQ ID NO: 2.

The variant polypeptides (TNF muteins) described above are functionally equivalent to the TNF muteins exemplified herein, e.g. to TNF muteins having an amino acid sequence as set forth in any one of SEQ ID NOs: 2-10, preferably 2-7, most preferably SEQ ID NO: 2. Notably, the polypeptides of the invention, e.g. with sequences as set forth in the Sequence NOs. may be modified without affecting the sequence of the polypeptide as described below.

As referred to herein, to achieve "functional equivalence" the variant polypeptide may show some reduced efficacy in performing the function relative to the parent molecule (i.e. the molecule from which it was derived, e.g. by amino acid substitution), but preferably is as efficient or is more efficient. Thus, functional equivalence relates to a polypeptide which is effective to act as described herein, e.g. to bind to and agonise a receptor as referred to above and/or permeabilise the tumour vasculature as described below. This may be tested by comparison of the effects of the variant polypeptide relative to the polypeptide from which it is derived in a qualitative or quantitative manner, e.g. by performing the in vivo analyses described in WO 2011/070358 (incorporated herein by reference). Where quantitative results are possible, the variant is at least about 50%, 60%, 70%, 80% or 90% as effective as the parent polypeptide. Alternatively, in vitro testing may be performed, e.g. by analysis of binding to a receptor as referred to above.

Functionally-equivalent polypeptides which are related to or derived from the TNF muteins exemplified herein (i.e. polypeptides having an amino acid sequence as set forth in SEQ ID NOs: 2-10, particularly 2-7) may be obtained by modifying the parent amino acid sequence by single or multiple amino acid substitution, addition and/or deletion (providing they satisfy the above-mentioned sequence identity requirements), but without destroying the molecule's function. Preferably the variant polypeptide has less than 50, 40, 30, 20 substitutions, additions or deletions, e.g. less than 10, 5, 4, 3, 2, or 1 such modifications, relative to its parent molecule.

Functional equivalents may be "addition" variants in which amino and/or carboxy terminal fusion polypeptides are generated, comprising an additional protein or polypeptide fused to the parent polypeptide. They may also be "deletion" variants, in which e.g. 1 to 50, e.g. 1 to 10, 20, 30 or 40, or 5 to 40, e.g. 10 to 35 amino acids are deleted from the N or C terminus or internally, thereby generating a truncated version of the parent polypeptide. As referred to herein such deletion variants preferably comprise at least 100, 120, 130 or more amino acids of the sequence from which it is derived. These amino acids may be obtained from a central or N-terminal or C-terminal portions of the parent sequence. Such deletion variants are also referred to herein as truncated versions or portions of the TNF muteins set forth in SEQ ID NOs: 2-10.

In some embodiments, functionally-equivalent variants include those which are modified without affecting the sequence of the polypeptide, e.g. by chemical modification, including by deglycosylation or glycosylation. Such polypeptides may be prepared by post-synthesis/isolation modification of the polypeptide without affecting functionality, e.g. certain glycosylation, methylation etc. of particular residues.

In a further aspect, the invention provides a nucleic acid molecule encoding a TNF mutein (polypeptide) as defined above.

In some embodiments, the nucleic acid molecule encoding a TNF mutein defined above comprises a nucleotide sequence as set forth in any one of SEQ ID NOs: 32-40 or a nucleotide sequence with at least 80% sequence identity to a sequence as set forth in any one of SEQ ID NOs: 32-40.

Preferably, the nucleic acid molecule above is at least 85, 90, 95, 96, 97, 98, 99 or 100% identical to the sequence to which it is compared.

Nucleic acid sequence identity may be determined by, e.g. FASTA Search using GCG packages, with default values and a variable pamfactor, and gap creation penalty set at 12.0 and gap extension penalty set at 4.0 with a window of 6 nucleotides. Preferably said comparison is made over the full length of the sequence, but may be made over a smaller window of comparison, e.g. less than 400, 300, 200, 100 or 50 contiguous nucleotides.

The nucleic acid molecules of the invention may be made up of ribonucleotides and/or deoxyribonucleotides as well as synthetic residues, e.g. synthetic nucleotides that are capable of participating in Watson-Crick type or analogous base pair interactions. Preferably, the nucleic acid molecule is DNA or RNA.

The nucleic acid molecules described above may be operatively linked to an expression control sequence, or a recombinant DNA cloning vehicle or vector containing such a recombinant DNA molecule. This allows cellular expression of the polypeptides of the invention as a gene product, the expression of which is directed by the gene(s) introduced into cells of interest. Gene expression is directed from a promoter active in the cells of interest and may be inserted in any form of linear or circular nucleic acid (e.g. DNA) vector for incorporation in the genome or for independent replication or transient transfection/expression. Suitable transformation or transfection techniques are well described in the literature. Alternatively, the naked nucleic acid (e.g. DNA or RNA, which may include one or more synthetic residues, e.g. base analogues) molecule may be introduced directly into the cell for the production of polypeptides of the invention. Alternatively the nucleic acid may be converted to mRNA by in vitro transcription and the relevant proteins may be generated by in vitro translation.

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art. Examples of suitable vectors include bacterial and mammalian expression vectors.

In some embodiments, the nucleic acid molecules of the invention are codon-optimised for expression in a host cell, e.g. a bacterial cell such as *E. coli*, or a mammalian cell, such as a human cell line.

The polypeptide of the invention may comprise additional sequences (e.g. peptide tags to facilitate purification of the polypeptide) and thus the nucleic acid molecule may conveniently be fused with DNA encoding an additional peptide, e.g. His-tag, C-tag, Flag-tag, to produce a fusion protein on expression.

Thus viewed from a further aspect, the present invention provides a vector, preferably an expression vector, comprising a nucleic acid molecule as defined above.

Other aspects of the invention include methods for preparing recombinant nucleic acid molecules according to the invention, comprising inserting nucleic acid molecule of the invention encoding the polypeptide (TNF mutein) of the invention into vector nucleic acid.

Nucleic acid molecules of the invention, preferably contained in a vector, may be introduced into a cell by any appropriate means. Suitable transformation or transfection techniques are well described in the literature. Numerous techniques are known and may be used to introduce such vectors into prokaryotic or eukaryotic cells for expression. Preferred host cells for this purpose include insect cell lines, yeast, mammalian cell lines or *E. coli*, such as strain BL21/DE3. The invention also extends to transformed or transfected prokaryotic or eukaryotic host cells containing a nucleic acid molecule, particularly a vector as defined above.

Thus, in another aspect, there is provided a recombinant host cell containing a nucleic acid molecule and/or vector as described above.

By "recombinant" is meant that the nucleic acid molecule and/or vector has been introduced into the host cell. The host cell may or may not naturally contain an endogenous copy of the nucleic acid molecule, but it is recombinant in that an exogenous or further endogenous copy of the nucleic acid molecule and/or vector has been introduced.

A further aspect of the invention provides a method of preparing a polypeptide (TNF mutein) of the invention as hereinbefore defined, which comprises culturing a host cell containing a nucleic acid molecule as defined above, under conditions whereby said nucleic acid molecule encoding said polypeptide (TNF mutein) is expressed and recovering said molecule (polypeptide) thus produced. The expressed polypeptide (TNF mutein) forms a further aspect of the invention.

In some embodiments, the polypeptide (TNF mutein) of the invention, or for use in the method and uses of the invention, may be generated synthetically, e.g. by ligation of amino acids or smaller synthetically generated peptides, or more conveniently by recombinant expression of a nucleic acid molecule encoding said polypeptide as described hereinbefore.

Nucleic acid molecules of the invention may be generated synthetically by any suitable means known in the art.

Thus, the polypeptide (TNF mutein) of the invention may be an isolated, purified, recombinant or synthesised polypeptide.

The term "polypeptide" is used herein interchangeably with the term "protein". The term polypeptide or protein typically includes any amino acid sequence comprising at least 40 consecutive amino acid residues, e.g. at least 50, 60, 70, 80, 90, 100, 150 amino acids, such as 40-1000, 50-900, 60-800, 70-700, 80-600, 90-500, 100-400 amino acids.

Similarly, the nucleic acid molecules of the invention may be an isolated, purified, recombinant or synthesised nucleic acid molecule.

Thus, alternatively viewed, the polypeptides and nucleic acid molecules of the invention preferably are non-native, i.e. non-naturally occurring, molecules.

Standard amino acid nomenclature is used herein. Thus, the full name of an amino acid residue may be used interchangeably with one letter code or three letter abbreviations. For instance, lysine may be substituted with K or Lys, isoleucine may be substituted with I or Ile, and so on. Moreover, the terms aspartate and aspartic acid, and glutamate and glutamic acid are used interchangeably herein and may be replaced with Asp or D, or Glu or E, respectively.

In addition to selecting the ten top ranked TNF muteins described in the Example based on their binding to hTNFR1, hTNFR2 and mTNFR1, the present inventors devised a selection process to obtain muteins with other desirable properties, such as low immunogenicity, a half-life similar to wild-type TNF, long term stability in storage.

In view of the therapeutic utility of the TNF muteins, e.g. in methods of treating and/or detecting tumours, an important consideration is ease of manufacture, and particularly scalability of manufacture. In this regard, it was found that periplasmic extracts from bacteria engineered to express the R32W S86T TNF mutein identified in Loetscher (supra) showed low levels of expression. Accordingly, the TNF muteins were selected for manufacturability by assessing their binding to human TNFR1 using a crude periplasmic extract and selecting TNF muteins that exhibited significant binding to human TNFR1 from a crude periplasmic extract.

Thus, the TNF muteins of the invention are suitable for large scale manufacturing, e.g. express well in a recombinant expression system, e.g. a bacterial (e.g. *E. coli*) expression system, and yield soluble protein. For instance, in some embodiments, the amount of TNF mutein obtained from a suitable expression system (e.g. for large scale manufacturing) is similar to or greater than the amount of the corresponding wild-type TNF obtained using the same system under the same conditions.

Thus, in some embodiments, the amount of TNF mutein obtained from a suitable expression system is at least 35%, such as at least 40%, 50%, 60% or 70% of the amount of the corresponding wild-type TNF obtained using the same system under the same conditions. In some embodiments, the amount of TNF mutein obtained from a suitable expression system is greater than the amount of the corresponding wild-type TNF obtained using the same system under the same conditions, e.g. 1.5, 2, 2.5, 3 or more times the amount of the corresponding wild-type TNF obtained using the same system under the same conditions.

In preferred embodiments, the TNF mutein of the invention has low immunogenicity, i.e. the mutein does not induce or provoke a significant immune response on administration. Thus, in some embodiments, the TNF mutein of the invention does not contain any iTope promiscuous high epitopes and/or contains 4 or fewer, e.g. 3, 2, 1 or 0, iTope promiscuous moderate epitopes. The immunogenicity of the TNF mutein of the invention can be determined using any suitable method, such as the iTope in silico analysis described in the Examples.

In some embodiments, the TNF mutein of the invention has a half-life in plasma that is similar to wild-type TNF, typically about 4-7 minutes. Thus, in some embodiments the TNF mutein of the invention has a half-life in plasma of about 1-20 minutes, such as about 2-15, 3-12 or 4-10 minutes, e.g. about 5-6 minutes. The half-life of a TNF mutein can be determined using any suitable method known in the art, such as the method described in the Examples.

In preferred embodiments, the TNF mutein of the invention has long term stability when frozen, i.e. it shows minimal loss of activity and/or minimal degradation. For instance, the TNF mutein of the invention that has been stored in a frozen state (e.g. at −20° C. or less, e.g. −30° C., −40° C., −50° C., −60° C., −70° C. or less, e.g. −80° C.) for at least about 3 months, e.g. about 6, 9 or 12 months, may retain the binding and agonist activities within the ranges described above.

As noted above, the TNF muteins defined herein are agonists of TNFR1 and it has been shown that the activation of TNFR1 by TNF is responsible for its tumour vasculature permeabilising activity. Accordingly, the TNF mutein of the invention is expected to find utility in permeabilising tumour vasculature to provide improved access for anticancer agents and for signal generating agents to the tumour.

Thus, in a further aspect, the invention provides a TNF mutein as defined above for use in therapy.

In particular, the invention further provides a TNF mutein as hereinbefore defined for use in permeabilising the vasculature of a tumour in a patient for treating, detecting or diagnosing said tumour, wherein said TNF mutein is formulated for systemic administration to a patient.

In view of this permeabilising effect on tumour vasculature, the TNF muteins of the present invention are suitable for treating tumours when used with an appropriate anticancer agent. In particular, the present invention provides a TNF mutein for use in permeabilising the vasculature of a tumour in a patient for treating said tumour, wherein said TNF mutein is formulated for systemic administration with an anticancer agent, or is intended for use with an anticancer agent.

Furthermore, the TNF muteins of the present invention are suitable for the detection of tumours, when used with an appropriate signal generating agent. The present invention thus provides a TNF mutein for use in permeabilising the vasculature of a tumour in a patient for detecting or diagnosing said tumour, wherein said TNF mutein is formulated for systemic administration with a signal generating agent, or is intended for use with a signal generating agent.

TNF is primarily produced in vivo as a type II transmembrane protein arranged in stable homotrimers. The transmembrane homotrimers are subjected to proteolytic cleavage to cause the release of the homotrimeric cytokine. TNF is thus active as a homotrimer.

The TNF mutein sequences of the present invention represent sequences of TNF monomers. Accordingly, the TNF mutein to be used in the methods of the present invention will function as an active molecule made up of a trimer of three molecules having a sequence as hereinbefore defined. In some embodiments, the trimer comprises three molecules comprising the same sequence, i.e. the TNF mutein is a homotrimer. However, it is envisaged that a heterotrimer comprising two or three different TNF mutein sequences as defined herein may find utility in the methods and uses described herein.

The term "vasculature" refers to any part of the circulatory system in an animal, i.e. to a blood vessel, which is any vessel (preferably a tubular vessel) conveying blood. This may be for example an artery, arteriole, vein, capillary or venule. All blood vessels contain endothelial cells.

Solid tumours, like any other tissue, require a functioning vasculature in order for the nutrients that they require for growth to be delivered and for waste products to be removed. If adequate vasculature is not present in the region of a tumour, a growing tumour will thus develop its own vasculature. Such vasculature (which can be described as a vascular network) can be acquired by the tumour at least in part, by the incorporation of existing host blood vessels, but may also involve the formation of new blood vessels, in processes known as angiogenesis and neovascularisation.

Tumour vasculature as referred to herein is thus any vasculature that is found within, in contact with, or associated with (near to or adjacent to) a solid tumour. Vasculature that is within a solid tumour is thus inside the solid tumour, i.e. surrounded by tumour or tumour tissue or cells. Vasculature that is in contact with a solid tumour may be within the tumour and/or may be at the tumour surface or periphery. Vasculature that is associated with a solid tumour may also be within or in contact with the tumour, but it also includes vasculature that is not directly in contact with the solid tumour, but is near to or adjacent to the tumour, e.g. within 10, 5, 3, 2 or 1 mm radius of any cells of the tumour mass. Tumour vasculature can thus be distinguished from normal or non-tumour vasculature on the basis of the location of the vasculature within an individual Tumour vasculature is thus sufficiently close to a tumour such that when said vasculature becomes permeabilised, access of agents present in the blood in said tumour vasculature is improved such that higher concentrations of such agents can reach said tumour.

Tumour vasculature can also be distinguished from normal or non-tumour vasculature on the basis of one or more cellular markers that may or may not be present in the relevant blood vessel e.g. in the cells (e.g. endothelial cells) that make up or form part of the relevant blood vessel. In other words, the proteins and other molecules that are found within and on the surface of the cells that make up the blood vessel may be different in tumour vasculature and normal or non-tumour vasculature. These molecules are referred to herein as tumour vasculature markers and the presence or absence of one or more of these markers or a group of these markers can be used to distinguish tumour vasculature from normal or non-tumour vasculature. Tumour vasculature thus contains a different pattern of markers compared to normal or non-tumour vasculature, or a different expression profile of markers compared to normal or non-tumour vasculature.

Markers that are found in tumour vasculature and not in normal or non-tumour vasculature are thus referred to herein as tumour vasculature makers. Markers that are found at higher levels (e.g. at least 1.1, 1.25, 2, 2.5, 3, 5, 10, 20, 50, 100 or 1000 fold higher levels) in tumour vasculature than in normal or non-tumour vasculature are considered to be tumour vasculature markers. Markers that are found in normal or non-tumour vasculature and not in tumour vasculature are thus referred to herein as normal or non-tumour vasculature makers. Markers that are found at higher levels (e.g. at least 1.1, 1.25, 2, 2.5, 3, 5, 10, 20, 50, 100 or 1000 fold higher levels) in normal or non-tumour vasculature than in tumour vasculature are considered to be normal or non-tumour vasculature markers.

These markers may be proteins, glycoproteins or polypeptides (which may be adhesion molecules, enzymes, receptors, signalling molecules, structural proteins, proteins involved in immune responses, proteins involved in the cell cycle) polysaccharides, nucleic acid molecules, lipids (e.g.

phospholipids, glycolipids or other components of the plasma membrane). Such markers may be found at the surface of the relevant cell (e.g. within, attached to or associated with the cell membrane), or may be found within the relevant cell. Such markers can be detected, and if necessary quantitated using standard techniques that are well known in the art.

For example it has been shown that tumour vasculature in the brain expresses adhesion molecules and receptors which are not expressed by the normal brain endothelium. Whilst these differences may in part account for the different behaviour of tumour vasculature compared to normal or non-tumour vasculature in terms of the observed responses to TNF, they can also be used as a way to distinguish tumour vasculature from normal or non-tumour vasculature.

Examples of molecules that are found in tumour vasculature and not in normal or non-tumour vasculature or at higher levels in tumour vasculature than in normal or non-tumour vasculature (tumour vasculature markers) include adhesion molecules such as vascular cell adhesion molecule-1 (VCAM-1), Inter-Cellular Adhesion Molecule 1 (ICAM) and selectins (e.g. P, E and L selectin) as well as active transport molecules such as the multidrug resistance transporter.

Molecules may also be found in normal or non-tumour vasculature and not in tumour vasculature or at higher levels in normal or non-tumour vasculature than in tumour vasculature (normal or non-tumour vasculature markers).

Thus, as alternatively defined, tumour vasculature is vasculature that expresses one or more of the tumour vasculature markers as defined above (or a group of such markers), or does so at a higher level (a statistically significantly higher level) than normal or non-tumour vasculature. Tumour vasculature can also be defined as vasculature that does not express one or more of the normal or non-tumour vasculature markers as defined above (or a group of such markers), or does so at a lower level (a statistically significantly lower level) than normal or non-tumour vasculature. The presence or absence or level of one of these markers can be used as an indication of whether vasculature is tumour vasculature as defined herein, or alternatively this assessment can be made of the basis of the presence or absence or level of at least 2, 3, 4, 5, 6, 7, 8, 9, 10, 20, 30, 40, 50 or 100 such markers.

As discussed previously, systemic administration of wild-type TNF has been shown by the present inventors to cause a selective and transient increase in permeability of the tumour vasculature, and as such tumour vasculature may also be distinguished from normal or non-tumour vasculature on this basis. Tumour vasculature may therefore be alternatively defined as vasculature which responds to systemic administration of wild-type TNF (or a TNF mutein of the invention) in an individual, by showing increased vascular permeability compared to tumour vasculature in an individual which has not been subjected to systemic administration of TNF or by showing increased permeability compared to normal or non-tumour vasculature in the same individual or in another individual who has been subjected to systemic administration of TNF.

Thus, one utility of the TNF muteins of the invention is for permeabilising tumour vasculature, or alternatively stated to increasing the permeability of tumour vasculature.

Vascular permeability characterizes the capacity of a blood vessel (e.g. the blood vessel wall) to allow for the flow of small molecules (ions, water, nutrients), large molecules (e.g., proteins and nucleic acids) or whole cells in and out of the vessel. This passage of fluid, molecules and cells in and out of blood vessels is regulated in part by cell-cell adhesions between endothelial cells and the endothelial cell monolayer lining the vasculature forms a barrier that maintains the integrity of the blood fluid compartment, but permits passage of soluble factors and leukocytes in a regulated manner. In normal physiological processes, changes (e.g. increases or decreases) in vascular permeability may occur as a precisely regulated function, for example in immune responses and wound healing.

Permeabilising tumour vasculature thus refers to causing an increase in tumour vascular permeability. This means that there is an increase in the number or type of molecules or cells that can move in or out of the relevant blood vessel, i.e. more molecules or cells can move in or out of the relevant blood vessel.

This increase may reflect the fact that the total number of molecules or cells that can move in or out of the relevant blood vessel is increased (i.e. more molecules or cells of all types can move in or out of the relevant blood vessel). Alternatively, the increase may be specific to one type of molecule or cell (e.g. one of small molecules (ions, water, nutrients), large molecules (e.g., proteins and nucleic acids) or whole cells) or to a certain small molecule, ion, nutrient, large molecule, protein, nucleic acid or group thereof. If the increase in permeability is specific to one type of molecule or cell or to a certain small molecule, or group thereof, in that one type of molecule or cell or a certain small molecule, or group thereof can pass more readily through the tumour vasculature than another type of molecule or cell or a certain small molecule, or group thereof, it can be defined as being a selective increase. Such a selective increase may reflect the fact that molecules sharing a certain property (e.g. molecules of a certain charge, size etc.) can move in or out of the relevant blood vessel more readily.

Alternatively or additionally any increase in permeability may reflect not only the number or nature of molecules or cells passing more readily through the tumour vasculature, but may reflect an increase in the number of blood vessels which are becoming permeabilised to the molecules.

As discussed above, the TNF muteins of the invention can be used in methods to increase the access of agents such as signal generating, e.g. imaging, agents and therapeutic, e.g. anticancer, agents to tumours. As such, in one embodiment, the TNF muteins of the invention find utility in increasing the permeability of tumour vasculature to signal generating, e.g. imaging, and therapeutic, e.g. anticancer, agents. Preferably said increase in the permeability of tumour vasculature is selective for said imaging and anticancer agents.

Any increase in the permeability of tumour vasculature is preferably statistically significant. To determine this, to the extent that this can be quantitated, the permeability of tumour vasculature following appropriate systemic treatment with a TNF mutein as defined herein can be determined and compared to the permeability of tumour vasculature in the absence of such treatment, or to the permeability of normal or non-tumour vasculature following appropriate systemic treatment with a TNF mutein. The increases referred to above may be at least 1.1, 1.25, 2, 2.5, 3, 5, 10, or 20 fold.

The permeability of tumour vasculature can be measured functionally by administering an imaging agent as defined herein to an individual and observing the ability of this agent to pass through the tumour vasculature, e.g. by MRI, or by observing the ability of a blood borne or intravascular dye (such as Evans blue or FITC) or a radiolabelled compound (such as inulin or mannitol) to pass through the tumour vasculature in the presence and absence of a TNF mutein. In other words it can readily be determined whether an increase in tumour vascular permeabilisation has occurred following systemic administration of a TNF mutein, based on detecting the effect of the administration of this molecule on the ability of appropriate agents to pass through the tumour vasculature.

Alternatively defined, the process of permeabilising tumour vasculature can be defined as disrupting the integrity of the normal barrier surrounding said tumour vasculature. As discussed above, vasculature contains endothelial cells and it is these endothelial cells which are primarily responsible for controlling the movement of molecules and cells out of the vasculature. There is thus a barrier around all vascular cells and when said barrier around said tumour vasculature is intact, there is limited potential for movement of molecules and cells as referred to above from the vasculature into the tumour (e.g. the tumour in which the relevant blood vessel is found, is in contact with or with which the blood vessel is associated). When the TNF mutein is present systemically, the integrity of the barrier around the tumour vasculature is disrupted and the movement of molecules and cells as referred to above from the vasculature into the tumour can occur more readily or is increased, as discussed above.

When the tumour is in the brain, the barrier as referred to above is the BBB and as such, in a preferred embodiment, the systemic administration of a TNF mutein causes the disruption of the integrity of the BBB.

Accordingly, in some embodiments the present invention provides a TNF mutein for use in permeabilising vasculature of a tumour that is behind an intact BBB. In this regard, in some embodiments the disruption of the integrity of the barrier surrounding the tumour vasculature may include the disruption of the integrity of the BBB of such a tumour.

As discussed above, tumour vasculature has previously been shown to respond differently to normal or non-tumour vasculature when wild-type TNF is systemically administered to an individual, in that the permeability of tumour vasculature is increased whereas that of normal or non-tumour vasculature is not.

Whilst there is preferably no change to the permeability of normal or non-tumour vasculature following systemic administration with a TNF mutein of the invention, some changes to the permeability of normal or non-tumour vasculature following systemic administration with a TNF mutein of the invention would be tolerable, and are not excluded.

In a preferred embodiment therefore the effect of the TNF mutein of the invention is specific to tumour vasculature. By specific it is meant that the permeabilisation effect of the TNF mutein is observed only in tumour vasculature and not in normal or non-tumour vasculature, or that the permeabilisation effect of the TNF mutein is observed to a greater extent in tumour vasculature than in normal or non-tumour vasculature. In other words the effect of the TNF mutein on the permeability of the tumour vasculature is greater than the effect of the TNF mutein on the permeability of normal or non-tumour vasculature. To the extent that this can be quantitated, the effect of the TNF mutein on the permeability of the tumour vasculature is at least 1.1, 1.25, 2, 2.5, 3, 5, 10 or 20 fold greater than the effect of the TNF mutein on the permeability of normal or non-tumour vasculature.

As discussed above, this has the advantages of avoiding generalised increases in vascular permeability which are undesirable.

The permeability of tumour vasculature has previously been shown experimentally in WO 2011/070358 (incorporated herein by reference) to return to normal levels following the discontinuation of the systemic administration of wild-type TNF to an individual.

In a preferred embodiment therefore the permeability of tumour vasculature increases only transiently, temporarily or reversibly following discontinuation of the systemic administration of a TNF mutein to an individual. In other words the permeability of tumour vasculature returns to normal or substantially normal levels after the systemic administration of a TNF mutein to an individual is discontinued, i.e. after the administration of the TNF mutein is stopped, withdrawn or ceased.

A normal level of permeability of tumour vasculature as referred to herein can be the level of permeability of tumour vasculature in the absence of any treatment with a TNF mutein, or the level of permeability of normal or non-tumour vasculature following treatment with a TNF mutein. Substantially normal levels of permeability of tumour vasculature are thus approximately normal levels of tumour vasculature permeability, e.g. 0.9-1.1, 0.95-1.05, 0.975-1.025 fold that of tumour vasculature in the absence of any treatment with a TNF mutein, or of normal or non-tumour vasculature following treatment with a TNF mutein, to the extent that this can be quantitated.

In a preferred embodiment, the TNF mutein is administered at a suitable dosage (e.g. in repeated doses of a suitable amount as discussed elsewhere herein) to sustain permeability of the tumour vasculature for the period in which the therapeutic agent (e.g. anticancer agent) or signal generating (e.g. imaging) agent is present in the circulation of the patient. As the effect of a TNF mutein is transient and the permeability of tumour vasculature may return to substantially normal levels within 48, 36 or 24 hours after the systemic administration of a TNF mutein to an individual is discontinued, withdrawn or ceased, multiple doses of the TNF mutein may be required. For instance, a therapeutic (e.g. anticancer) agent that is retained in a patient system for about 72 hours may require a final dose of the TNF mutein to be administered 24, 36 or 48 hours after the therapeutic agent is administered to ensure it can reach its target site. The skilled person readily could determine a suitable dosage regime based on the characteristics (e.g. half-life) of the therapeutic or signal generating agent to be administered to the patient.

In some embodiments, the permeability of tumour vasculature returns to substantially normal levels within 12-60 or 24-48 hours after the systemic administration of a TNF mutein to an individual is discontinued, withdrawn or ceased.

As discussed above, this has the advantages of avoiding prolonged increases in vascular permeability, which are undesirable. As long as any agent which is desired to reach the tumour is in the vascular system during the period in which the permeability of the tumour vasculature is increased, the agent will be able to pass through the tumour vasculature and reach the tumour to carry out the desired effects.

The TNF mutein may exert its effect on the tumour vasculature when administered systemically to a patient. As such, to achieve the desired effect in accordance with the invention the TNF mutein may be formulated for systemic administration to said patient.

"Systemic administration" refers to administration of a drug or compound to a patient such that it becomes widely distributed in the body in significant amounts and has a biological effect, in the blood. Alternatively stated, the drug or compound reaches its desired site of action via the vascular system. In the present case systemic administration includes any administration which is not directly to the tumour (e.g. intratumoural).

Typical systemic routes of administration include administration by introducing an agent directly into the vascular system (e.g. intravenously (into a vein), intraarterially (into an artery) or intraosseous infusion (into the bone marrow)). These are examples of parenteral routes of administration.

Enteral routes of administration (where the relevant substance is given via the digestive tract) include a pulmonary route, or intramuscular administration wherein the agent is adsorbed, enters the vascular system, and is carried to one or more desired site(s) of action via the blood. Enteral administration may be by mouth (orally), in which case the compound may be administered in the form of a tablet, capsule, or liquid formulation. Alternative enteral routes of administration are by a feeding tube e.g. a gastric, duodenal or gastrostomy feeding tube, or rectal administration (e.g. in suppository or enema form).

To achieve systemic administration, the compositions of the invention may be formulated in a conventional manner with one or more physiologically acceptable carriers, excipients and/or diluents, according to techniques well known in the art using readily available ingredients.

Preferably the TNF mutein is formulated for intravenous administration to said patient.

Thus, in a further aspect the invention provides a pharmaceutical composition comprising a TNF mutein of the invention and one or more conventional (pharmaceutically acceptable) carriers, diluents and/or excipients.

By "pharmaceutically acceptable" or "physiologically acceptable" is meant that the ingredient must be compatible with other ingredients in the composition as well as physiologically acceptable to the recipient.

In some embodiments, the pharmaceutical composition may contain other active substances, e.g. as a combined preparation. Thus, in some embodiments, the invention may be seen as providing a product or kit comprising a TNF mutein as defined herein and another active substance (e.g. an anticancer agent) as a combined preparation for simultaneous, separate or sequential use in therapy. In preferred embodiments, the TNF mutein is formulated for systemic administration to the patient.

Thus, the inventive may be seen to provide a kit comprising a TNF mutein of the invention (or pharmaceutical composition as defined above) and another active substance, e.g. a therapeutic (e.g. anticancer) agent or signal generating (e.g. imaging) agent as defined herein.

The active ingredients for administration may be appropriately modified for use in a pharmaceutical composition. For example the molecules (e.g. polypeptides) used in accordance with the invention may be stabilized against degradation by the use of derivatives or carrier proteins as described above.

The active ingredient may also be stabilized in the compositions for example by the use of appropriate additives such as salts or non-electrolytes, acetate, SDS, EDTA, citrate or acetate buffers, mannitol, glycine, HSA or polysorbate.

Thus, the TNF mutein may be incorporated (optionally together with other active substances as a combined preparation), with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions of the invention may be formulated so as to provide quick, sustained or delayed release of the active ingredient(s) (e.g. TNF mutein) after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient(s) may be absorbed, adsorbed, incorporated or bound. This can effectively convert the product to an insoluble form. These particulate forms may overcome both stability (e.g. degradation) and delivery problems. These particles may carry appropriate surface molecules to improve circulation time (e.g. serum components, surfactants, polyoxamine908, PEG etc.) or moieties for site-specific targeting, such as ligands to particular cell borne receptors. Appropriate techniques for drug delivery and for targeting are well known in the art and are described in WO99/62315.

The use of solutions, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Forms adapted for oral or parenteral administration include plain or coated tablets, capsules, suspensions and solutions containing the active component(s) optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The TNF muteins of the present invention are thus preferably formulated for systemic administration to said patient by a parenteral or enteral route, and are particularly preferably formulated for systemic administration to said patient by intravenous administration.

In a particularly preferred embodiment, the TNF muteins are formulated for systemic administration, such that a carrier protein such as albumin is also present. Such carrier proteins are widely used to stabilise active ingredients in pharmaceutical compositions and are well known in the art.

As discussed above, permeabilisation of tumour vasculature, which is achieved by systemic administration of a TNF mutein as hereinbefore defined, allows for improved access of agents such as signal generating (e.g. imaging) agents and therapeutic (e.g. anticancer) agents to tumours. This in turn allows the agents to exert their effects in or on the tumour in a more effective manner.

By "tumour" it is meant an abnormal mass of tissue formed by the growth of cells. For this reason they are often termed solid tumours. Tumours may also be called neoplasms and can be benign or malignant (cancerous). Benign tumours do not invade other tissues and do not form metastases. Malignant tumours on the other hand will tend to undergo invasion and metastasis, thus forming secondary tumours at distinct sites. Tumours may also be described as "pre-malignancy", "pre-cancer or "non-invasive" tumours. These are not invasive or metastatic tumours but they have the potential to progress to become invasive if they are left untreated.

A primary tumour is a tumour that is at the original site where it first arose. For example, a primary brain tumour is one that arose in the brain as opposed to one that arose elsewhere and metastasized (spread) to the brain. Secondary or metastatic tumours (metastases) on the other hand develop as a result of metastasis from the original cancer and are derived from the metastasis of a primary tumour. All such tumours may be detected, diagnosed or treated according to the methods of the present invention.

The methods of the invention may be used to detect (e.g. image) and treat any solid tumour in the periphery or in the CNS (including the brain and spinal cord). The term "periphery" refers to non-CNS regions of the body.

Appropriate tumours for treatment include those present or arising in the following conditions, Adrenocortical Carcinoma, AIDS-Related Cancers, Anal Cancer, Appendix Cancer, Astrocytoma, Bladder Cancer, Bone Cancer (Osteosarcoma and Malignant Fibrous Histiocytoma), Brain Tumor, Breast Cancer, Burkitt Lymphoma, Gastrointestinal Carcinoid Tumor, Carcinoma of Unknown Primary, Primary Central Nervous System Lymphoma, Cervical Cancer, Colon Cancer, Endometrial Cancer, Esophageal Cancer, Ewing Family of Tumors, Extragonadal Germ Cell Tumor, Extrahepatic Bile Duct Cancer, Eye Cancer (Intraocular Melanoma or Retinoblastoma), Gallbladder Cancer, Gastric (Stomach) Cancer, Gastrointestinal Carcinoid Tumor, Gastrointestinal Stromal Tumor (GIST) Germ Cell Tumor (Extragonadal), Germ Cell Tumor, (Ovarian) Gestational Trophoblastic Tumor, Glioma, Hairy Cell Leukemia, Head and Neck Cancer, Hepatocellular (Liver) Cancer, (Primary), Hodgkin Lymphoma, Hypopharyngeal Cancer, Intraocular Melanoma, Islet Cell Tumors (Endocrine Pancreas), Kaposi Sarcoma, Kidney (Renal Cell) Cancer, Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer, (Non-Small Cell or Small Cell), Primary Central Nervous System Lymphoma, Macroglobulinemia, Waldenström, Malignant Fibrous Histiocytoma of Bone and Osteosarcoma, Melanoma (including Intraocular (Eye) Melanoma), Merkel Cell Carcinoma, Mesothelioma, Metastatic Squamous Neck Cancer with Occult Primary, Mouth Cancer, Multiple Myeloma/ Plasma Cell Neoplasm, Mycosis Fungoides, Myelodysplastic Syndromes, Myelodysplastic/Myeloproliferative Diseases, Multiple Myeloma, Chronic Myeloproliferative Disorders, Nasal Cavity and Paranasal Sinus Cancer, Nasopharyngeal Cancer, Neuroblastoma, Non-Hodgkin Lymphoma, Lip and Oral Cavity Cancer, Oropharyngeal Cancer, Osteosarcoma and Malignant Fibrous Histiocytoma of Bone, Ovarian (Epithelial or Germ cell) Cancer, Pancreatic Cancer (including Islet Cell Tumors), Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Pelvis and Ureter Transitional Cell Cancer, Respiratory Tract Carcinoma Involving the NUT Gene on Chromosome 15, Retinoblastoma, Salivary Gland Cancer, Sarcoma, Soft Tissue Sarcoma, Uterine Sarcoma, Sézary Syndrome, Skin Cancer (Nonmelanoma, Melanoma, Merkel Cell), Skin Carcinoma, Small Intestine Cancer, Squamous Neck Cancer with Occult Primary (Metastatic), Stomach (Gastric) Cancer, Testicular Cancer, Throat Cancer, Thymoma and Thymic Carcinoma, Thyroid Cancer, Carcinoma of Unknown Primary Site, Urethral Cancer, Uterine Cancer (Endometrial), Vaginal Cancer, Vulvar Cancer, Waldenström Macroglobulinemia and Wilms Tumor.

Preferred peripheral tumours include visceral tumours, i.e. tumours that are present in an internal organ of the thorax or abdomen, e.g. a liver tumour (such as a liver tumour that has metastasised e.g. from a colorectal cancer, breast cancer or lung cancer). Further preferred peripheral tumours include rectal tumours (e.g. rectal tumours with local invasion), small bowel carcinoid tumours, pancreatic tumours and renal cell carcinoma, lung, bone and breast tumours.

Furthermore, when the methods as described herein are used to treat or detect tumours in the periphery, such tumours are preferably metastatic. The tumours are also preferably small. The amount of TNF mutein to be used for the treatment or detection of peripheral tumours is also preferably as set out as preferred elsewhere herein. Preferably human peripheral tumours are treated or detected.

The methods of the invention are, however, preferably used to detect (e.g. image) and treat tumours that are found beyond or behind the BBB, i.e. CNS, including brain tumours. Within the CNS intraaxial tumours or tumours occurring in intraaxial structures are preferred. Examples of CNS tumours include Gliomas (e.g. astrocytoma, ependymoma, oligodendroglioma and mixed glioma), Acoustic neuromas, Astrocytomas (including glioblastoma multiforme), Craniopharyngiomas, Ependymomas, Haemangioblastomas, Meningiomas, Pineal region tumours, Pituitary tumours (e.g. adenomas), Primitive neuroectodermal tumours (PNETs) and Spinal cord tumours.

The methods of the invention are also preferably used to detect (e.g. image) and treat metastases, i.e. secondary tumours, particularly when they are at an early stage and hence are small. Small tumours are of a size as defined elsewhere herein. Metastases (preferably small metastases) in the CNS form a particularly preferred subgroup for detection and treatment.

The invention thus further provides a method of treating a tumour in a patient comprising administering to said patient a TNF mutein as defined herein and an anticancer agent, wherein said TNF mutein is systemically administered to said patient.

Alternatively stated the invention provides a TNF mutein as defined herein and an anticancer agent for use in treating a tumour in a patient, wherein said TNF mutein is formulated for (and intended for) systemic administration to said patient.

In an alternative embodiment, the use of a TNF mutein as defined herein and an anticancer agent in the manufacture of a medicament for treating a tumour in a patient, wherein said TNF mutein is formulated for systemic administration to said patient, is provided.

The use of a TNF mutein as defined herein in the manufacture of a medicament for treating a tumour in a patient, wherein said medicament is formulated for systemic administration to said patient, and said medicament is intended for use in combination with an anticancer agent is further provided.

The use of an anticancer agent in the manufacture of a medicament for treating a tumour in a patient, wherein said medicament is intended for use in combination with a TNF mutein as defined herein, which is formulated for systemic administration to said patient, is also provided.

In all cases, the TNF mutein of the invention is intended for systemic administration. Further preferably said anticancer agent is also formulated for systemic administration to said patient. Even more preferably said anticancer agent is also intended for systemic administration to said patient. Modes of systemic administration and appropriate formulations are discussed above.

In all cases said tumour is preferably a CNS, including brain tumour, or a metastasis (preferably a small metastasis). Metastatic tumours (preferably small metastatic tumours) in the CNS form a particularly preferred subgroup for detection and treatment.

Thus, in some embodiments, the invention provides a TNF mutein of the invention for use in permeabilizing vasculature of a CNS tumour with an intact blood brain barrier in a patient for treating, detecting or diagnosing said tumour by allowing improved access of an anti-cancer agent or a signal generating agent to said tumour by disrupting the integrity of the blood brain barrier of said tumour, wherein said TNF mutein is formulated for systemic administration to said patient.

Alternatively viewed, the invention provide a method of permeabilizing vasculature of a CNS tumour with an intact blood brain barrier in a patient for treating, detecting or diagnosing said tumour by allowing improved access of an anti-cancer agent or a signal generating agent to said tumour by disrupting the integrity of the blood brain barrier of said tumour, wherein said method comprises systemically administering an effective amount of a TNF mutein of the invention to said patient.

As used herein, "treating" refers to the reduction, alleviation or elimination, preferably to normal levels, of one or more of the symptoms or effects of said tumour relative to the symptoms or effects present in a corresponding tumour not subject to said treatment. Treatment or treating refers to both therapeutic treatment and prophylactic or preventative measures, wherein the object is to prevent or slow down (lessen) the growth or progression of the tumour. Insofar as prevention or prophylaxis are concerned, these result directly from the "treatment" of the tumour. For example if a tumour is successfully treated, it may not go on to metastasise and spread to another region of the patient. As such metastatic spread is prevented, but it is the tumour itself which is treated.

As a result of the treatment of a tumour the overall size of the tumour, the number of cells in the tumour, or the number of viable cells in the tumour may increase more slowly (i.e. the tumour may continue to grow, but to do so at a reduced rate), may not increase or may decrease. Alternatively stated, the metastatic or invasive potential or the size of the tumour may increase more slowly (i.e. may continue to become metastatic but is doing so at a reduced rate), may not increase (in that the tumour does not become metastatic or invasive) or may decrease.

The rate of tumour growth or the rate at which the tumour becomes metastatic or invasive may be less than 0.9, 0.8, 0.7, 0.6, 0.5, 0.4, 0.3, 0.2, 0.1 fold that of a corresponding tumour not subject to said treatment.

Any decrease in size of the tumour may be by at least about 20, 30, 40, 50, 60, 70, 80, 90 or 100% by volume. Any decrease in cell number or viable cell number may be by at least about 20, 30, 40, 50, 60, 70, 80, 90 or 100%.

Tumour size, cell number (including viable cell number) and ability to metastasize may be monitored through standard techniques known in the art.

Accordingly, "treating" broadly includes maintaining a subject's disease progression or symptoms at a substantially static level, increasing a subject's rate of recovery, amelioration and/or prevention of the onset of the symptoms or severity of the condition, or extending a patient's quality of life.

By "anticancer agent" it is meant any agent that can be used to treat a tumour in accordance with the definition provided above. Anticancer agents are well known in the art and any suitable anticancer agent may be used in the present invention. The nature of the particular anticancer agent is not important; all that is required is that it exerts an effect on the tumour, once it has been permitted to access it.

Examples of suitable anticancer agents for use in connection with the present invention include chemotherapeutic agents, oncolytic viruses and exosomes containing therapeutic nucleic acid molecules.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate;

purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, NJ.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-I I; topoisomerase inhibitor RFS 2000; difiuoromethylornithine (DMFO); retinoic acid; esperamicins; capecitabine; and pharmaceutically acceptable salts, acids or derivatives of any of the above.

Also included in this definition are anti-hormonal agents that act to regulate or inhibit hormone action on tumours such as anti-estrogens including for example tamoxifen, raloxifene, aromatase inhibiting 4(5)-imidazoles, 4-hydroxytamoxifen, trioxifene, keoxifene, LYI 17018, onapristone, and toremifene (Fareston); and anti-androgens such as flutamide, nilutamide, bicalutamide, leuprolide, and goserelin; and pharmaceutically acceptable salts, acids or derivatives of any of the above.

Also included are curcumin, lapatinib (Tykerb), tyrosine kinase inhibitors (e.g. Erlotinib (Tarceva), Imatinib (Glivec), Gefitinib (Iressa), Dasatinib (Sprycel), Sunitinib and Nilotinib), proteasome inhibitors (e.g. Bortezomib (Velcade)) and monoclonal antibodies such as trastuzumab (Herceptin), Cetuximab and Panitumumab and pharmaceutically acceptable salts, acids or derivatives of any of the above.

In view of the high occurrence of secondary brain cancer from a primary breast cancer, preferred chemotherapeutic agents for treating brain cancer are those which are used to treat breast cancer.

Particularly preferred chemotherapeutic agents include lapatinib, doxorubicin, trastuzumab, melphalan, paclitaxel and these compounds or combinations thereof are preferably used in the methods of the invention.

An oncolytic virus is a virus that preferentially infects and kills cancer cells by lysing them; these have obvious functions for cancer therapy, both by direct destruction of the tumour cells, and, if modified, as vectors enabling genes expressing anticancer proteins to be delivered specifically to the tumour site. Oncolytic viruses are regulated by the tumour phenotype to replicate and lyse cancer cells selectively. Examples of adenoviruses with distinct regulatory mechanisms are: Ad-dI922-947 (targets G1-S checkpoint); Ad-Onyx-015 and Ad-Onyx-017 (target p53/mRNA export); Ad-vKH1 (targets Wnt pathway) and AdEHE2F (targets estrogen receptor/G1-S checkpoint/hypoxic signalling). (Seymour L W et al Hum Gene Ther. 2008).

Any suitable oncolytic virus, alone or in combination with one or more other oncolytic virus may be used as the anticancer agent in the present invention.

Exosomes containing therapeutic nucleic acid molecules (e.g. siRNA or a nucleic acid molecule or vector encoding a therapeutically active protein) can also be used as an anticancer agent. Examples of siRNA that can be included are siRNA molecules that target tyrosine kinases or the wnt signalling pathway.

A single anticancer agent or combinations of two or more thereof may be used.

The above discussion relates to the treatment of tumours, and as discussed above the systemic administration of a TNF mutein of the invention will also improve methods of detecting tumours that rely on or are enhanced by the use of a signal generating, e.g. imaging agent.

Imaging techniques to detect tumours in vivo often use imaging agents which are administered to the patient and which serve to improve or enhance the resultant images so that any tumours are more readily detectable. Imaging methods such as X-ray, CT scans and MRI have for many years employed such imaging agents. Although images that provide useful information can be obtained in the absence of imaging agents, the use of these agents can vastly improve the images that are obtained and hence improve the information that is obtained from carrying out the imaging. For example on an MRI image taken without a contrast agent, tumours from about 1-2 centimetres in size and larger can easily be detected. However, it is desirable to be able to detect smaller tumours and hence contrast-enhanced imaging is advantageous.

In order to be able to function as imaging agents, the relevant agents must enter or interact with the tumour tissue itself. As discussed above, in such cases the success of the detection method will rely on the ability of the imaging agent to access or make contact with the tumour. Since the systemic administration of a TNF mutein of the invention to a patient will permeabilise the tumour vasculature as discussed above, this will result in imaging agents also being able to cross the tumour vasculature to access the tumour more readily than in the absence of a systemically administered TNF mutein. It is clear from this that imaging methods which rely on the access of an imaging agent to the tumour will thus be improved relative to known imaging methods.

In a further embodiment therefore the present invention provides a method of detecting a tumour in a patient comprising administering to said patient a TNF mutein of the invention and a signal generating (e.g. imaging) agent, wherein said TNF mutein is systemically administered to said patient.

Alternatively stated, the invention provides a TNF mutein as described herein and a signal generating (e.g. imaging) agent for use in detecting the presence or absence of tumours in a patient, wherein said TNF mutein is formulated for (and intended for) systemic administration to said patient.

In an alternative embodiment, the use of a TNF mutein as described herein and a signal generating (e.g. imaging) agent in the manufacture of a diagnostic reagent for detecting the presence or absence of a tumour in a patient, wherein said TNF mutein is formulated for (and intended for) systemic administration to said patient, is further provided.

The use of a TNF mutein as described herein in the manufacture of a diagnostic reagent for detecting the presence or absence of a tumour in a patient, wherein said diagnostic reagent is formulated for systemic administration to said patient, and said diagnostic reagent is intended for use in combination with a signal generating (e.g. imaging) agent is furthermore provided.

The use of a signal generating (e.g. imaging) agent in the manufacture of a diagnostic reagent for detecting the presence or absence of a tumour in a patient, wherein said diagnostic reagent is intended for use in combination with a TNF mutein as described herein which is formulated for (and intended for) systemic administration to said patient is also provided.

In all cases, said TNF mutein is intended for systemic administration to said patient. Further preferably said signal generating (e.g. imaging) agent is also formulated for systemic administration to said patient. Even more preferably said signal generating (e.g. imaging) agent is also intended for systemic administration.

In all cases, a further step of recording the signal (e.g. obtaining an image) of the patient may be carried out to detect the presence or absence of said tumour. This step of recording a signal also forms a further optional step in the above methods and uses.

The image thus recorded or obtained can be analysed in order to determine whether it is indicative of the presence of a tumour and thereby it can be determined whether a tumour is present or absent.

By "detecting the presence or absence of a tumour" it is meant carrying out steps to determine whether or not a tumour can be observed, e.g. using imaging techniques such as MRI. The image of the patient that is obtained by carrying out the imaging technique is thus observed and it is determined whether the resultant image is indicative of the presence of a tumour, or whether it is indicative of the absence of a tumour (or the absence of a tumour that is of such a size as can be detected by that particular technique). It is expected that very small tumours (e.g. less than 0.1 mm in diameter) will not be detectable and as such a conclusion that there is no tumour is in fact a conclusion that no tumour of a detectable size is present.

This can be performed by reference to appropriate controls and/or references, such as patients who are known not to have a tumour, or to other regions of the patient's body which do not have a tumour.

As discussed above, systemic administration of the TNF mutein of the invention causes tumour vasculature to become permeabilised. The signal generating, e.g. imaging, agent can then access the tumour. Once the patient has been administered with both the TNF mutein and the signal generating (e.g. imaging) agent, the step of detecting that agent, e.g. of recording an image of the patient, can then occur.

This can be done for example by X-ray, CT scan or magnetic resonance imaging (MRI).

The above described methods are particularly advantageous for detecting the presence or absence (and also of treating) of small tumours. Small tumours are tumours that are less than 20 mm, 15 mm, 10 mm, 5 mm, e.g. less than 4, 3, 2, 1, 0.5, 0.25 mm in diameter. As mentioned above, tumours less than 0.1 mm in diameter may not be detectable and as such the methods are preferably of use for detecting the presence or absence or for treating tumours that are 0.1-20, 0.25-15, 0.5-10, 1-5 or 2-4 mm in diameter.

As discussed in more detail above, the existence of the BBB is such that small tumours that are behind or beyond the BBB are particularly difficult to detect. As such the methods described herein are of particular application to tumours that are behind or beyond the BBB, including the list of tumours referred to above. Metastases (preferably small metastases) in the CNS form a particularly preferred subgroup for detection and treatment.

The above described methods and uses are also particularly advantageous for detecting metastatic tumours particularly when they are at an early stage, i.e. when they are small, i.e. of the sizes referred to above. Whilst the methods can be used to detect metastases throughout the body, this is particularly true when said tumour is behind or beyond the BBB.

When the methods as described herein are used to detect tumours in the periphery, such tumours are preferably metastatic and preferably small. When the methods as described herein are used to detect tumours in the periphery the amount of TNF mutein of the invention used is also preferably as set out as preferred elsewhere herein. When the methods as described herein are used to detect tumours in the periphery, this is preferably in a human.

A "signal generating agent" as referred to herein is an agent, wherein by virtue of its association with the tumour, provides a detectable signal, or enhances an existing signal (e.g. radiation, light) and the increased signal (relative to normal) can be used to establish the presence or absence of a tumour. Preferably the signal generating agent is an imaging agent.

The "imaging" agent is any agent which is used to obtain or to produce or to enhance an image of a patient, and particularly any agent which is used to obtain or to produce or to enhance an image of a tumour in a patient.

The imaging agent may be an agent which enters or interacts with tumour tissue. Such agents may or may not also interact with normal or non-tumour tissue, but in general they will preferentially interact with or bind to tumour tissue. Examples of such imaging agents are labelled antibodies and passive contrast agents and targeted contrast agents. Such agents are often termed "blood pool contrast agents".

Contrast agents are well known and are widely used in imaging techniques to increase the signal difference between the area of interest and background and include gadolinium-based compounds and iron oxide contrast agents (Superparamagnetic Iron Oxide (SPIO) and Ultrasmall Superparamagnetic Iron Oxide (USPIO)).

Examples of appropriate imaging agents include X-ray contrast agents such as Acetrizoic Acid Derivatives, Diatrizoic Acid Derivatives, Iothalamic Acid Derivatives, Ioxithalamic Acid Derivatives, Metrizoic Acid Derivatives, Iodamide, Lypophylic Agents, Aliphatic Acid Salts, Iodipamide, Ioglycamic Acid, Ioxaglic Acid Derivatives, Metrizamide, Iopamidol, Iohexol, Iopromide, Iobitridol, Iomeprol, Iopentol, Ioversol, Ioxilan, Iodixanol, Iotrolan, MRI contrast agents such as gadopentetate dimeglumine, gadoteridol, gadoterate meglumine, mangafodipir trisodium, gadodiamide, Gadopentetic acid, Gadoteric acid, Gadolinium, Mangafodipir, Gadoversetamide, Ferric ammonium citrate, Gadobenic acid, Gadobutrol, Gadoxetic acid, Superparamagnetic, Ferumoxsil, Ferristene, Iron oxide, nanoparticles, Perflubron, Ultrasound agents such as Microspheres of human albumin, Microparticles of galactose, Perflenapent, Microspheres of phospholipids and Sulphur hexafluoride. Positron Emission Tomography (PET) and Single photon emission computed tomography (SPECT) agents that are normally excluded from the brain may also be used.

Preferably the imaging is carried out in a non-invasive manner (e.g. by MRI, X-ray, SPECT, PET or CT scan).

The present invention further provides a method of diagnosing a tumour as described herein in an animal, comprising at least the steps of determining the presence or absence of said tumour, wherein the presence of a signal, e.g. an image that is indicative of a tumour, e.g. on the recorded image is diagnostic of the patient having a tumour. The tumour may be detected by, for example, imaging using the methods described hereinbefore. The animal is preferably as described herein. Diagnosis may be achieved by comparison of images obtained from the patient to images obtained from patients who are known not to have any tumours (or tumours that are very small (e.g. below limits of detection (e.g. <0.1 mm or <0.05 mm in diameter).

As such the invention provides a method of diagnosing a tumour in a patient comprising administering to said patient a TNF mutein as described herein and a signal generating, e.g. imaging, agent, wherein said TNF mutein is systemically administered to said patient, detecting the signal from said signal generating agent (e.g. recording an image of said patient), determining the presence or absence of tumours by assessing the level of said signal (e.g. on said recorded image) and diagnosing said patient on the basis of the presence or absence of said tumours on the recorded image.

Alternatively stated the invention provides a TNF mutein as described herein and a signal generating, e.g. imaging, agent for use in diagnosing a tumour in a patient, wherein said TNF mutein is formulated for (and intended for) systemic administration to said patient.

In an alternative embodiment, the use of a TNF mutein as described herein and a signal generating, e.g. imaging, agent in the manufacture of a reagent (e.g. a diagnostic reagent) for diagnosing a tumour in a patient, wherein said TNF mutein is formulated for (and intended for) systemic administration to said patient, is provided.

The use of a TNF mutein as described herein in the manufacture of a reagent (e.g. a diagnostic reagent) for diagnosing a tumour in a patient, wherein said reagent is formulated for systemic administration to said patient, and said reagent is intended for use in combination with a signal generating e.g. imaging agent is further provided.

The use of signal generating, e.g. imaging, agent in the manufacture of a medicament for diagnosing a tumour in a patient, wherein said reagent (e.g. a diagnostic reagent) is intended for use in combination with a TNF mutein as described herein which is formulated for (and intended for) systemic administration to said patient is also provided.

In all cases, said TNF mutein is intended for systemic administration to said patient. Further preferably said a signal generating (e.g. imaging) agent is also formulated for systemic administration to said patient. Even more preferably said a signal generating (e.g. imaging) agent is also intended for systemic administration.

In all cases described above, the patient as referred to herein is preferably a mammal, reptile, bird, insect or fish. Preferably the patient is a mammal, particularly a primate, domestic animal, livestock or laboratory animal. Thus preferred patients include humans, mice, rats, rabbits, guinea pigs, cats, dogs, monkeys, pigs, cows, goats, sheep and horses. Especially preferably the patient is a human.

The TNF mutein may be administered in any amount which is effective to induce the permeability of the tumour vasculature as discussed elsewhere herein. For instance, the TNF mutein may be formulated such that 0.1-1000 μg/m² TNF mutein is administered to said (e.g. human) patient. Thus, in some embodiments, the TNF mutein is formulated such that 0.5-950, 1-900, 1.5-850, 2-800, 2.5-750, 5-700, 10-650, 15-600, 20-550 or 25-500 μg/m² TNF mutein is administered to said patient. In some embodiments, the TNF mutein is administered in a single dose. However, in some embodiments, it may be necessary to administer multiple doses (e.g. 2, 3, 4 or more) to ensure that the permeabilizing effect is sustained while the therapeutic or signal generating molecule is present in the system of the patient. Thus in methods or uses of the invention said TNF mutein may be administered at, or intended for administration at, a dose as indicated above. The TNF mutein is formulated such that an amount that is less than the maximal tolerated dose for wild-type TNF is administered to said patient. The skilled person would understand how to calculate an appropriate dose of TNF mutein to administer.

It may be possible to further reduce the dose of the TNF mutein by formulating the TNF mutein for co-administration with a compound that ameliorates the unwanted side effects of the TNF mutein. Such additional compounds or adjunct therapies (such as antiapoptotic agents) can be used to reduce any undesirable side effects of the TNF mutein, thus allowing a higher dose to be administered. Thus the TNF mutein may be formulated for administration with a compound that ameliorates the unwanted side effects of the TNF mutein, such as an antiapoptotic reagent.

The therapeutic, e.g. anticancer, agent and the signal generating, e.g. imaging, agent are administered in any amount which is effective to treat or to image the tumour. The concentrations or doses to be used will depend on the nature of the agent and the concentrations or doses should be determined in accordance with the manufacturer's guidelines. It is likely that lower concentrations or doses than those recommended can be used, e.g. less than 95, 90, 85, 80, 75, 70, 65, 60, 55, 50, 45, 40, 35, 30, 25, 20, 15 or 10% of the concentration or dose recommended for a particular agent can be used.

As discussed above, systemic administration of the TNF mutein of the invention causes transient permeabilisation of the tumour vasculature. As such, the administration of the TNF mutein and the anticancer agent or the signal generating, e.g. imaging, agent as appropriate preferably occurs simultaneously or at such a time interval such that the anticancer agent or the signal generating, e.g. imaging, agent is present in the vascular system during the time at which the tumour vasculature is permeabilised.

Depending on the pharmacokinetics of the relevant anticancer agent or the signal generating, e.g. imaging, agent the anticancer agent or the signal generating e.g. imaging, agent may be administered prior to the TNF mutein (e.g. up to 1, 2, 3, 4, 5, 6, 7, 8, 9, 10, 12, 14, 16, 18, 20, 22, 24 hours before the TNF mutein), simultaneously with the TNF mutein or subsequent to the TNF mutein (e.g. up to 1, 2, 3, 4, 5, 6, 7, 8, 9, 10, 12, 14, 16, 18, 20, 22, 24 hours after the TNF mutein), e.g. 1-12, 2-11, 3-10, 4-9, 5-8, 6-7 hours after the TNF mutein.

Preferably the signal is detected around 4 hours (e.g. from 3 to 6 hours) after the administration of the signal generating agent and this detection step forms a preferable step in the methods and uses referred to above.

As discussed above, the TNF mutein of the invention and the anticancer or signal generating, e.g. imaging agent can be administered together or separately. The invention thus further provides a product or kit comprising a TNF mutein of the invention and an anticancer agent as a combined preparation for simultaneous, separate or sequential use in treating a tumour, wherein said TNF mutein is formulated for systemic administration to said patient.

Also provided is a product or kit comprising a TNF mutein of the invention and a signal generating, e.g. imaging, agent as a combined preparation for simultaneous, separate or sequential use in detecting the presence or absence of a tumour, wherein said TNF mutein is formulated for systemic administration to said patient.

Also provided is a product or kit comprising a TNF mutein of the invention and a signal generating, e.g. imaging, agent as a combined preparation for simultaneous, separate or sequential use in diagnosing a tumour, wherein said TNF mutein is formulated for systemic administration to said patient.

Preferred TNF muteins, anticancer agents and signal generating, e.g. imaging, agents, as well as doses, formulations and concentrations thereof are as set out elsewhere herein.

In a further particular embodiment, the invention provides a pharmaceutical composition comprising a TNF mutein of the invention and an anticancer agent.

In addition, the present invention also provides a pharmaceutical composition comprising a TNF mutein of the invention and an signal generating, e.g. imaging, agent.

Any TNF mutein as defined herein can be used in said composition, in combination with any anticancer agent or signal generating, e.g. imaging, agent as defined herein.

The composition is preferably formulated to be suitable to administer the doses of TNF mutein referred to above as preferred doses. The composition may be formulated for administration in a volume of 0.2 ml-20 ml, e.g. 0.5 or 1 ml-10 ml or 1.5 ml-5 ml. For instance, a total dose of 200 μg TNF mutein equates to a total concentration of 10 μg/ml in 20 ml and 1 mg/ml in a volume of 0.2 ml. Similarly, a total dose of 2 μg TNF mutein equates to a total concentration of 0.01 μg/ml in a volume of 20 ml and 10 μg/ml in a volume of 0.2 ml. Thus, in some embodiments, the TNF mutein is present at a total concentration of 0.01 μg/ml-1 mg/ml, e.g. 0.05 μg/ml-0.75 mg/ml, 0.1 μg/ml-500 μg/ml, 0.2 μg/ml-400 μg/ml, 0.5 μg/ml-300 μg/ml, 1 μg/ml-250 μg/ml, 5 μg/ml-200 μg/ml, 10 μg/ml-150 μg/ml or 20 μg/ml-100 μg/ml.

The TNF mutein as described hereinbefore and signal generating, e.g. imaging, or anticancer agent as described hereinbefore may be present in said compositions as the sole active ingredients or may be combined with other ingredients, particularly other active ingredients, e.g. to augment the therapeutic effect or to make the composition more appealing to the consumer. Preferred anticancer agents and signal generating e.g. imaging, agents, doses, formulations and concentrations thereof are as set out elsewhere herein. Preferred compositions comprise the agents referred to above as being preferred anticancer agents or signal generating agents.

Examples of additional molecules that can be present are carrier proteins and adjuncts as defined elsewhere herein.

The following Examples are given by way of illustration only in which the Figures referred to are as follows:

FIG. 1 shows an overview of the selection cascade used to identify phage expressing TNF muteins with the required TNFR binding properties.

FIG. 2 shows a table of the relative binding of TNF proteins to hTNFR1, hTNFR2, mTNFR1 and mTNFR2 as assessed by Biacore single cycle analysis. Control proteins as show in light grey. 10 variants (corresponding to SEQ ID NO: 2-11) chosen for further analysis are shown in dark grey. ND=Not determined; +++=significant binding observed, slow dissociation; ++=binding observed but overall response lower or faster dissociation; +=a small but significant binding above background observed; and −=no obvious binding observed.

Figure 3:
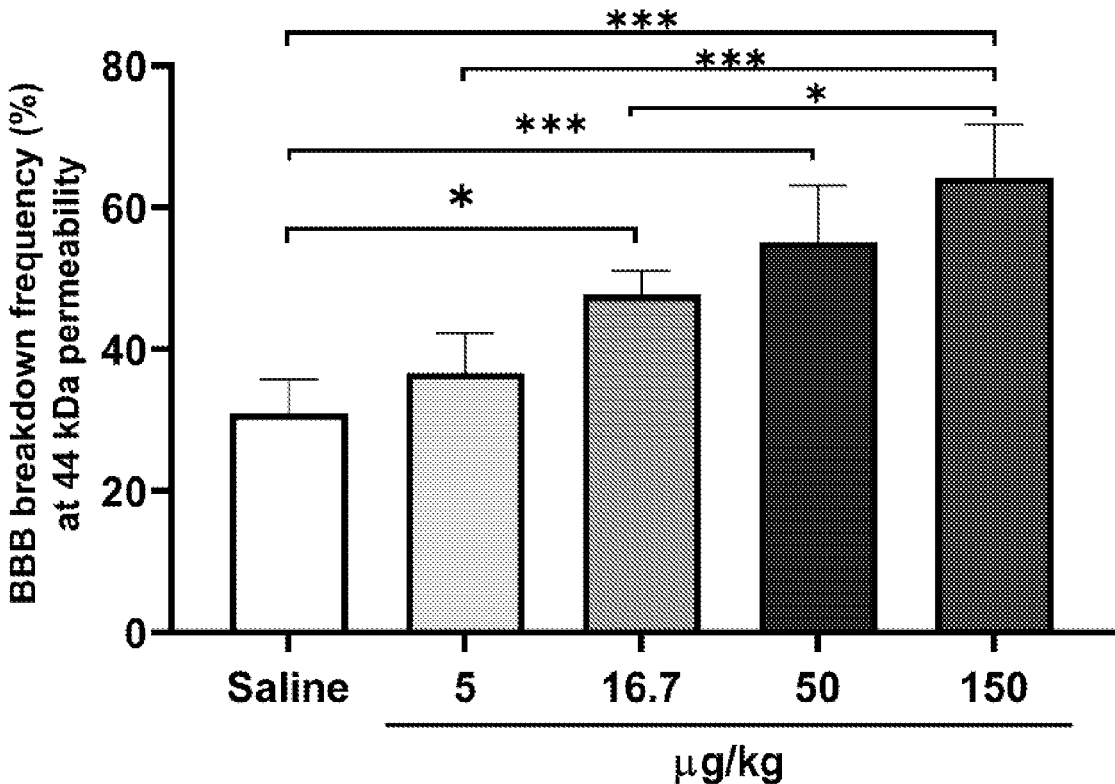

FIG. 3 shows a bar chart showing the dose-response analysis of metastasis-specific BBB breakdown frequency 2 h after different doses of mutTNF (G4 TNF mutein (SEQ ID NO: 2)); 5, 16.7, 50 and 150 μg/kg (n=3 for all groups, except 50 μg/kg and saline where n=4). Statistical analysis: All values are expressed as mean±SD. 1-way ANOVA with post-hoc Tukey's test (*P<0.05, P<0.01, *P<0.005). Error bars represent standard deviation.

Figure 4:
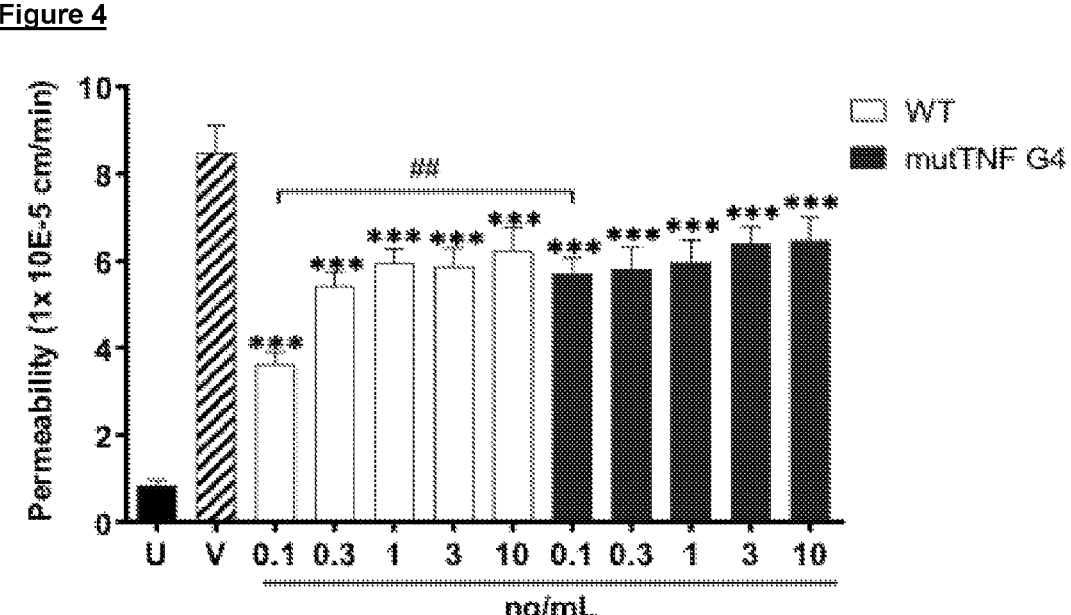

FIG. 4 relates to the in vitro assessment of the biological activity of mutTNF G4 (SEQ ID NO: 2) and shows a bar chart of the assessment of alterations in permeability as reflected by changes in permeability coefficients (Pe) of a hCMEC/D3 cell monolayer treated with 0.1-10 ng/mL of hTNF (WT) or mutTNF (G4) for 24 h, VEGF (V) as positive control, or untreated cells (U) as negative control. Statistical analysis: All values are expressed as mean±SD. 1-way ANOVA with Sidak's post hoc test vs. untreated group (P<0.01, *P<0.005) or huTNF group (##<0.01, ###P<0.005). Error bars represent standard deviation.

Figure 5:
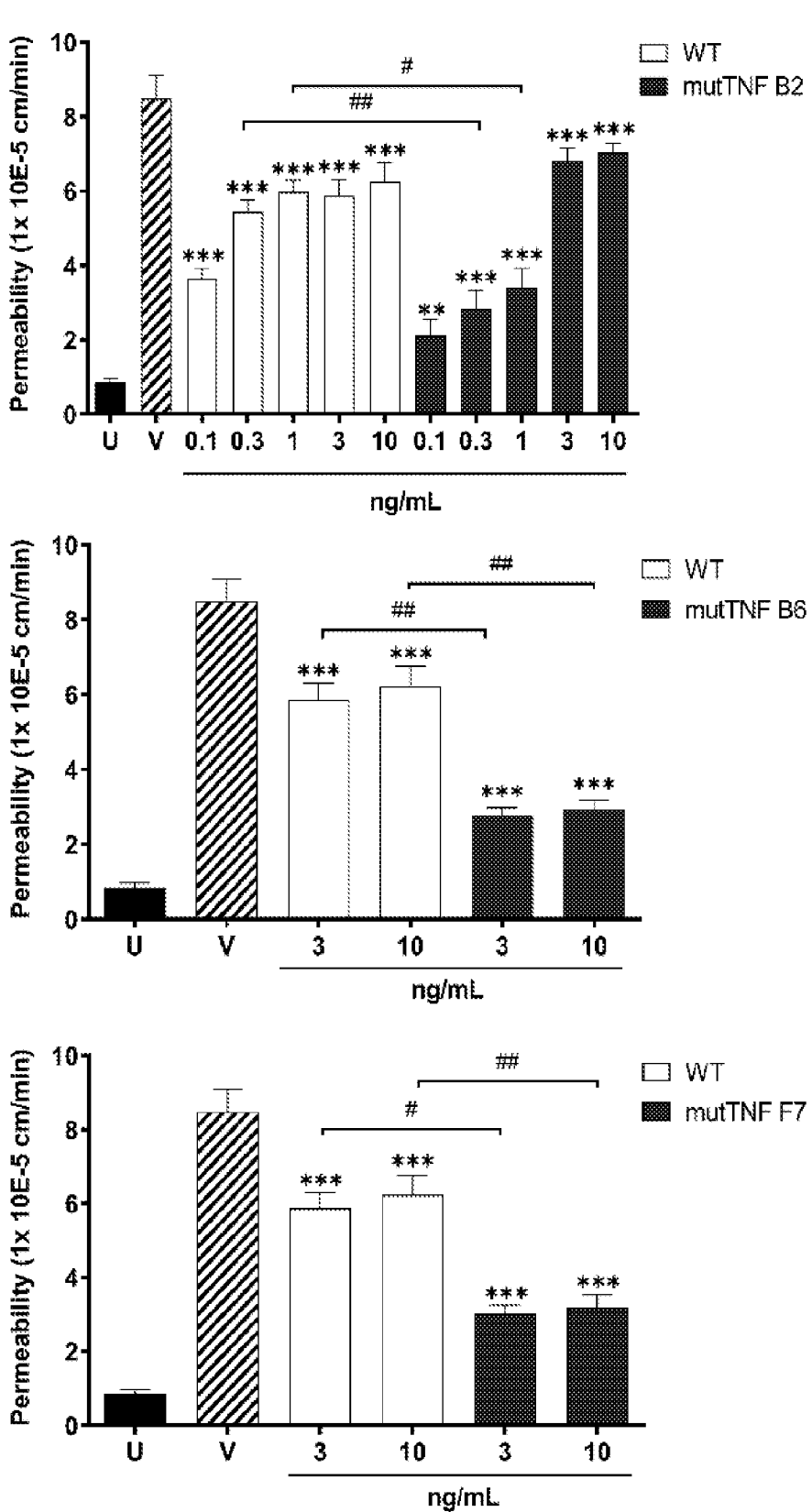

FIG. 5 provides bar charts showing the results of the in vitro paracellular permeability assay described in Example 13. Assessment of alterations in permeability of hCMEC/D3 cells monolayer treated with 0.1-10 ng/mL of hTNF (WT) or mutTNF (B2, B6 and F7) for 24 h, VEGF (V) as positive control or untreated cells (U) as negative control.

Figure 6:
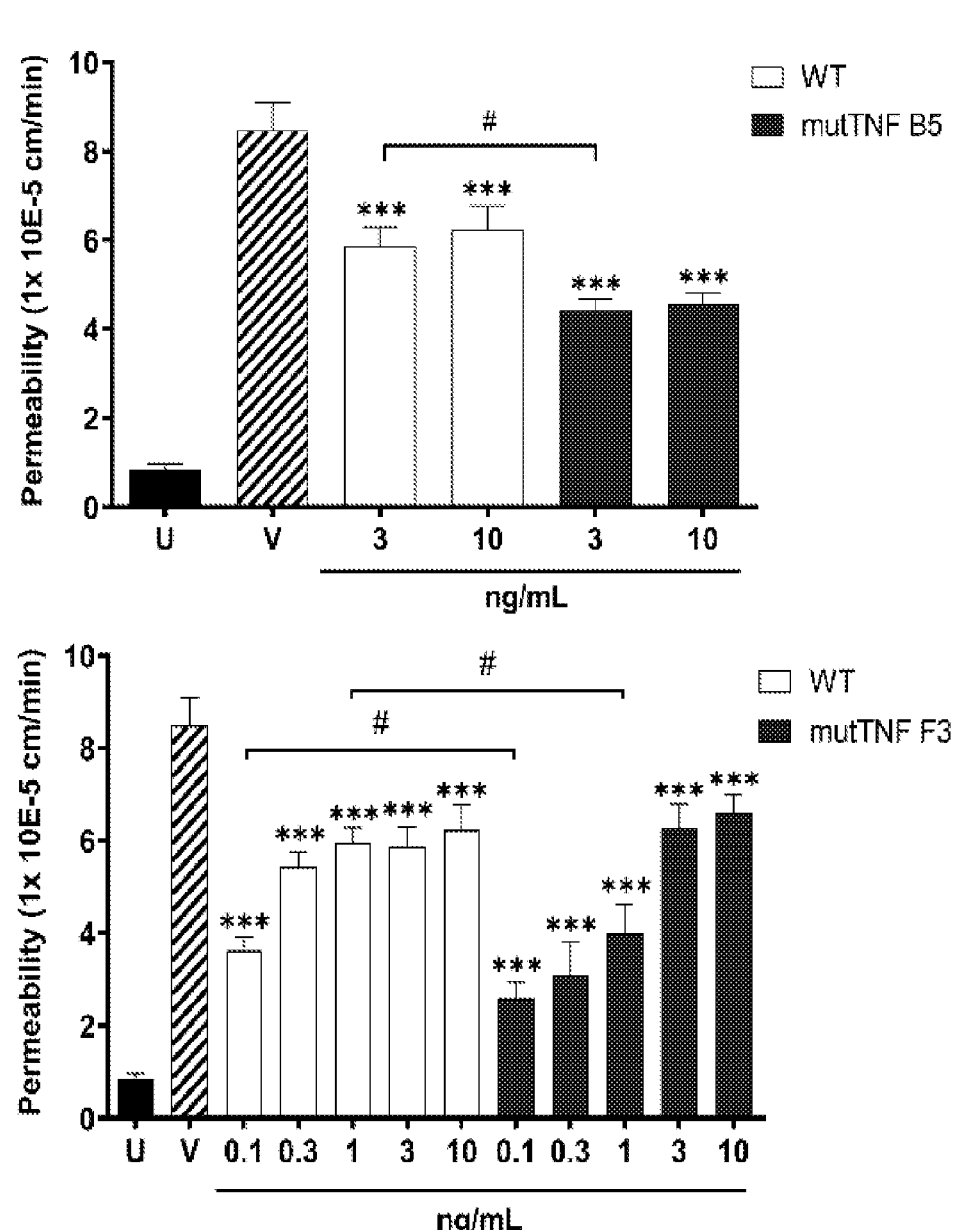

FIG. 6 provides bar charts showing the results of the in vitro paracellular permeability assay described in Example 13. Assessment of alterations in permeability of hCMEC/D3 cells monolayer treated with 0.1-10 ng/mL of hTNF (WT) or mutTNF (B5 and F3) for 24 h, VEGF (V) as positive control or untreated cells (U) as negative control.

Figure 7:
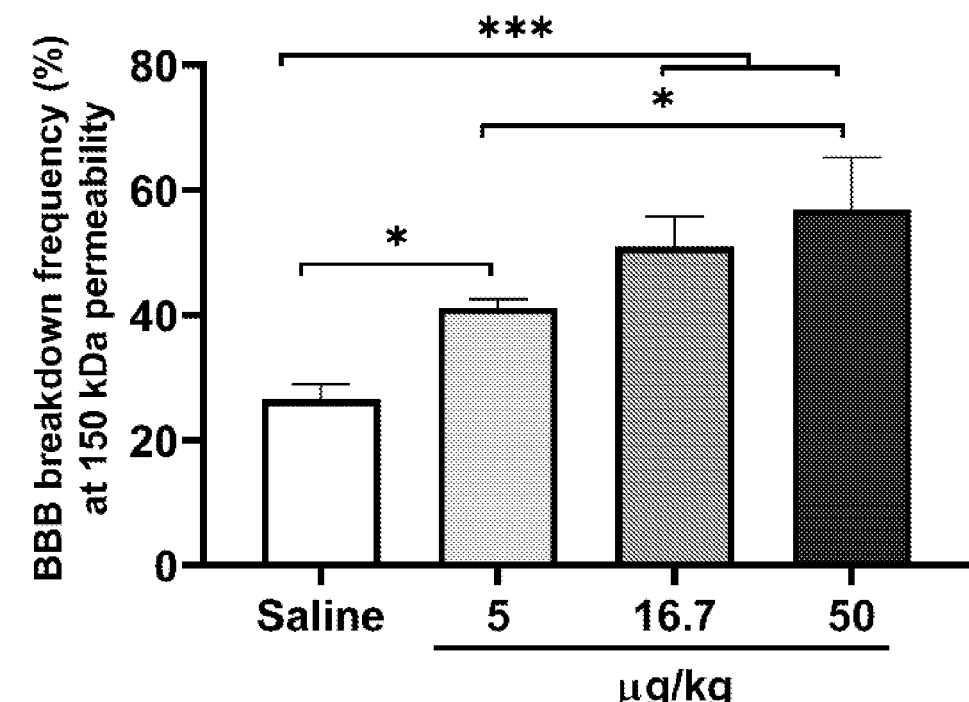

FIG. 7 relates to the histological assessment of BBB breakdown after different doses of mutTNF in a breast cancer brain metastasis model by IgG immunostaining described in Example 12 and provides a bar chart showing dose-response analysis of metastasis-specific BBB breakdown frequency 2 h after different doses of mutTNF; 5, 16.7 and 50 μg/kg (n=3 per group). Statistical analysis: All values are expressed as mean±SD. 1-way ANOVA with post-hoc Tukey's test (*P<0.05, P<0.01, *P<0.005). Error bars represent standard deviation.

Figure 8:
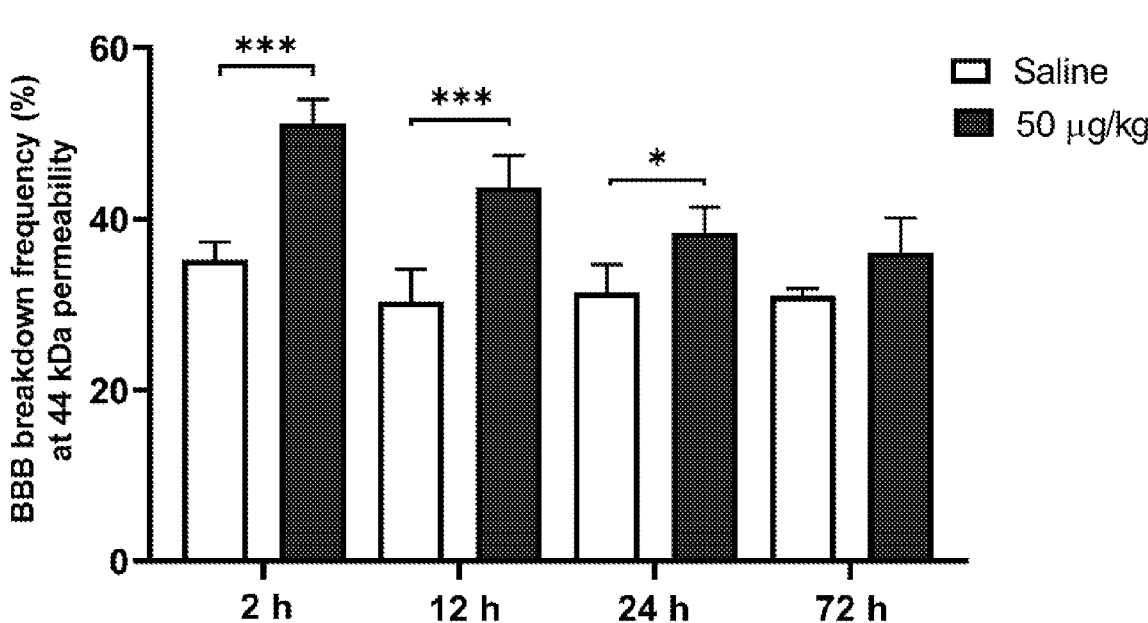

FIG. 8 relates to the histological assessment of time-frame of BBB breakdown after administration of 50 μg/kg mutTNF in a breast cancer brain metastasis model described in Example 12 and provides a bar chart showing analysis of metastasis-specific BBB breakdown frequency at 2, 12, 24 and 72 h after systemic administration of 50 μg/Kg mutTNF (n=6 per group for mutTNF treated animals; n=3 per group for saline treated animals). Statistical analysis: All values are expressed as mean±SD. 1-way ANOVA with Sidak's post hoc test vs. saline group (*P<0.05, P<0.01, *P<0.005). Error bars represent standard deviation.

Figure 9:
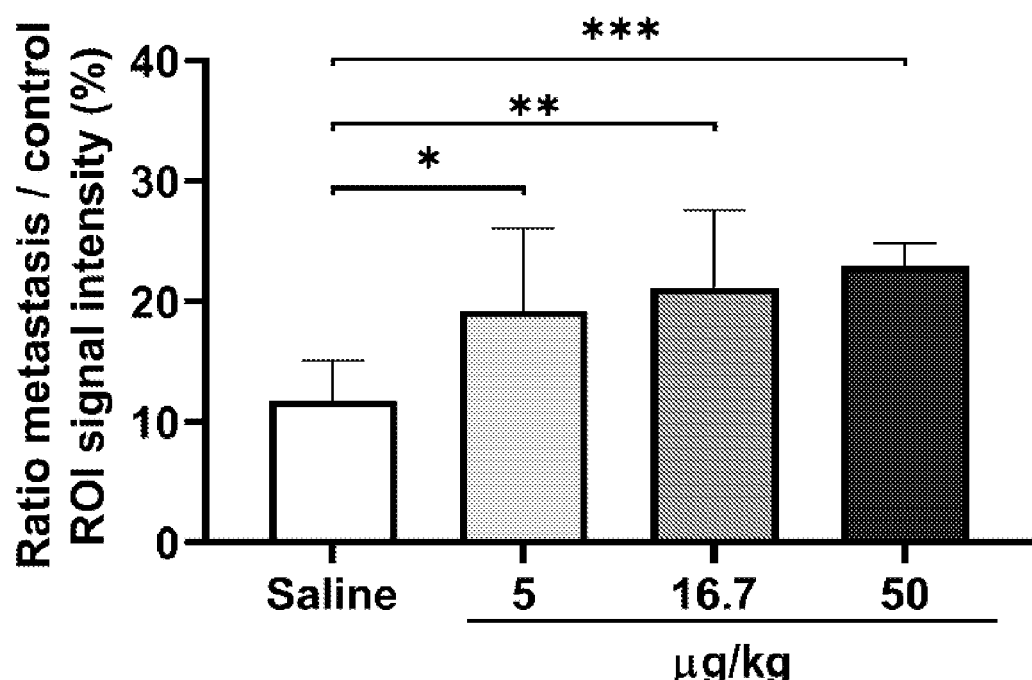

FIG. 9 relates to Gd-DTPA enhancement at metastatic sites described in Example 12 abd provides a bar chart showing percentage Gd-DTPA enhancement at sites of metastases (n=6 per group). Statistical analysis: All values are expressed as mean±SD. Non-parametric Kruskal-Wallis test was performed with Dunn post-hoc test vs. saline group (*P<0.05, P<0.01, *P<0.005). Error bars represent standard deviation.

EXAMPLES

The inventors designed and implemented a screening process to identify TNF muteins with improved properties as discussed herein. In particular, phage display libraries were designed and selection criteria were developed to determine whether TNF muteins with the desired properties could be obtained.

Example 1: Phage Vector Construction and Testing of hTNF, hTNF R32W S86T and mTNF for Binding to hTNFR1, hTNFR2, mTNFR1 and mTNFR2

Human (hTNF) and mouse TNF (mTNF) sequences were codon optimised for expression in *E. coli* and synthesised with flanking restriction enzyme sites for cloning into phagemid vector pANT65 (Abzena). hTNF R32W S86T was generated using Quikchange mutagenesis of hTNF (Agilent Technologies, Santa Clara, USA) prior to cloning into pANT65. All three sequences were cloned into pANT65 using the restriction enzymes Ncol I and Not I, allowing for display of TNF on the phage surface as a gene III fusion protein. This plasmid also contains a C-terminal Flag tag for detection of the expressed protein as well as a His6 tag for purification. The cloned TNF constructs were transformed into *E. coli* (TG1) and all constructs were confirmed by sequencing.

Phage were recovered by infecting *E. coli* with either monovalent M13K07 helper phage (New England BioLabs, Hitchin, UK) or multivalent hyper phage (M13 K07ΔpIII helper phage) (Progen, Heidelberg, Germany). Phage displaying hTNF, hTNF R32W S86T, mTNF and an irrelevant scFv were prepared and tested for binding to Fc tagged hTNFR1, hTNFR2, mTNFR1 and mTNFR2 (Sino Biological, Beijing, P. R. China).

hTNF phage bound to hTNFR1, hTNFR2 and mTNFR1 but not mTNFR2, although a small degree of binding to mTNFR2 when presented on hyper phage with increased avidity. As expected, hTNF R32W S86T bound to hTNFR1 (although significantly weaker than WT hTNF) and did not show binding to hTNFR2, mTNFR1 or mTNFR2. mTNF showed binding to all four receptors. In all cases, the binding observed was specific as no binding was observed with the irrelevant scFv phage. TNF constructs recovered using hyper phage bound at lower titres than TNF constructs recovered using M13 helper phage as a result of presentation of an increased number of TNF molecules on the phage surface.

Example 2: Library Design and Construction

Library Design

Library 1 specifically targeted the A84 to T89 loop which forms part of the receptor binding site. A wobble between the wild type residue Ser and Thr was allowed at position 86 while for all other positions within the loop all possible 20 amino acids were allowed. In addition, a wobble between Arg and Trp was allowed at position 32 to allow inclusion of the wild type Arg amino acid.

Library 2 targeted two additional areas. The loop containing amino acids L29-R32 were randomised with L29 and R31 permitted to be any amino acid while a wobble between R and W was allowed at position 32. In the region of F144-S147, limited diversity was allowed in position F144 while for A145, E146 and S147 complete randomization to all possible 20 amino acids was allowed. In order to probe both wild type and hTNF S86T sequences, a wobble between wild type Ser and Thr was also allowed at position 86.

Library Construction

To construct the designed libraries, PCRs were performed on a hTNF template containing stop codons. The purpose of this step was to reduce the likelihood of hTNF and hTNF R32W S86T being produced and dominating selections (as is occasionally observed during affinity maturation), such that only randomized proteins generated by PCR can form in a phagemid vector. Stop codons were introduced into hTNF cloned into the unrelated plasmid, pJ201, using Quikchange mutagenesis at R32 and S86. Degenerate primers were designed to bind to these regions thus removing the stop codon when amplification occurs.

For library 1a and 1 b, randomization was carried out in three stages. Initially, using a stop codon template covering amino acid 86, the 3' portion of the TNF containing amino acids A84-T89 was amplified with the randomized 5' library primer and a 3' primer specific for the 3' end of TNF and containing a Not I restriction site. Next, in two separate PCR reactions the 5' portion of TNF containing either R32 (WT, library 1a) or W32 (mutein, library 1b) was amplified with a 5' primer containing Nco I and a 3' primer that was complementary to a portion of the randomized primer. Lastly, the full-length libraries were constructed by annealing of the amplified 5' and 3' fragments and re-amplification with primers that included two restriction sites (Nco I and Not I) for sub cloning of the fragment. During construction, libraries 1a and 1b were kept separate.

For library 2a and 2b, randomization was also carried in three stages. Initially, using a stop codon template covering amino acid 32, the 5' portion of TNF containing amino acids L29-R32 was amplified with the randomized 3' library primer and a 5' primer specific for the 5' end of TNF and containing a Nco I restriction site. Next, in two separate PCRs the 3' portion of TNF containing either S86 (WT, library 2a) or T86 (mutein, library 2b) was amplified with a 5' primer that was complementary to a portion of the primer used to randomize amino acids L29-R32 and a 3' primer that introduced randomization to amino acids F143-G146. Lastly, the full-length libraries were constructed by annealing of the amplified 5' and 3' fragments and re-amplification with primers that included two restriction sites (Nco I and Not I) for sub cloning of the fragment. During construction, libraries 2a and 2b were kept separate.

Following amplification, purified DNA for all four libraries was digested using Nco I and Not I and ligated into the similarly cut phagemid vector (pANT65). Ligated DNA was precipitated, resuspended in nuclease-free water, transformed by electroporation into freshly prepared electrocompetent TG1 *E. coli* cells and plated on LBCG (2% glucose) agar plates. The following day, colonies were counted, plates scraped and glycerol stocks prepared. Libraries were electroporated multiple times to sufficiently cover the theoretical library diversity. The observed library size of each of the libraries is shown in Table 3, and a total coverage of 4.9-fold was obtained. Individual colonies from each of the libraries were sequenced to confirm that the appropriate region had been mutated.

TABLE 3

Theoretical and observed TNF variant phage library sizes

| | Library 1a | Library 1b | Library 2a | Library 2b |
|---|---|---|---|---|
| Theoretical Library Size (DNA) | $1.3 \times 10^8$ | | $5.4 \times 10^8$ | |
| Theoretical individual library size | $6.70 \times 10^7$ | $6.70 \times 10^7$ | $2.7 \times 10^8$ | $2.7 \times 10^8$ |
| Actual library size | $1.11 \times 10^9$ | $4.95 \times 10^8$ | $1.11 \times 10^9$ | $5.68 \times 10^8$ |
| Library coverage | 16.4× | 7.4× | 4.11× | 2.1× |
| Combined theoretical library size | | | $6.7 \times 10^8$ | |

TABLE 3-continued

Theoretical and observed TNF variant phage library sizes

| | Library 1a | Library 1b | Library 2a | Library 2b |
|---|---|---|---|---|
| Total Library Coverage | | 3.27 × 10⁹ (4.9×) | | |

Bacteria from each of the four libraries were inoculated into 100 ml 2×TYCG cultures using inoculum to cover ≥10× the initial library transformation size. The cultures were grown to mid-log phase (OD600 nm≈0.6) and the total number of cells estimated (based on an OD600 nm of 1≈5×108 cells/ml).

Monovalent M13K07 helper phage was added at a multiplicity of infection of 10 and incubated for 1 hour at 37° C., then centrifuged, resuspended in 2×TYCK media and grown overnight at 25° C. The following day, phage were harvested by recovering the culture supernatant by centrifugation followed by precipitation using ³⁄₁₀th volume of chilled 20% PEG/2.5 M NaCl. After an incubation period of three hours, precipitated phage were recovered by centrifugation and the pellet resuspended in 1× PBS pH 7.4. The resuspended pellet was re-centrifuged to remove any cellular debris, following which the supernatant was re-precipitated using ³⁄₁₀th volume of chilled 20% PEG/2.5 M NaCl. After a short incubation of 20 minutes to one hour (according to the round of selection), precipitated phage was recovered by centrifugation and the pellet resuspended in 1× PBS pH 7.4, following which a final centrifugation to remove any cellular debris was conducted. The precipitated phage was stored at 4° C. Phage were titred by incubating serial dilutions of phage with log phase TG1 E. coli cells for one hour before plating on LBCG (2% glucose) agar plates. The following day, colonies were counted and titres determined.

Prior to the first round of selection Libraries 1a and 1b were combined at a ratio 1:1, resulting in Library 1; and Libraries 2a and 2b were combined at a ratio 1:1 to generate Library 2.

Example 3: Affinity Improved Phage Selections hTNFR1 was used throughout for positive selections, whereas mTNFR1 was included from round 2 to increase the possibility of selecting for variants with cross reactivity. hTNFR2 was used for deselections at a final concentration of 10 nM to reduce the possibility of selecting variants with hTNFR2 cross reactivity. Deselection against hTNFR2 was performed for the first three rounds of selections. The fourth round of selection was performed solely to enrich for positive binders to hTNFR1 as the round three output titres were relatively large (≈107).

For the selections, each of the libraries containing a known number of phage was pre-blocked with MPBS following which phage were incubated with decreasing concentrations of hTNFR1 or mTNFR1 antigen for up to three hours in the first round of selection to one hour in the following rounds. Following incubation, Protein A Dyna beads (ThermoFisher, Loughborough, UK) (pre-blocked as above) were added to each selection to capture the Fc-tagged receptors and incubated for 10 minutes. Receptor-phage complexes were washed using increasing numbers of washes with PBST at each successive round of selection followed by two 1× PBS washes, with complexes captured using a magnet between each step. Phage were eluted from the beads by the addition of 50 mM HCl following which the solution was neutralised by the addition of 1 M Tris-HCl pH 9.0. An overview of the selection cascade is shown in FIG. 1. Eluted phage from each round of selection were incubated with log phase TG1 E. coli cells for one hour before plating on LBCG (2% glucose) agar plates. The following day, colonies were counted, plates scraped and glycerol stocks prepared. Phage were then rescued as described above and, if appropriate, used as inputs for subsequent rounds of selection.

Example 4: High Throughput Screening of Selection Outputs

As part of the characterisation of selection outputs, it was necessary to establish a high throughput screen. Cultures were tested initially as both phage and as periplasmic extracts, however, during the course of assay optimisation for screening, in contrast to expression as phage, it was observed that the hTNF R32W S86T mutein expressed poorly in the periplasmic extract when compared to WT hTNF, leading to a low signal in the binding ELISA.

As the mutein TNF R32W S86T did not express well in the periplasm (but was required as an assay comparator), a phage binding ELISA was selected as the primary high throughput screen. Phage produced from individual colonies from different rounds of selection were screened in a single point hTNFR1, hTNFR2 and mTNFR1 receptor binding ELISA. hTNF, hTNF R32W S86T, mTNF and an irrelevant scFv were included on each assay plate for comparison.

Individual colonies were picked into 500 µl 2×TYCG (2% glucose) media and grown by shaking at 37° C. for 5 hours. Monovalent M13K07 helper phage was added at a multiplicity of infection of 10 and incubated for 1 hour at 37° C. Following this, cultures were centrifuged, resuspended in 2×TYCK media and grown overnight at 25° C. The following day cultures were blocked with an equal volume of 2× MPBS and incubated for 1 hour at room temperature before being pelleted by centrifugation.

Nunc Immuno MaxiSorp 96 well flat bottom microtiter plates were coated with hTNFR1, mTNR1 and hTNFR2 at 0.5 µg/ml, 100 µl/well overnight. Plates were washed and blocked for 1 hour at room temperature with 3% MPBS following which 100 µl of blocked phage were then added. After incubation with phage, plates were washed with PBST, and binding of phage to hTNFR1, hTNFR2 and mTNFR1 was detected with α-M13-HRP conjugate (diluted 1:5000 in MPBS) (GE Healthcare, Little Chalfont, UK) and TMB substrate (Invitrogen, Loughborough, UK). The reaction was stopped with 1 M HCl, absorbance read at 450 nm on a Dynex Technologies MRX TC II plate reader and the binding data plotted.

Clones which bound both hTNFR1 and mTNFR1 but not hTNFR2 were classified as hits. 283 hits from the two libraries were identified from ~1700 phage that were analysed. The library and selection strategy used to obtain the 283 hits is shown in Table 4.

TABLE 4

Summary of the number of clones screened and the number of
hits from both libraries following screening in the phage and periplasmic format
(Number of hits/Number of clones screened)

| Library | Selection Round | | | | # phase hits/# phage screened | # peri hits/# peris screened |
|---|---|---|---|---|---|---|
| | 1 | 2 | 3 | 4 | | |
| 1 | hTNFR2- Fc deselection (10 nM) hTNFR1-Fc selection (10 nM) | hTNFR2-Fc (10 nM) hTNFR1-Fc selection (1 nM) deselection | hTNFR2- Fc (10 nM) hTNFR1-Fc selection (50 pM) deselection | hTNFR1-Fc selection (5 pM) | 94/360 | 24/360 |
| 2 | | | | | 0/80 | No phage ELISA HITS screened |
| 1 | | hTNFR2-Fc (10 nM) hTNFR1-Fc selection (1 nM) deselection | hTNFR2- Fc (10 nM) mTNFR1-Fc selection (10 nM) deselection | | 91/248 | 26/248 |
| 2 | | | | | 10/400 | 5/400 |
| 1 | | hTNFR2-Fc (10 nM) mTNFR1-Fc selection (10 nM) deselection | hTNFR2- Fc (10 nM) hTNFR1-Fc selection (1 nM) deselection | | 82/248 | 17/248 |
| 2 | | | | | 6/408 | 7/408 |
| | Total number of hits | | | | 283 (Library 1 = 267) Library 2 = 16 | 80 (Library 1 = 65) (Library 2 = 15) |

Example 5: Screening of TNF Variants

Periplasmic ELISA Screening of Variants

To further characterise the clones tested in the primary phage binding screen, a second round of screening was undertaken. As mentioned above, the hTNF R32W S86T mutein expressed poorly when tested as a periplasmic extract. Soluble expression is a major consideration for manufacturing, and so a secondary screen was undertaken to investigate the binding of leads to hTNFR1 when expressed in the periplasm in order to allow identification of leads with potentially improved manufacturability. Periplasmic extracts of colonies from different rounds of selection were screened in a single point assay for their ability to bind hTNFR1. For comparison purposes, hTNF, mTNF, hTNF R32W S86T and irrelevant scFv were included on each assay plate.

TNF variants were expressed and tested as crude periplasmic extracts. Individual colonies were picked into 1 ml 2×TYCG (0.1% glucose) media and grown by shaking at 37° C. for 5 hours. Cultures were induced by adding IPTG to a final concentration of 1 mM and then grown overnight, with shaking, at 30° C. The following day, cultures were centrifuged and the supernatant discarded. Bacterial pellets were resuspended in TES buffer pH 7.4 and incubated on ice for 30 minutes. The plate was then centrifuged and the protein-containing supernatant transferred to a fresh plate for assay.

Nunc Immuno MaxiSorp 96 well flat bottom microtiter plates were coated with hTNFR1 at 0.5 μg/ml, 100 μl/well overnight. Plates were washed and blocked for one hour at room temperature with 3% MPBS. Periplasmic extracts were added to the blocked plates (100 μL per well) and incubated for one hour at room temperature. Plates were subsequently washed with PBST and 100 μl per well anti-FLAG antibody (Clone M2, Sigma, Gillingham, UK) diluted 1:10000 in BTBS was added. After one hour incubation, plates were washed with TBST, and the binding of clones to hTNFR1 was detected with an anti-mouse-HRP antibody (Sigma, Gillingham, UK) and TMB substrate (Invitrogen, Loughborough, UK). The reaction was stopped with 1 M HCl, absorbance, read at 450 nm on a Dynex Technologies MRX TC II plate reader and the binding data plotted.

Greater than ~1600 clones from both libraries were analysed as part of the manufacturability assessment, with 80 clones identified as hits. In the majority of cases, clones identified in the periplasmic ELISA were also identified in the phage ELISA. Thus, the 80 periplasmic ELISA hits represent a subset of the 283 phage ELISA positive clones. A summary of the rounds of selection as well as the number of clones identifies following the phage ELISA or periplasmic ELISA are shown in Table 4 above.

Sequencing of Cherry Picked Variants

Following each round of selection, hits were sequenced. The top 80 clones which gave the highest signal in the hTNFR1 periplasmic binding ELISA were picked into a single 96-well cherry plate (row A to H, column 1 to 10) to allow direct comparison in the same assay together with hTNF, mTNF, hTNF R32W S86T and irrelevant scFv which were picked in triplicate in columns 11 and 12. The sequences of the 80 cherry plate clones were analysed and it was observed that in particular positions, there was a preference for particular amino acids. For example, in Library 1, there was a strong preference for serine or threonine at position 84. Similarly, in Library 2, there was a strong preference for acidic residues (aspartate or glutamate) at position 146.

Periplasmic Screening of Cherry Picked Variants

The clones picked into the single cherry picked plate were retested for binding to hTNFR1 using the periplasmic ELISA described above and further characterised for binding to hTNFR2 and mTNFR1 also coated at 0.5 μg/ml.

The cytotoxic activity of variants on the cherry picked plate was also measured in a cellular cytotoxicity assay using the two mouse cell lines L929 and WEHI164 and the human cell line HEp2. Cytotoxicity was assessed in a homogeneous luminescent cell viability assay in which the number of viable cells in culture is determined based on quantitation of the ATP present (ATP signals the presence of metabolically active cells). The cell lines used are described in Table 5.

TABLE 5

A summary of the cell lines used

| Cell | Species | Source | Cat. No. | TNFR1 expression | TNFR2 expression |
|---|---|---|---|---|---|
| HEp2 | Human | Sigma | 86030501-1VL | Y | Y |
| WEHI164 | Mouse | Sigma | 87022501-1VL | Y | Y |
| L929 | Mouse | Sigma | 85011425-1VL | Y | N |

As previously, hTNF, hTNF R32W S86R, mTNF as well as the irrelevant scFv were included as controls in the assays as well as a PBS control (representing 0% killing). For each assay, cells were dispensed in a final volume of 50 µl into each well of a 96-well white-walled tissue culture plate (Corning, Amsterdam, NLD). To avoid edge effects, outer wells contained growth media only. After incubation of cells with purified protein for the indicated time the plate was equilibrated at room temperature for 10 minutes and then developed by the addition of 50 µl of Cell TiterGlo® reagent (Promega, Madison, USA) to each well prior to reading in a FluoStar Optima plate reader (BMG Labtech). % killing was calculated using the following equation:

$$\% \text{ killing} = 100 - (\text{Luminescence/Untreated Cells Luminescence} \times 100)$$

$2 \times 10^5$ HEp2 cells were seeded in a total volume of 50 µl of cell growth medium (EMEM, 10% FBS, L-glutamine, NEAAs, Pen/Strep) in a 96 well plate and incubated overnight in a humidified cell culture incubator (37° C., 5% $CO_2$). The following day media was removed, and the cells sensitized for three hours by the addition of 50 µl of HEp2 assay media (growth medium containing 100 µg/ml cycloheximide (Abcam, Cambridge, UK) and the antibiotic ciprofloxacin (Glentham Life Sciences Ltd., Corsham, UK). A dilution plate was prepared containing periplasmic extracts diluted 1 in 12 in HEp2 assay media, and 50 µl was transferred directly onto the HEp2 cells, following sensitization to give a final volume of 100 µl. Plates were developed using Cell TiterGlo® reagent and read after 48 hours.

$5 \times 10^4$ WEHI164 cells were seeded in 96-well plates in a total volume of 50 µl of WEHI164 cell growth medium (DMEM, 10% FBS, L-glutamine, Pen/Strep) containing 10 µg/ml actinomycin-D and 1:500 of ciprofloxacin. A dilution plate was prepared containing periplasmic extracts diluted 1 in 12 in WEHI164 cell growth medium containing 10 µg/ml actinomycin-D and 1:500 of ciprofloxacin, and 50 µl transferred directly onto the WEHI164 cells to give a final volume of 100 µl. Plates were developed using Cell TiterGlo® reagent and read after 24 hours.

$2 \times 10^4$ L929 cells were seeded in 96-well plates in a total volume of 50 µl of L929 growth media (DMEM, 10% FBS, L-glutamine, Pen/Strep) containing 1:500 of ciprofloxacin. A dilution plate was prepared containing periplasmic extracts diluted 1 in 12 in L929 growth media (DMEM, 10% FBS, L-glutamine, Pen/Strep) containing 1:500 of ciprofloxaci and 50 µl transferred directly onto the L929 cells to give a final volume of 100 µl. Plates were developed using Cell TiterGlo® reagent and read after 48 hours.

Using the data from the cherry picked plate periplasmic ELISA together with the cellular cytotoxic assay, a top panel of 33 clones was selected.

All 33 variants bound to hTNFR1 better than hTNF R32W S86T. A large proportion of variants did not bind to hTNFR2, however, a number of variants did bind to hTNFR2 although the signal was lower than that observed for binding by hTNF. A range of binding to mTNFR1 was observed for the variants. No obvious binding to hTNFR1, hTNFR2 and mTNFR1 was observed for the Irrelevant scFv.

The cellular cytotoxicity data confirmed that hTNF and mTNF showed significant killing in all three cell lines tested. All 33 variants appeared to show killing in the L929 and WEHI164 mouse cell lines as well as the HEp2 human cell lines. For the majority of clones tested and in all three cell lines tested the cytotoxicity observed for the variants was greater than that observed for hTNF R32W S86T. The Irrelevant scFv showed minimal cytotoxicity in the assays.

The high throughput screening of phage and periplasmic extracts does not take into account differences in expression between the variants and the controls meaning that any differences observed could be as a result of differences in the amounts of each protein present. To further increase the accuracy of the characterisation of the variants with regard to purity and quantitation the 33 leads were purified and tested for hTNFR1, hTNFR2, mTNFR1 and mTNFR2 binding by Biacore.

Example 6: Expression and Purification of Lead TNF Variants

The initial screening phases described above were performed using variants produced in amber suppressor TG1 cells. These cells are suited for phage display as they allow production of phage as well as soluble protein depending on the conditions used. However, TG1 cells are not typically used for protein expression and purification and as a result an alternative *E. coli* bacterial strain (BL21(DE3)) was selected for production.

pANT65 plasmids encoding the lead 33 TNF variants together with the controls hTNF, hTNF R32W S86R and mTNF were co-transformed into Z-competent BL21(DE3) together with the pACYC GroEL/ES plasmid (Abzena) which encodes for expression of the chaperonins GroEL/ES. GroEL/ES has been shown previously to enhance folding of proteins and as a result increase soluble protein production. A pANT65 plasmid encoding an unrelated irrelevant scFv was also co-transformed to be used as a negative control in the cell based assays (37 proteins in total).

Transformed bacteria were plated out on LB agar plates containing 75 µg/mL carbenicillin and 20 µg/mL chloramphenicol and incubated overnight at 37° C. The next day, a single colony was inoculated in a 50 mL Greiner tube containing 5 mL of 2×TYCC and grown overnight at 30° C. and with shaking at 175 rpm. The following day, 1 ml of the overnight culture was transferred to 50 ml of 2TYCC in a 250 ml Erlenmeyer flask and grown at 30° C. and with shaking at 175 rpm until an OD600 nm of 0.5 was reached. 10 mL of this culture was transferred to 3 L baffled Erlenmeyer flask containing 350 mL of 2TYCC and grown at 30° C. and with shaking at 175 rpm. At an OD600 nm of 0.5, IPTG was added to a final concentration of 0.2 mM and the culture grown overnight at 30° C.

The next day, the bacteria were harvested by centrifugation for 20 minutes at 3000× g and the resulting pellet resuspended in lysis buffer (20 mM Tris pH 7.4, 200 mM $MgCl_2$, 5% glycerol). The bacteria were lysed on ice by sonicating four times for 30 seconds using a Misonix XL2020 sonicator following which the bacterial debris was pelleted by centrifugation for 1 hour at 16800× g at 4° C. After centrifugation, the supernatants were transferred to a fresh 50 mL Greiner tube and a 1 M imidazole stock added to a final concentration of 20 mM imidazole. To each tube 0.25 mL of a 50% slurry of Ni-NTA beads (Qiagen, Hilden, Germany) that had been washed 3 times in lysis buffer containing 20 mM imidazole was added. The Greiner tubes were incubated on a rotating wheel at 4° C. for 30 minutes. After rotating, the samples were loaded on 5 mL disposable columns (ThermoFisher, Loughborough, UK). The beads were then washed with ~50 mL of wash buffer (PBS containing 20 mM imidazole) following which the columns were spun for 30 seconds at 500× g to remove the residual wash buffer. Protein samples were eluted by adding 500 μl of PBS containing 200 mM imidazole, incubating for 2 minutes followed by centrifugation at 500×g for 1 minute. The elution procedure was repeated once more with 250 μl of elution buffer. After elution, fractions containing protein were buffer exchanged into 20 mM Tris pH 9.0. At this stage, it was noted that the proteins following Ni-NTA purification contained a number of impurities and so required additional purification. Proteins were further purified using a 1 mL HiTrap Q HP anion exchange column (GE Healthcare, Little Chalfont, UK) using a linear salt gradient of 0 mM to 500 mM NaCl 20 mM Tris pH 9.0 over 20 column volumes. 0.5 mL fractions were collected, analysed on SDS-PAGE and fractions containing the protein of interest pooled. The protein of interest typically eluted between 350 and 450 mM salt. Fractions were pooled and proteins were buffer exchanged into PBS pH 7.2, filter sterilised and quantified by OD280 nm using an extinction coefficient based on the predicted amino acid sequence. ~1 μg of each reduced protein was analysed by SDS-PAGE. For each protein purified, a single major band corresponding to the profile of TNF or irrelevant scFv was observed following two rounds of purification. 29 variants expressed satisfactorily to continue analysis, however, the expression of four variants was poor and as a result were not taken forward. The molecular weights and yields of the 10 lead purified variants (following single cycle kinetic analysis described in Example 7) are shown in Table 6.

TABLE 6

Yields of hTNF, hTNF R32W S86T, and lead hTNF variants following purification by Ni-NTA affinity chromatography and HiTrapQ anion exchange chromatography from a 400 mL starting culture

| Protein | $M_w$(kDa) | $A_{280}$ at 1 mg/mL | Yield (μg) |
|---|---|---|---|
| hTNF | 19.7 | 1.17 | 114.6 |
| hTNF R32W S86T | 19.8 | 1.44 | 71.2 |
| mTNF | 19.7 | 1.25 | 84.3 |
| B2 | 19.76 | 1.17 | 85.2 |
| B4 | 19.7 | 1.09 | 268.7 |
| B5 | 19.8 | 1.17 | 541.4 |
| B6 | 19.8 | 1.24 | 41.2 |
| C4 | 19.7 | 1.09 | 851.9 |
| C8 | 19.8 | 1.09 | 314.3 |
| C9 | 19.7 | 1.17 | 304 |
| F3 | 19.9 | 1.16 | 120.5 |
| F7 | 19.7 | 1.09 | 166.4 |
| G4 | 19.8 | 1.16 | 83.8 |

Single Cycle Kinetic Analysis of TNF Variant Binding to hTNFR1, hTNFR2, mTNFR1 and mTNFR2

The ability of the 29 purified lead muteins to bind to different TNF receptors and compared to hTNF, mTNF and hTNF R32W S86T was determined using single cycle Biacore analysis.

Single cycle kinetic analysis was performed using a Biacore T200 (serial no. 1909913) running Biacore T200 Evaluation Software V2.0.1 (Uppsala, Sweden). All experiments were run at 25° C. with HBS-P+ running buffer (pH 7.4) (GE Healthcare, Little Chalfont, UK).

Due to the limit in the number of available flow cells for analysis (three Fc per analysis, Fc2, Fc3 and Fc4, with Fc1 always being used as blank reference for non-specific subtraction), receptor binding was assessed in two separate overlapping runs using either: hTNFR1 (Fc2), hTNFR2 (Fc3) and mTNFR1 (Fc4), or; hTNFR1 (Fc2), mTNFR1 (Fc3) and mTNFR2 (Fc4). Receptors were diluted in running buffer to a concentration of ~4 μg/mL and at the start of each cycle loaded onto Fc2, Fc3 and Fc4 of a Protein A chip (GE Healthcare, Little Chalfont, UK) at a flow rate of 10 μL/min to give an RU of 40-100. The surface was then allowed to stabilise. Single cycle kinetic data was obtained at a flow rate of 45 μL/min. A three point three-fold dilution range from 1.67 nM to 15 nM TNF, without regeneration between each concentration, was used. The association phase for the three injections of increasing concentrations of TNF was monitored for 240 seconds and a single dissociation phase was measured for 2700 seconds following the last injection of TNF. Regeneration of the Protein A surface was conducted using 10 mM glycine-HCl pH 1.5. The signal from the reference channel Fc1 (no receptor) was subtracted from that of Fc2, Fc3 and Fc4 to correct for differences in non-specific binding to a reference surface.

Controls were used to ensure the integrity of the receptors during the Biacore run. The relative binding to all four receptors for the three controls and the 29 variants tested is shown in FIG. 2. A range of binding profiles was observed for the 29 variants tested. 27 variants showed significant binding to hTNFR1. Compared with hTNF R32W S86R, variants which bound to hTNFR1 also bound mTNFR1. For 26 variants, no significant hTNFR2 binding was observed. A small amount of hTNFR2 binding was observed for the three variants (A1, A9 and B2). All variants tested including hTNF R32W S86R did not appear to bind to mTNFR2.

As receptor affinity may not translate directly to biological function, 10 variants (G4, B5, B6, F3, F7, B2, B4, C4, C8 and C9, corresponding to SEQ ID NOs: 2-11) were selected for further testing in cellular cytotoxicity assays. These variants all bound with high affinity to hTNFR1 but showed a range of binding kinetics to mTNFR1 and either no or significantly reduced binding to hTNFR2. Table 7 shows affinity values against different receptors.

TABLE 7

Single-cycle affinity data for binding of the 10 lead variants to hTNFR1, hTNFR2, mTNFR1 and mTNFR2.
Affinity ($K_D$)

| Analyte | hTNFR1 | hTNFR2 | mTNFR1 | mTNFR2 |
|---|---|---|---|---|
| B2 | $1.64 \times 10^{-11}$ | $3.15 \times 10^{-10}$ | $2.56 \times 10^{-11}$ | — |
| B4 | $1.95 \times 10^{-11}$ | — | $1.32 \times 10^{-10}$ | — |
| B5 | $1.99 \times 10^{-11}$ | — | $1.28 \times 10^{-10}$ | — |
| B6 | $1.69 \times 10^{-11}$ | — | $3.04 \times 10^{-10}$ | — |
| C4 | $1.29 \times 10^{-11}$ | — | $3.23 \times 10^{-11}$ | — |
| C8 | $1.88 \times 10^{-10}$ | — | $3.63 \times 10^{-10}$ | — |

TABLE 7-continued

Single-cycle affinity data for binding of the 10 lead variants
to hTNFR1, hTNFR2, mTNFR1 and mTNFR2.
Affinity ($K_D$)

| Analyte | hTNFR1 | hTNFR2 | mTNFR1 | mTNFR2 |
|---|---|---|---|---|
| C9 | $2.48 \times 10^{-11}$ | +/− | $6.07 \times 10^{-10}$ | — |
| F3 | $6.35 \times 10^{-10}$ | — | $7.35 \times 10^{-9}$ | +/− |
| F7 | $4.24 \times 10^{-11}$ | — | $8.27 \times 10^{-11}$ | — |
| G4 | $1.71 \times 10^{-11}$ | — | $4.07 \times 10^{-11}$ | — |

+/−, a small amount of potential binding observed

Cellular Cytotoxicity Assays Using Purified Proteins

The cytotoxic activity of the 10 lead purified proteins was tested in duplicate in a cellular cytotoxicity assay using the two mouse cell lines L929 and WEHI164 as well as the human cell line HEp2 as described above. Purified hTNF, hTNF R32W S86R, mTNF as well as the irrelevant scFv were included as controls in the assays as well as a PBS control (0% killing). For each assay, cells in logarithmic growth phase were dispensed in a final volume of 50 µl into each well of a 96-well white-walled tissue culture plate in the appropriate growth media as described previously. Outer wells contained growth media only in order to avoid edge effects. A six point, four-fold dilution of purified protein (from 100 ng/ml to 0.097 ng/ml final concentration) was prepared in the appropriate growth media and added to the cells. After incubation for the indicated time the plate was equilibrated at room temperature for 10 minutes and then developed by the addition of 50 µl of Cell TiterGlo® reagent to each well prior to reading in a FluoStar Optima plate reader. % killing was calculated using the following equation:

$$\% \text{ killing}=100-(\text{Luminescence/Untreated Cells Luminescence} \times 100)$$

All 10 variants tested showed cytotoxicity in WEHI164, L929 and HEp2 cells. hTNF R32W S86R showed some activity in WEHI164, L929 and HEp2 cells. In most cases all 10 variants performed better than hTNF R32W S86R (Table 8).

Multi Cycle Kinetic Analysis of Variant Binding to hTNFR1, hTNFR2, mTNFR1 and mTNFR2

Multi cycle kinetics analysis of binding to hTNFR1, hTNFR2, mTNFR1 and mTNFR2 was performed on the 10 lead variants using a Biacore T200 (serial no. 1909913) instrument running Biacore T200 Evaluation Software V3.0.1 (Uppsala, Sweden) to characterise further the binding to these receptors.

As with the single cycle kinetics, receptor binding was assessed in two separate experiments. In the first set of experiments binding to hTNFR1 (Fc2), hTNFR2 (Fc3) and mTNFR1 (Fc4) was assessed. In the second set of experiments the extent of mTNF2 (Fc4) binding was assessed using hTNFR1 (Fc2) and hTNFR2 (Fc3) as controls. All receptors were diluted in running buffer to a concentration of ~4 µg/mL and at the start of each cycle loaded onto Fc2, Fc3 and Fc4 of a Protein A CM5 chip and captured at a flow rate of 10 µL/min to give an RU of ~40-100. The surface was then allowed to stabilise. All kinetic data was obtained using a flow rate of 75 µl/min to minimise any potential mass transfer effects. For hTNFR1, hTNFR2 and mTNFR1 kinetic analysis, a six point, two-fold dilution range was selected from 40 to 1.25 nM TNF. The association phase of TNF was monitored for 280 seconds and the dissociation phase was measured for 2100 seconds. Due to lack of binding or short dissociation kinetics observed during single cycle analysis while assessing mTNFR2 binding the association phase of TNF remained at 280 seconds, however the dissociation time was reduced to 300 seconds and the lowest concentration of receptor omitted resulting in a five point, two-fold dilution range from 40 to 2.5 nM TNF when assessing mTNTR2 binding. Regeneration of the Protein A surface was conducted using two injections of 10 mM glycine-HCL pH 1.5 at the end of each cycle. The signal from the reference channel Fc1 was subtracted from that of Fc2, Fc3 and Fc4 to correct for differences in non-specific binding to a reference surface, and a global Rmax parameter was used in the 1-to-1 binding model.

hTNF was shown to bind with high affinity to hTNFR1, hTNFR2 and mTNFR1, while hTNF R32W S86R showed

TABLE 8

Comparison of lead variants with hTNF and hTNF R32W S86T in cytotoxicity
assays using various cell lines as targets. Assays in which variants
performed as well or better than hTNF are highlighted in bold

| Variant | WEHI164 | L929 | HEp2 |
|---|---|---|---|
| B2 | ≥ hTNF | ≥ hTNF | ≥ hTNF* |
| B4 | > hTNF R32W S86T | > hTNF R32W S86T | ≥ hTNF R32W S86T |
| B5 | > hTNF R32W S86T | > hTNF R32W S86T | ≥ hTNF R32W S86T |
| B6 | > hTNF R32W S86T | > hTNF R32W S86T | ≥ hTNF |
| C4 | > hTNF R32W S86T | > hTNF R32W S86T | ≈ hTNF |
| C8 | > hTNF R32W S86T | > hTNF R32W S86T | > hTNF R32W S86T |
| C9 | > human TNF RWST | ≈ hTNF R32W S86T | ≥ hTNF |
| F3 | > hTNF R32W S86T | ≈ hTNF R32W S86T | ≈ hTNF |
| F7 | > hTNF R32W S86T | > hTNF R32W S86T | ≥ hTNF R32W S86T |
| G4 | ≥ hTNF | ≥ hTNF | ≥ hTNF |

Both mTNF and hTNF were more active than hTNF R32W S86R in all three cell types. As expected, the irrelevant scFv showed no activity in any of the assays. Variant G4 (SEQ ID NO: 2) appeared to have similar activity to hTNF in all three cell types. Variant B2 appeared to have a similar activity to hTNF when using the mouse cell lines, WEHI164 and L929, and was more active than hTNF in the human HEp2 cells.

binding to hTNFR1 but not to hTNFR2 and mTNFR1. Unlike hTNF R32W S86R, all 10 variants showed binding to both hTNFR1 and mTNFR1. Some binding to hTNFR2 was observed for B2 (SEQ ID NO: 7) although the off rate is significantly faster than that for hTNFR1 and mTNFR1. A small amount of potential binding to hTNFR2 was also observed for B4 (SEQ ID NO: 8), C8 (SEQ ID NO: 10) and C9 (SEQ ID NO: 11) although the binding and signal was not robust enough to accurately calculate kinetic data.

mTNF was shown to bind with high affinity to mTNFR2 while hTNF and hTNF R32W S86R showed very little if any binding to mTNFR2. Binding to hTNFR1 and hTNFR2 which was used to determine the integrity on the TNF proteins was consistent with previously obtained data. Consistent with the data discussed above no binding to mTNFR2 was observed for the 10 variants tested. Marginal binding to hTNFR2 was observed for B2, C8 and C9, consistent with the previous multicycle experiment. The kinetics parameters calculated for the 10 lead variants are shown in Table 9.

TABLE 9

Multi-cycle affinity data for binding of hTNF, hTNF R32W S86T and the 10 lead variants to hTNFR1, hTNFR2, mTNFR1 and mTNFR2.

| Analyte | hTNFR1 | hTNFR2 | mTNFR1 | mTNFR2 |
|---------|--------|--------|--------|--------|
| hTNF | $1.58 \times 10^{-11}$ | $3.53 \times 10^{-11}$ | $6.67 \times 10^{-11}$ | — |
| hTNF R32W S86T | $3.54 \times 10^{-9}$ | — | — | — |
| B2 | $2.16 \times 10^{-11}$ | $4.07 \times 10^{-10}$ | $1.77 \times 10^{-10}$ | — |
| B4 | $1.10 \times 10^{-10}$ | —* | $1.53 \times 10^{-10}$ | — |
| B5 | $5.91 \times 10^{-11}$ | — | $2.89 \times 10^{-10}$ | — |
| B6 | $3.39 \times 10^{-10}$ | — | $5.90 \times 10^{-10}$ | — |
| C4 | $3.06 \times 10^{-11}$ | — | $2.08 \times 10^{-10}$ | — |
| C8 | $2.61 \times 10^{-10}$ | $4.13 \times 10^{-9**}$ | $1.12 \times 10^{-10}$ | — |
| C9 | $7.17 \times 10^{-11}$ | $2.89 \times 10^{-7**}$ | $1.13 \times 10^{-9}$ | — |
| F3 | $4.62 \times 10^{-10}$ | — | $5.08 \times 10^{-9}$ | — |
| F7 | $4.65 \times 10^{-11}$ | — | $2.08 \times 10^{-10}$ | — |
| G4 | $8.72 \times 10^{-12}$ | — | $1.40 \times 10^{-10}$ | — |

*A residual amount of binding above background potentially observed but no KD determined.
**A residual amount of binding is observed but 1 to 1 model is a poor fit Example 8: CD4+ T Cell Epitope Avoidance The amino acid sequences of the 10 purified variants were analysed using iTope™ technology for in silico analysis of peptide binding to human MHC class II alleles (Perry et al 2008), and using the TCED™ of known protein sequence-related T cell epitopes (Bryson et al 2010).

The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by one amino acid spanning the test protein sequence. However, all predictive methods for MHC class II binding inherently over-predict the number of T cell epitopes since they do not allow for other important processes during antigen presentation such as protein/peptide processing, recognition by the T cell receptor or T cell tolerance to the peptide. The TCED™ contains the sequences of all the peptides previously screened in EpiScreen™ T cell epitope mapping assays. The TOED™ is used to search any test sequence against a large (>10,000 peptides) database of peptides derived from unrelated protein and antibody sequences which have been tested in EpiScreen™ T cell epitope mapping assays.

All potential binding peptides present in common within hTNF have been excluded from the analysis based on the assumption that hTNF is tolerated and thus non-immunogenic. The C-terminus of each TNF protein contains a His6 tag for purification and a FLAG tag for detection. The C-terminus is associated with four iTope™ Promiscuous High Epitopes and one iTope™ Promiscuous Moderate Epitope. The C-terminus has also been excluded from the iTope™ analysis of the lead muteins. iTope™ in silico analysis of the variants is summarised in Table 10.

TABLE 10 iTope ™ in silico analysis of hTNF, hTNF R32W S86T and the 10 lead variants. Summary of high and moderate affinity MHC class II binding peptides which showed promiscuous binding, based on the assumption that hTNF is tolerated and thus non-immunogenic.

| Variant | Library | iTope ™ Promiscuous High Epitopes | iTope ™ Promiscuous Moderate Epitopes |
|---------|---------|-----------------------------------|----------------------------------------|
| hTNF | — | 0 | 0 |
| hTNF R32W S86T | — | 0 | 4 |
| B2 | 1 | 0 | 1 |
| B4 | 1 | 1 | 1 |
| B5 | 1 | 0 | 1 |
| B6 | 1 | 0 | 1 |
| C4 | 1 | 1 | 1 |
| C8 | 1 | 0 | 1 |
| C9 | 2 | 0 | 2 |
| F3 | 1 | 1 | 2 |
| F7 | 1 | 1 | 4 |
| G4 | 1 | 0 | 1 | hTNF R32W S86T contains four promiscuous moderate epitopes when hTNF is set as the non-immunogenic reference. In variants B4, C4, F3 and F7 one promiscuous high epitope has been introduced which is not observed in the hTNF R32W S86T sequence. Variant B4 contains a R6H mutation and variants B5 and F7 contain a R2H mutation which is outside of the regions targeted during library design. Variant F3 contains a I155V mutation which does not introduce any promiscuous epitopes. Variant F7 also contains a A134V change which introduces a promiscuous low epitope. These changes were likely introduced by PCR during library construction.

Example 9: 1 Year Stability Study

The stability of the top 6 of the lead variants (B2, B5, B6, F3, F7 and G4) was assessed following storage at −20° C. and −80° C. for 3 months and 1 year.

At day zero (prior to freezing) and following thawing on ice after 3 months and 1 year the following assays were performed:
SDS-PAGE
OD280 nm
Single cycle Biacore for binding to hTNFR1, hTNFR2 and mTNFR1

Lead variants were expressed and purified by Ni-NTA and SEC and frozen at ~1 mg/ml in PBS in glass vials baked at 210° C. for one hour (ThermoFisher Scientific, cat. no. 2-CV). 2 vials for each condition (−20° C. and −80° C.) and each time point (3 months and 1 year) were frozen down (Day zero).

Tables 11 and 12 show that no significant (+/−10%) changes in protein concentration were observed following storage for 12 months at either −20° C. or −80° C. Similarly, SDS-PAGE analysis showed that bands of the expected size were observed and no significant changes in protein integrity were observed following storage for 12 months at either −20° C. or −80° C.

TABLE 11

| | | | |
|---|---|---|---|
| Protein concentration of TNF variants measured using OD280 nm at various time points | | | |
| | | $OD_{280}$ | |
| Variant | t = 0 | −20° C. 12 months | −80° C. 12 months |
| B2 | 1.08 | 1.16 | 1.14 |
| B5 | 1.13 | 1.19 | 1.14 |
| B6 | 1.23 | 1.25 | 1.25 |
| F3 | 1.14 | 1.14 | 1.2 |
| F7 | 1.02 | 1.09 | 1.07 |
| G4 | 1.42 | 1.51 | 1.44 |

TABLE 12

| | | | |
|---|---|---|---|
| Relative protein concentration of TNF variants measured using OD280 nm after 12 months Relative absorbance (t = 0 OD280/t = 12 month OD280) | | | |
| Variant | t = 0 | −20° C. 12 months | −80° C. 12 months |
| B2 | 1.00 | 0.93 | 0.95 |
| B5 | 1.00 | 0.95 | 0.99 |
| B6 | 1.00 | 0.99 | 0.98 |
| F3 | 1.00 | 1.00 | 0.95 |
| F7 | 1.00 | 0.94 | 0.95 |
| G4 | 1.00 | 0.94 | 0.99 |

A Biacore single cycle kinetic screen (as described above) of the TNF variants demonstrated that binding kinetics prior to freezing are similar to those observed following storage for 12 months at either −20° C. or −80° C. As shown in Table 13, storage under freezing conditions did not alter the binding kinetics with respect to hTNFR2 and there was no evidence to suggest that storage in the tested conditions had a detrimental effect on the integrity or binding of B2, B5, F7 and G4. For B6 there appears to be a small loss of binding to hTNFR1 following storage at −20° C. or −80° C. for a year. For F3 there appears to be a small loss of binding to mTNFR1 following storage at −20° C. or −80° C. for a year.

TABLE 13

| | | | | |
|---|---|---|---|---|
| $K_d$ of TNF muteins for various receptors following storage at −20° C. or −80° C. for a year. | | | | |
| Variant | Storage condition | hTNFR1 $K_D$ | hTNFR2 $K_D$ | mTNFR1 $K_D$ |
| B2 | 0 | $1.75 \times 10^{-11}$ | $1.98 \times 10^{-10}$ | $6.24 \times 10^{-11}$ |
| | 1 year −20° C. | $3.90 \times 10^{-11}$ | $2.10 \times 10^{-10}$ | $8.51 \times 10^{-11}$ |
| | 1 year −80° C. | $4.07 \times 10^{-11}$ | $3.49 \times 10^{-10}$ | $8.64 \times 10^{-11}$ |
| B5 | 0 | $3.55 \times 10^{-11}$ | — | $7.71 \times 10^{-11}$ |
| | 1 year −20° C. | $4.93 \times 10^{-11}$ | — | $1.15 \times 10^{-10}$ |
| | 1 year −80° C. | $4.46 \times 10^{-11}$ | — | $9.77 \times 10^{-11}$ |
| B6 | 0 | $9.69 \times 10^{-11}$ | — | $6.70 \times 10^{-11}$ |
| | 1 year −20° C. | $5.26 \times 10^{-11}$ | — | $7.11 \times 10^{-10}$ |
| | 1 year −80° C. | $6.67 \times 10^{-11}$ | — | $4.74 \times 10^{-11}$ |
| F3 | 0 | $1.20 \times 10^{-11}$ | — | $1.10 \times 10^{-10}$ |
| | 1 year −20° C. | $2.71 \times 10^{-11}$ | — | $5.27 \times 10^{-10}$ |
| | 1 year −80° C. | $2.30 \times 10^{-11}$ | — | $3.98 \times 10^{-10}$ |
| F7 | 0 | $2.20 \times 10^{-11}$ | — | $1.16 \times 10^{-10}$ |
| | 1 year −20° C. | $2.62 \times 10^{-11}$ | — | $1.11 \times 10^{-10}$ |
| | 1 year −80° C. | $3.53 \times 10^{-11}$ | — | $1.65 \times 10^{-10}$ |
| G4 | 0 | $1.73 \times 10^{-11}$ | — | $7.00 \times 10^{-11}$ |
| | 1 year −20° C. | $3.31 \times 10^{-11}$ | — | $6.92 \times 10^{-11}$ |
| | 1 year −80° C. | $3.99 \times 10^{-11}$ | — | $4.58 \times 10^{-11}$ |

Example 10: Assessment of TNF Mutein Half-Life in Plasma

The amount of TNF or TNF mutein detectable in plasma was measured over a period of 60 minutes. The half-life for hTNF was determined to be 5.6 minutes. The TNF muteins showed half-lives within the range of the wild-type hTNF, with G4 (SEQ ID NO: 2) having the closest half-life to wild-type. The results are set out in Table 14.

TABLE 14

| | |
|---|---|
| Half-life of hTNF and lead muteins in plasma | |
| Protein | Half-life in plasma (mins) |
| hTNF | 5.6 |
| B2 | 4.1 |
| B5 | 20.5 |
| B6 | 5.2 |
| F3 | 7.25 |
| F7 | 10 |
| G4 | 5.8 |

Example 11: Safety Assessment of Mutein G4 (SEQ ID NO: 2) on Administration to Mice The heart, lung, liver, brain, spleen and left kidney were examined from 16 mice from four groups—treated with saline, mouse TNF, human TNF and Mutein G4.

Histological slides were prepared and stained with H&E. Findings in the tissue were scored using a non-linear semi-quantitative grading system from 0 to 5 where 0=no significant change and 5=whole organ or tissue affected. For some lesions grading is not appropriate and they are scored P for present if seen.

There were no clear differences between groups. Two of the saline treated animals had slightly less extramedullary haematopoiesis (EMH) in the spleen which reflected in the slightly lower group mean spleen weight. However, the appearance of the spleen and amount of EMH is variable and all animals fell within the range of appearance expected in most mice strains. The spleens show no morphological changes which would be expected in immune-deficient animals despite the reduced WBC count seen in the haematology profiles.

Example 12: Dose Response and Window of Permeabilisation Studies of TNF Muteins (mutTNF) in a Brain Metastasis Model Materials and Methods All experiments were performed in accordance with the ARRIVE Guidelines and Guidelines for the Welfare and Use of Animals in Cancer Research. For in vivo experiments, 4T1-GFP cells were cultured as described previously (Connell et al. J Natl Cancer Inst. 2013; 105(21):1634-1643; Serres et al., Proc Natl Acad Sci USA. 2012; 109(17):6674-6679; and Soto et al., Neuro Oncol. 2014; 16(4):540-551) Female BALB/c mice (Charles River Kent, UK) were anaesthetised with isoflurane and injected via the left cardiac ventricle, under ultrasound guidance (Vevo 3100 Imaging System; Fujifilm VisualSonics), with 1×105 4T1-GFP cells in 100 μl of sterile phosphate buffered saline.

To determine the dose-response of permeabilisation, at 13 days post-metastasis induction, mice were injected intravenously with 5, 16.7, 50 or 150 μg/kg of the G4 mutein (mutTNF) in 100 μl saline, or saline alone (n=3-4 per group). Mice were perfusion-fixed 2 h later, and BBB permeability assessed using either horseradish peroxidase (HRP) histochemistry, or IgG immunohistochemistry (150 μg/kg mutTNF dose omitted). For HRP histochemistry, mice were injected intravenously with 100 μl type II HRP (300 units; SigmaAldrich, Dorset, UK) 30 min prior to transcardial perfusion-fixation with Karnovsky's fixative. For IgG assessment of BBB permeabilisation, mice were transcardially perfusion-fixed with PLPlight fixative.

To determine the window of permeabilisation, at 10 days post-metastasis induction, mice were injected via a tail vein with 50 μg/kg mutTNF G4 in 100 μl saline, or saline only, and perfusion-fixed, as above, for HRP histology 2, 12, 24 or 72 h later (n=6 per group).

HRP and IgG Histochemistry to Assess BBB Permeability

For HRP assessment of BBB permeability, alternate sections were stained with Hanker-Yates, as described previously, (Connell et al., supra) and cresyl violet (SigmaAldrich, Dorset, UK). Each metastasis >50 μm in diameter on cresyl violet sections was assigned as either positive or negative for HRP staining on the adjacent Hanker-Yates stained sections. For IgG assessment of permeabilisation, all brain sections were immunostained for IgG, and each metastasis counted as either positive or negative for IgG staining.

Magnetic Resonance Imaging Assessment of BBB Permeability

BALB/c mice injected intracardially with 4T1-GFP cells underwent magnetic resonance imaging (MRI) 13 days after metastasis induction, as described previously (Connell et al., supra). Pre- and post-Gd-DTPA T1-weighted images were acquired before and 2 h after mutTNF G4 injection (5, 16.7 or 50 ug/kg) or saline alone (n=6 per group). Pre-Gd-DTPA images were subtracted from post-Gd-DTPA images and a mask created for all voxels with signal intensity greater than mean+2SD for normal brain. This mask was applied to the post-Gd images, which were then cross-referenced with the corresponding histological sections to confirm metastasis presence and percentage signal change in metastasis-containing ROIs calculated. For full details of image acquisition and analysis.

Results

Dose Response and Window of BBB Permeabilisation

HRP-positive metastases, indicating BBB breakdown, were evident in all mice treated with the mutTNF G4, with the number increasing in a dose-dependent manner. No breakdown was evident in non-tumour bearing normal brain tissue. Some natural BBB breakdown was evident at metastatic sites in the saline group, as expected at this time-point (day 13), particularly for brain metastases >400 μm diameter. Nonetheless, the numbers of HRP-positive metastases as a percentage of total metastases (47.8±3.3%, 55.1±8.0% and 64.2±7.6%) at the 3 highest doses of mutTNF G4 (16.7, 50 and 150 μg/kg, respectively) were significantly greater than in the saline group (30.9±4.8%; FIG. 3).

The above findings were confirmed through staining for endogenous serum IgG, which is normally excluded from the brain by an intact BBB. In this case, the percentages of IgG-positive metastases (57.0±8.1%, 50.9±4.9% and 41.2±1.4%; at 5, 16.7 and 50 μg/kg, respectively) were significantly greater than in the saline group (26.6±2.3%) for all mutTNF doses (FIG. 7).

For the window study, although BBB breakdown was evident at all time-points after mutTNF administration, the percentage of HRP-positive metastases decreased over time. Thus, significant breakdown was still evident in mutTNF mice compared to saline treated mice at 24 h, but not 72 h, post-treatment (FIG. 8).

Gd-DTPA Enhancement in Brain Metastases

Extravasation and accumulation of Gd-DTPA enables BBB breakdown to be detected in vivo as hyperintense areas on T1-weighted MR images. Post-Gd-DTPA T1-weighted images indicated a small number of metastases exhibiting natural BBB breakdown prior to mutTNF treatment, and these were excluded from the analysis.

At 2 h after mutTNF treatment, areas of hyperintensity were evident on post-Gd-DTPA images compared to pre-Gd-DTPA images, which corresponded spatially with sites of metastases. The majority of animals in the saline group did not show Gd-DTPA contrast enhancement; where occasional hyperintensities were evident, these showed lower contrast and a more spatially restricted profile than in the mutTNF-treated animals. This low level of breakdown likely reflects natural breakdown at metastatic sites that was missed in the pre-treatment scans owing to their lower resolution. The ratio of signal intensity at sites shown to contain metastases vs. equivalent non-tumour bearing regions was significantly greater at all mutTNF concentrations compared to the saline-injected group (FIG. 9).

Example 13: BBB Permeabilisation of Endothelial Cell Monolayers

Materials and Methods

Paracellular Permeability Assay in hCMEC/D3 Cells

Human brain microvascular endothelial hCMEC/D3 cells were cultured as described previously (Lopez-Ramirez et al. J Immunol. 2016; 189(19):3130-3139). Permeabilising activity of the 10 lead mutTNFs on monolayers of hCMEC/D3 cells was assessed using a FITC-labeled 70 kDa dextran tracer (SigmaAldrich, Dorset, UK) assay. Confluent monolayers on permeable polyester transwell inserts were treated with mutTNF, wild-type hTNF or vehicle for 24 h. Subsequently, paracellular flux of FITC-dextran across the insert was evaluated and permeability coefficients calculated.

Results

All mutTNFs induced significant permeability in vitro (FIGS. 4, 5 and 6). However, mutTNF G4 showed a significantly higher permeability coefficient (Pe) than wild-type hTNF at the lowest dose studied (0.1 ng/mL; FIG. 4), indicating an enhanced permeabilising activity.

The invention claimed is:

1. A tumour necrosis factor (TNF) mutein comprising an amino acid sequence having at least 90% sequence identity to any one of SEQ ID NOS: 2 to 10 which comprises an amino acid sequence selected from any one of SEQ ID NOS: 12-20 at positions equivalent to positions 84 to 89 of SEQ ID NO: 1, wherein the mutein is an agonist of tumour necrosis factor receptor 1 (TNFR1) and binds selectively to TNFR1.

2. The mutein of claim 1, wherein the mutein comprises an amino acid sequence having at least 95% sequence identity to any one of SEQ ID NOs: 2 to 10.

3. The mutein of claim 1, wherein the mutein comprises an amino acid sequence selected from any one of SEQ ID NOs: 2 to 10.

4. A pharmaceutical composition comprising a TNF mutein as defined in claim 1 and one or more pharmaceutically acceptable carriers, diluents and/or excipients.

5. The pharmaceutical composition of claim 4, wherein said pharmaceutical composition further comprises an anticancer agent and said anticancer agent is selected from the group consisting of a chemotherapeutic agent, an oncolytic virus and an exosome containing a therapeutic nucleic acid molecule, and/or said pharmaceutical composition further comprises a signal generating molecule and said signal generating molecule is selected from the group consisting of a gadolinium-based compound and an iron oxide contrast agent.

6. A method of permeabilising the vasculature of a tumour in a patient for treating, detecting or diagnosing said tumour, comprising administering to said patient a TNF mutein according to claim 1, wherein said TNF mutein is systemically administered to said patient.

7. A method of permeabilising the vasculature of a tumour in a patient, comprising administering to said patient a TNF mutein according to claim 1, for:

(i) treating said tumour, wherein said TNF mutein is systemically administered with an anticancer agent; or (ii) detecting or diagnosing said tumour, wherein said TNF mutein is systemically administered with a signal generating agent.

8. The method according to claim 6, wherein the tumour is: (i) a CNS tumour; (ii) a metastasis; and/or (iii) a metastasis in the CNS, liver, bone or breast.

9. The method according to claim 6, wherein the tumour is less than 20 mm in diameter.

10. The method according to claim 7, wherein:

(i) said anticancer agent is selected from the group consisting of a chemotherapeutic agent, an oncolytic virus and an exosome containing a therapeutic nucleic acid molecule; or (ii) said signal generating molecule is selected from the group consisting of a gadolinium-based compound and an iron oxide contrast agent.

11. The method according to claim 10, wherein the TNF mutein and anticancer agent are administered simultaneously, separately or sequentially.

12. The method according to claim 10, wherein the TNF mutein and signal generating agent are administered simultaneously, separately or sequentially.

13. The mutein of claim 1, wherein the mutein comprises:

(i) a substitution at a position equivalent to position 2 of SEQ ID NO: 1;

(ii) a substitution at a position equivalent to position 134 of SEQ ID NO: 1; and/or (iii) a substitution at a position equivalent to position 155 of SEQ ID NO: 1.

14. The mutein of claim 13, wherein the substitution is a conservative substitution.

15. The mutein of claim 1, wherein the mutein comprises:

(i) a histidine at a position equivalent to position 2 of SEQ ID NO: 1;

(ii) a valine at a position equivalent to position 134 of SEQ ID NO: 1; and/or (iii) a valine at a position equivalent to position 155 of SEQ ID NO: 1.

16. The mutein of claim 1, wherein the mutein comprises an amino acid sequence of LNRR (SEQ ID NO: 29) at positions equivalent to positions 29-32 of SEQ ID NO: 1 and/or an amino acid sequence of FAES (SEQ ID NO: 30) at positions equivalent to positions 144-147 of SEQ ID NO: 1.

17. A tumour necrosis factor (TNF) mutein which comprises at least 4 amino acid mutations compared to a wild-type TNF sequence, wherein said mutations comprise:

(a) a substitution of the residue at the position equivalent to position 84 of SEQ ID NO. 1;

(b) a substitution of the residue at the position equivalent to position 85 of SEQ ID NO. 1;

(c) a substitution of the residue at the position equivalent to position 88 of SEQ ID NO. 1; and (d) a substitution of the residue at the position equivalent to position 89 of SEQ ID NO. 1, wherein the mutein is an agonist of tumour necrosis factor receptor 1 (TNFR1) and binds selectively to TNFR1, and wherein the mutein comprises an amino acid sequence selected from any one of SEQ ID NOs: 2 to 10.

18. The pharmaceutical composition of claim 5, wherein said chemotherapeutic agent is selected from the group consisting of lapatinib, doxorubicin, trastuzumab, melphalan and paclitaxel.

19. The pharmaceutical composition of claim 10, wherein said chemotherapeutic agent is selected from the group consisting of lapatinib, doxorubicin, trastuzumab, melphalan and paclitaxel.

* * * * *